US010022388B2

(12) United States Patent
Mendel et al.

(10) Patent No.: US 10,022,388 B2
(45) Date of Patent: Jul. 17, 2018

(54) OXIDIZED LIPIDS AND TREATMENT OR PREVENTION OF FIBROSIS

(71) Applicant: Vascular Biogenics Ltd., Or Yehuda (IL)

(72) Inventors: Itzhak Mendel, Rehovot (IL); Yaniv Salem, Kyriat Ono (IL); Niva Yacov, Tel Aviv (IL); Eyal Breitbart, Hashmonaim (IL)

(73) Assignee: Vascular Biogenics Ltd., Or Yehuda (UA)

( * ) Notice: Subject to any disclaimer, the term of this patent is extended or adjusted under 35 U.S.C. 154(b) by 0 days.

(21) Appl. No.: 15/602,435

(22) Filed: May 23, 2017

(65) Prior Publication Data

US 2017/0258818 A1 Sep. 14, 2017

Related U.S. Application Data

(63) Continuation of application No. PCT/IB2015/059133, filed on Nov. 26, 2015.

(60) Provisional application No. 62/085,051, filed on Nov. 26, 2014.

(51) Int. Cl.
A61K 31/685 (2006.01)
A61K 9/00 (2006.01)
C07F 9/10 (2006.01)

(52) U.S. Cl.
CPC .......... *A61K 31/685* (2013.01); *A61K 9/0053* (2013.01); *C07F 9/106* (2013.01)

(58) Field of Classification Search
None
See application file for complete search history.

(56) References Cited

U.S. PATENT DOCUMENTS

| | | | |
|---|---|---|---|
| 4,329,302 A | 5/1982 | Hanahan et al. |
| 4,450,877 A | 5/1984 | Walker et al. |
| 4,543,258 A | 9/1985 | Urata et al. |
| 4,614,796 A | 9/1986 | Kawamata et al. |
| 4,622,180 A | 11/1986 | Paltauf et al. |
| 4,778,912 A | 10/1988 | Inoue et al. |
| 4,827,011 A | 5/1989 | Wissner et al. |
| 4,978,670 A | 12/1990 | Rector et al. |
| 5,053,402 A | 10/1991 | Masaki et al. |
| 5,061,626 A | 10/1991 | Baldo et al. |
| 5,091,527 A | 2/1992 | Junius et al. |
| 5,561,052 A | 10/1996 | Koike |
| 5,660,855 A | 8/1997 | Malé-Brune |
| 5,614,548 A | 9/1997 | Piantadosi et al. |
| 5,962,437 A | 10/1999 | Kucera et al. |
| 5,985,292 A | 10/1999 | Fourneron et al. |
| 6,017,513 A | 1/2000 | Betbeder et al. |
| 6,261,597 B1 | 7/2001 | Kurtz |
| 6,348,583 B1 | 2/2002 | Segev |
| 6,414,168 B1 | 7/2002 | Crivello et al. |
| 6,838,452 B2 | 1/2005 | Harats et al. |
| 7,186,704 B2 | 3/2007 | Harats et al. |
| 7,504,388 B2 | 3/2009 | Harats et al. |
| 7,517,858 B1 | 4/2009 | Hostetier et al. |
| 7,625,882 B2 * | 12/2009 | Harats ................. A61K 31/075 |
| | | | 514/114 |
| 7,807,847 B2 | 10/2010 | Halperin et al. |
| 7,893,291 B2 | 2/2011 | Harats et al. |
| 7,902,176 B2 | 3/2011 | Harats et al. |
| 7,973,023 B2 | 7/2011 | Harats et al. |
| 8,084,209 B2 | 12/2011 | Medina et al. |
| 8,124,800 B2 | 2/2012 | Halperin et al. |
| 8,158,611 B2 | 4/2012 | Harats et al. |
| 8,501,715 B2 | 8/2013 | Harats et al. |
| 8,563,534 B2 | 10/2013 | Harats et al. |
| 8,569,529 B2 | 10/2013 | Halperin et al. |
| 8,759,557 B2 | 6/2014 | Halperin et al. |
| 8,802,875 B2 | 8/2014 | Halperin et al. |
| 8,999,960 B2 | 4/2015 | Halperin et al. |
| 9,006,217 B2 | 4/2015 | Halperin et al. |
| 9,206,206 B2 | 12/2015 | Breitbart et al. |
| 9,254,297 B2 | 2/2016 | Sher et al. |
| 9,566,288 B2 | 2/2017 | Halperin et al. |
| 2003/0225035 A1 | 12/2003 | Harats et al. |
| 2006/0140936 A1 | 6/2006 | Goldenberg et al. |
| 2006/0194765 A1 | 8/2006 | Garcia et al. |
| 2007/0020691 A1 | 1/2007 | Kanter et al. |
| 2007/0099868 A1 | 5/2007 | Harats et al. |
| 2007/0264206 A1 | 11/2007 | Boga et al. |
| 2008/0261865 A1 | 10/2008 | Harats et al. |
| 2009/0074720 A1 | 3/2009 | Sabbadini |
| 2009/0149541 A1 | 6/2009 | Stark et al. |

(Continued)

FOREIGN PATENT DOCUMENTS

| | | |
|---|---|---|
| AU | 2004243695 A1 | 12/2004 |
| CA | 1102354 | 6/1981 |

(Continued)

OTHER PUBLICATIONS

Huebener et al., Regulation of wound healing and organ fibrosis by toll-like receptors, Biochimica et Biophysica Acta, 1832 (2013) 1005-1017.*
Haitao et al., Toxicology, Limerick, IR, vol. 303, Nov. 9, 2012, pp. 107-114, XP028975589.*
Berchtold, R., "Synthesis of Carboxyphospholipids," *Chem. Phys. Lipids* 18(1):55-60, Elsevier, Netherlands (1981).
Bochkov, V.N., "Inflammatory Profile of Oxidized Phospholipids," *Journal of Thrombosis and Haematosis*, 97:348-354, Schattauer GmbH, Germany (2007).
Boullier, A., et al., "The Binding of Oxidized Low Density Lipoprotein to Mouse CD36 is Mediated in Part by Oxidized Phospholipids That Are Associated With Both the Lipid and Protein Moieties of the Lipoprotein," *Journal of Biological Chemistry*, 275(13):9163-9169, The American Society for Biochemistry and Molecular Biology, Inc., United States (2000).

(Continued)

*Primary Examiner* — Svetlana M Ivanova
(74) *Attorney, Agent, or Firm* — Sterne, Kessler, Goldstein & Fox P.L.L.C.

(57) ABSTRACT

The present invention is directed to methods of treating or preventing fibrosis comprising an oxidized lipid or pharmaceutical composition comprising the same.

19 Claims, 27 Drawing Sheets

(56) References Cited

U.S. PATENT DOCUMENTS

| | | |
|---|---|---|
| 2009/0197242 A1 | 8/2009 | Kaddurah-Daouk et al. |
| 2010/0048515 A1 | 2/2010 | Harats et al. |
| 2011/0189212 A1 | 8/2011 | Harats et al. |
| 2011/0195937 A1 | 8/2011 | Breitbart et al. |
| 2011/0207703 A1 | 8/2011 | Kovalevski-Ishai et al. |
| 2012/0130108 A1 | 5/2012 | Halperin et al. |
| 2012/0329757 A1 | 12/2012 | Harats et al. |
| 2012/0329758 A1 | 12/2012 | Cohen et al. |
| 2013/0079540 A1 | 3/2013 | Halperin |
| 2013/0172294 A1 | 7/2013 | Cohen et al. |
| 2013/0203707 A1 | 8/2013 | Kovalevski-Ishai et al. |
| 2013/0209555 A1 | 8/2013 | Sher et al. |
| 2013/0225525 A1 | 8/2013 | Cohen et al. |
| 2013/0237720 A1 | 9/2013 | Halperin et al. |
| 2015/0216882 A1 | 8/2015 | Halperin et al. |
| 2015/0320773 A1 | 11/2015 | Mendel et al. |
| 2016/0008381 A1 | 1/2016 | Cohen et al. |
| 2016/0038518 A1 | 2/2016 | Sher et al. |
| 2016/0220590 A1 | 8/2016 | Sher et al. |
| 2016/0304544 A1 | 10/2016 | Ishai et al. |

FOREIGN PATENT DOCUMENTS

| | | | |
|---|---|---|---|
| CH | 642 665 A5 | 4/1984 | |
| EP | 0 121 088 A1 | 10/1984 | |
| EP | 0 142 333 A2 | 5/1985 | |
| EP | 0 184 905 A1 | 6/1986 | |
| EP | 0 225 129 A1 | 6/1987 | |
| EP | 0 331 167 A2 | 9/1989 | |
| ES | 2 019 552 A6 | 6/1991 | |
| GB | 2 130 206 A | 5/1984 | |
| JP | 50004040 A | 1/1975 | |
| JP | 54-41807 | 4/1979 | |
| JP | 58154512 | 9/1983 | |
| JP | 59-93022 | 5/1984 | |
| JP | 59-175445 | 10/1984 | |
| JP | 60-104066 A | 6/1985 | |
| JP | 62-228088 | 11/1986 | |
| JP | 62-000094 A | 1/1987 | |
| JP | 62-030714 A | 2/1987 | |
| JP | 63-054386 A | 3/1988 | |
| JP | 63-135395 A | 6/1988 | |
| JP | 01-258691 A | 10/1989 | |
| JP | 02-006493 | 1/1990 | |
| JP | 02-048585 A | 2/1990 | |
| JP | 03-258740 | 11/1991 | |
| JP | 04-021691 | 1/1992 | |
| JP | 05-339387 | 12/1993 | |
| JP | 07-258261 A | 10/1995 | |
| JP | 08-059545 | 3/1996 | |
| JP | 08-208548 | 8/1996 | |
| JP | 11-116563 A | 4/1999 | |
| JP | 2003-515550 A | 5/2003 | |
| JP | 2004-537498 A | 12/2004 | |
| JP | 2005-505499 | 2/2005 | |
| JP | 2005-507952 A | 3/2005 | |
| JP | 2008-037763 A | 2/2008 | |
| SU | I400511 A3 | 5/1988 | |
| WO | WO 1987/05904 A1 | 10/1987 | |
| WO | WO 1995/23592 | 9/1995 | |
| WO | WO 2001/39744 A2 | 6/2001 | |
| WO | WO 2001/75168 A1 | 10/2001 | |
| WO | WO 02/41827 A2 | 5/2002 | |
| WO | WO 2002/41827 A2 | 5/2002 | |
| WO | WO 02/087465 A2 | 11/2002 | |
| WO | WO 2003/040073 A1 | 5/2003 | |
| WO | WO 2004/106486 A2 | 12/2004 | |
| WO | WO 2006/006161 A2 | 1/2006 | |
| WO | WO 2008/084472 A2 | 7/2008 | |
| WO | WO 2010/041242 A2 | 4/2010 | |
| WO | WO 2010/052718 A1 | 5/2010 | |
| WO | WO 2011/083464 A1 | 7/2011 | |
| WO | WO 2011/083465 A1 | 7/2011 | |
| WO | WO 2011/083466 A1 | 7/2011 | |
| WO | WO 2011/083467 A1 | 7/2011 | |
| WO | WO 2011/083469 A1 | 7/2011 | |
| WO | WO 2013/033642 A1 | 3/2013 | |
| WO | WO 2013/088245 | 6/2013 | |
| WO | WO 2013088245 A1 * | 6/2013 | ........... A61K 31/685 |
| WO | WO 2013/121300 | 8/2013 | |
| WO | WO 2016/084023 | 6/2016 | |
| WO | WO 2016/084024 | 6/2016 | |

OTHER PUBLICATIONS

Chen, X., et al., "Polyunsaturated Phospholipids Promote the Oxidation and Fragmentation of γ-Hydroxyalkenals: Formation and Reactions of Oxidatively Truncated Ether Phospholipids," *Journal of Lipid Research*, 49:832-846, American Society for Biochemistry and Molecular Biology, United States (2008).

Cooney, S., et al., "Combining site specificities of rabbit antibodies to platelet-activating factor (PAF)," *Mol. Immunol.* 27(5):405-12, Pergamon Press, Great Britain (1990).

Davies, S., et al. "Oxidized Alkyl Phospholipids are Specific, High Affinity Peroxisome Proliferator-Activated Receptor γ Ligands and Agonists," *Journal of Biological Chemistry* 276(19):16015-016023, The American Society for Biochemistry and Molecular Biology, Inc., United States (2001).

Deigner, H-P. and Dresel, H.A., "Effect of platelet activating factor on the kinetics of LDL oxidation in vitro," *FEBS Lett.* 317(3):202-6, Elsevier Science, Netherlands (1993).

George, J., et al. "Hyperimmunization of Apo-E-Deficient Mice with Homologous Malondialdehyde Low-Density Lipoprotein Suppresses early Atherogenisis," *Atherosclerosis* 138:147-152, Elsevier Science, Ireland (1998).

Hoff, H.F., et al., "Phospholipid Hydroxyalkenals: Biological and Chemical Properties of Specific Oxidized Lipids Present in Atherosclerotic Lesions," *Arterioscler. Thromb. Vasc. Biol.* 23:275-282, The American Heart Association, United States (2003).

Itabe, H., et al. "Oxidized Phosphatidylcholines That Modify Proteins," *Journal of Biological Chemistry* 271(52):33208-33217, The American Society for Biochemistry and Molecular Biology, United States (1996).

Itabe, H., et al., "Preparation of radioactive aldehyde-containing phosphatidylcholine," *Anal. Biochem.* 285(1):151-5, Academic Press, United States (2000).

Kamido, H., et al., "Lipid ester-bound aldehydes among copper-catalyzed peroxidation products of human plasma lipoproteins," *J Lipid Res.* 36(9):1876-1886, American Society for Biochemistry and Molecular Biology, United States (1995).

Karasawa, K., et al., "Antibodies to synthetic platelet-activating factor (1-0-alkyl-2-0-acetyl-sn-glycero-3-phosphocholine) analogues with substitiuents at the sn-2 position," *J. Biochem.* 110(5):683-7, Oxford University Press, England (1991).

Kern, H., "Stimulation of monocytes and platelets by short-chain phosphatidylcholines with and without terminal carboxyl group," *Biochim. Biophys. Acta* 1394(1):33-42, Elsevier, Netherlands (1998).

Leitinger, N., et al. "Structurally Similar Oxidized Phospholipids Differentially Regulate Endothelial Binding of Monocytes and Neutrophiols," *Proc. Natl. Acad. Sci.* 96(21):12020-12015, National Academy of Sciences, United States (1999).

MacPherson, J.L., et al., "Production and characterization of antibodies to platelet-activating factor," *J. Lipid. Mediat.* 5(1):49-59, Elsevier Science Publishers, Netherlands (1992).

Mendel, I., et al., "A Lecinoxoid, an oxidized phospholipid small molecule, constrains CNS autoimmune disease," *J. Neuroimmunol.* 226:126-35, Elsevier B.V., Netherlands (2010).

Nitta, T., et al., "Phospholipase $A_2$ Activity of $Fe_{\gamma 2b}$ Receptors of Thioglycollate-Elicited Murine Peritoneal Macrophages," *J. Leuk. Biol.* 36(4):493-504, Wiley-Liss, United States (1984).

"The Nomenclature of Lipids," *Journal of Lipid Research* 8:523-528, American Society for Biochemistry and Molecular Biology, United States (1967).

Ota, Y., "Complexes of apoA-1 with phosphatidylcholine suppress dysregulation of arterial tone by oxidized LDL," *Am. J. Physiol.* 273(3), Part 2:H1215-22, The American Physiological Society, United States (1997).

(56) References Cited

OTHER PUBLICATIONS

Podrez, E.A., et al., "A Novel Family of Atherogenic Oxidized Phospholipids Promotes Macrophage Foam Cell Formation Via the Scavenger Receptor CD36 and Is Enriched in Atherosclerotic Lesions," *J. Biol. Chem.* 277(41): 38517-38523, The American Society for Biochemistry and Molecular Biology, Inc., United States (2002).

Podrez, E.A., et al., "Identification of a Novel Family of Oxidized Phospholipids That Serve as Ligands for the Macrophage Scavenger Receptor CD36," *J. Biol. Chem.* 277(41): 38503-38516, The American Society for Biochemistry and Molecular Biology, Inc., United States (2002).

Pontsler, A.V., et al., "Cyclooxygenase-2 is induced in monocytes by peroxisome proliferator activated receptor gamma and oxidized alkyl phospholipids from oxidized low density lipoprotein," *J. Biol. Chem.* 277(15):13029-36, The American Society for Biochemistry and Molecular Biology, United States (2002).

Shaw, P.X., et al., "Natural antibodies with the T15 idiotype may act in atherosclerosis, apoptotic clearance, and protective immunity," *J. Clin. Invest.* 105(12):1731-1740, American Society for Clinical Investigation, United States (2000).

Smal, M.A., et al., "Production of antibodies to platelet activating factor," *Mol. Immunol.* 26(8):711-19, Pergamon Press, England (1989).

"Study to Assess VB-201 in Patients with Psoriasis," accessed at: http://clinicaltrialsfeeds.org/clinical-trials/show/NCT01001468, on Oct. 2, 2012.

Subbanagounder, G., et al. "Evidence That Phospholipid Oxidation Products and/or Platelet-Activating Factor Play an Important Role in Early Atherogenesis: In Vitro and In Vivo Inhibition by WEB 2086," *Circulation Research* 85:311-318, American Heart Association, United States (1999).

Subbanagounder, G., et al. "Determinants of Bioactivity of Oxidized Phospholipids: Specific Oxidized Fatty Acyl Groups at the SN-2 Position," *Arteriosclerosis Thromb Vasc. Biol.* 2248-2254, American Heart Association, United States (2000).

Sun, M., et al., "Novel bioactive phospholipids: practical total syntheses of products from the oxidation of archidonic and linoleic esters of 2-lysophosphatidylcholine," *J Org. Chem.* 67(11):3575-84, American Chemical Society, United States (2002).

Tokumura, A., et al. "Cardiovascular Effects of Lysophosphatidic Acid and Its Structural Analogs in Rats," *The Journal of Pharmacology and Experimental Therapeutics* 219:219-224, The American Society of Pharmacology and Experimental Therapeutics, United States (1981).

Wang, C.J. and Tai, H.H., "A facile synthesis of an aldehydic analog of platelet activating factor and its use in the production of specific antibodies," *Chem Phys. Lipids* 55(3):265-73, Elsevier Science Ireland Ltd., Ireland (1990).

Watson et al. "Structural Identification by Mass Spectrometry of Oxidized Phospholipids in Minimally Oxidized Low Density Lipoprotein That Induce Monocyte/Endothelial Interactions and Evidence for their Presence in Vivo," *J. Biol. Chem.* 272(21):13597-13607, The American Society for Biochemistry and Molecular Biology, Inc., United States (1997).

English language abstract of CH642665 A5, espacenet database, Worldwide, published Apr. 30, 1984.

English language abstract of JP 60-104066, espacenet database, Worldwide, published Jun. 8, 1985.

English language abstract of JP 62-000094 A, espacenet database, Worldwide, published Jan. 6, 1987.

English language abstract of JP 62-030714 A, espacenet database, Worldwide, published Feb. 9, 1987.

English language abstract of JP 63-054386 A, espacenet database, Worldwide, published Mar. 8, 1988.

English language abstract of JP 63-135395 A, espacenet database, Worldwide, published Jun. 7, 1988.

English language abstract of ES 2 019 552 A6, espacenet database, Worldwide, published Jun. 16, 1991.

English language abstract of JP 11-116563 A, espacenet database, Worldwide, published Apr. 27, 1999.

International Search Report and Written Opinion dated Aug. 24, 2006 from the International Searching Authority Re.: Application No. PCT/IL05/00735.

International Search Report and Written Opinion dated Mar. 13, 2009 from the International Searching Authority Re.: Application No. PCT/IL08/000013.

International Search Report and Written Opinion dated Apr. 18, 2011 from the International Searching Authority Re.: Application No. PCT/IL11/00008.

International Search Report and Written Opinion dated Apr. 18, 2011 from the International Searching Authority Re.: Application No. PCT/IL11/00010.

International Search Report and Written Opinion dated Apr. 18, 2011 from the International Searching Authority Re.: Application No. PCT/IL11/00012.

International Search Report and Written Opinion dated Jul. 11, 2002 and Aug. 12, 2003, respectively, from the International Searching Authority Re.: Application No. PCT/IL01/01080.

International Search Report and Written Opinion dated Nov. 23, 2004 from the International Searching Authority Re.: Application No. PCT/IL2004/000453.

International Search Report and Written Opinion dated Mar. 24, 2010 from the International Searching Authority Re.: Application No. PCT/IL2009/001049.

International Search Report and Written Opinion dated Apr. 6, 2010 from the International Searching Authority Re.: Application No. PCT/IL09/00949.

International Preliminary Report on Patentability dated Jan. 9, 2007 from the International Bureau of WIPO Re.: Application No. PCT/IL05/00735.

International Preliminary Report on Patentability dated Oct. 20, 2009 from the International Bureau of WIPO Re.: Application No. PCT/IL08/000013.

International Preliminary Report on Patentability dated Apr. 12, 2011 from the International Bureau of WIPO Re.: Application No. PCT/IL2009/000949.

International Preliminary Report on Patentability dated Apr. 9, 2005 from the International Bureau of WIPO Re.: Application No. PCT/IL2004/000453.

International Preliminary Report on Patentability dated May 10, 2011 from the International Bureau of WIPO Re.: Application No. PCT/IL2009/001049.

International Preliminary Report on Patentability dated Jan. 6, 2005 from the International Preliminary Examining Authority Re.: Application No. PCT/IL01/01080.

International Preliminary Report on Patentability dated Jul. 10, 2012 from the International Bureau of WIPO Re.: Application No. PCT/IL11/00012.

International Preliminary Report on Patentability dated Jul. 10, 2012 from the International Bureau of WIPO Re.: Application No. PCT/IL11/00010.

International Preliminary Report on Patentability dated Jul. 10, 2012 from the International Bureau of WIPO Re.: Application No. PCT/IL11/00008.

European Search Report and European Search Opinion dated Feb. 3, 2012 from the European Patent Office Re.: Application No. 11189562.9.

Supplementary Partial European Search Report and European Search Opinion dated Nov. 30, 2009 from the European Patent Office Re.: Application No. 05 75 8938.4.

Supplementary Partial European Search Report dated Mar. 25, 2011 from the European Patent Office Re.: Application No. 08 70 0247.3.

Supplementary European Search Report dated Aug. 3, 2009 from the European Patent Office Re.: Application No. 01997274.4.

Supplementary Partial European Search Report dated Aug. 5, 2009 from the European Patent Office Re.: Application No. 04735088.9.

Supplementary European Search Report and European Search Opinion dated Mar. 9, 2012 from the European Patent Office Re.: Application No. 09824498.1.

(56) References Cited

OTHER PUBLICATIONS

Supplementary European Search Report and European Search Opinion dated Oct. 16, 2012 from the European Patent Office Re.: Application No. 12 178 298.1.
Notice of Allowance dated Jun. 10, 2010 from the US Patent and Trademark Office Re.: U.S. Appl. No. 11/650,973.
Office Action dated Dec. 1, 2009 from the US Patent and Trademark Offie Re.: U.S. Appl. No. 11/650,973.
Office Action dated May 14, 2009 from the US Patent and Trademark Office Re.: U.S. Appl. No. 11/650,973.
Office Action dated Aug. 19, 2008 from the US Patent and Trademark Office Re.: U.S. Appl. No. 11/650,973.
Notice of Allowance dated Oct. 26, 2011 from the US Patent and Trademark Office Re.: U.S. Appl. No. 12/861,921.
Office Action dated Mar. 17, 2011 from the US Patent and Trademark Office Re.: U.S. Appl. No. 12/861,921.
Notice of Allowance dated Jan. 24, 2011 from the US Patent and Trademark Office Re.: U.S. Appl. No. 12/588,371.
Office Action dated Aug. 23, 2010 from the US Patent and Trademark Office Re.: U.S. Appl. No. 12/588,371.
Office Action dated May 28, 2010 from the US Patent and Trademark Office Re.: U.S. Appl. No. 12/588,371.
Notice of Allowance dated Nov. 3, 2010 from the US Patent and Trademark Office Re.: U.S. Appl. No. 10/567,543.
Office Action dated Jun. 15, 2010 from the US Patent and Trademark Office Re.: U.S. Appl. No. 10/567,543.
Office Action dated Mar. 9, 2010 from the US Patent and Trademark Office Re.: U.S. Appl. No. 10/567,543.
Notice of Allowance dated May 25, 2006 from the US Patent and Trademark Office Re.: U.S. Appl. No. 10/718,596.
Final Office Action dated Mar. 2, 2006 from the US Patent and Trademark Office Re.: U.S. Appl. No. 10/718,596.
Office Action dated Jul. 15, 2005 from the US Patent and Trademark Office Re.: U.S. Appl. No. 10/718,596.
Corrected Notice of Allowance dated Jul. 23, 2009 from the US Patent and Trademark Office Re.: U.S. Appl. No. 11/528,657.
Notice of Allowance dated Jun. 30, 2009 from the US Patent and Trademark Office Re.: U.S. Appl. No. 11/528,657.
Office Action dated Nov. 25, 2008 from the US Patent and Trademark Office Re.: U.S. Appl. No. 11/528,657.
Notice of Allowance dated Nov. 3, 2008 from the US Patent and Trademark Office Re.: U.S. Appl. No. 11/183,884.
Office Action dated Apr. 16, 2008 from the US Patent and Trademark Office Re.: U.S. Appl. No. 11/183,884.
Office Action dated Dec. 7, 2007 from the US Patent and Trademark Office Re.: U.S. Appl. No. 11/183,884.
Notice of Allowance dated Oct. 18, 2010 from the US Patent and Trademark Office Re.: U.S. Appl. No. 12/371,930.
Office Action dated Feb. 24, 2010 from the US Patent and Trademark office Re.: U.S. Appl. No. 12/371,930.
Office Action dated May 27, 2010 from the US Patent and Trademark Office Re.: U.S. Appl. No. 12/371,930.
Notice of Allowance dated Dec. 15, 2011 from the US Patent and Trademark Office Re.: U.S. Appl. No. 12/985,365.
Notice of Allowance dated Dec. 12, 2011 from the US Patent and Trademark Office Re.: U.S. Appl. No. 12/985,365.
Office Action dated Aug. 5, 2011 from the US Patent and Trademark Office Re.: U.S. Appl. No. 12/985,365.
Notice of Allowance dated Jul. 2, 2004 from the US Patent and Trademark Office Re.: U.S. Appl. No. 10/445,347.
Office Action dated Jan. 7, 2004 from the US Patent and Trademark Office Re.: U.S. Appl. No. 10/445,347.
Office Action dated Nov. 14, 2003 from the US Patent and Trademark Office Re.: U.S. Appl. No. 10/445,347.
Office Action dated Jun. 12, 2012 from the US Patent and Trademark Office Re.: U.S. Appl. No. 3/358,573.
Notice of Allowance dated Oct. 31, 2012 from the US Patent and Trademark Office Re.: U.S. Appl. No. 13/085,542.
Office Action dated Mar. 16, 2012 from the US Patent and Trademark Office Re.: U.S. Appl. No. 13/085,542.
International Search Report dated Sep. 1, 2011 from the International Searching Authority Re: Application No. PCT/IL11/00007.
International Search Report dated May 20, 2011 from the International Searching Authority Re: Application No. PCT/IL11/00009.
International Preliminary Report on Patentability dated Jul. 10, 2012 from the International Bureau for WIPO Re: Application No. PCT/IL2011/000007.
International Preliminary Report on Patentability dated Jul. 10, 2012 from the International Bureau for WIPO Re: Application No. PCT/IL2011/000009.
International Search Report dated Nov. 13, 2012 from the European Patent Office Re: Application No. PCT/US2012/053533.
Paimela, L., et al., "Clinical significance of antibodies against oxidised low density lipoprotein in early RA," *Ann. Rheum. Dis.* 55(8):558-559, H.K. Lewis, England (1996).
Onorato, J.M., et al., "Immunohistochemical and ELISA assays for Biomarkers of Oxidative Stress in Aging and Disease," *Ann. N. Y. Acad. Sci.* 854:277-290, Blackwell, United States (1998).
Sawai, T., et al., "The effect of phospholipids and fatty acids on tight-junciton permeability and bacterial translocation," *Pediatr. Surg. Int.* 17(4):269-274, Springer-Verlag, Germany (2011).
Noguchi, S., et al., "Effect of Extracellular Phosphatidylinositol on C-MYC Gene-Expressed Human Renal Cancer Cell Line," *Biochem. Biophys. Res. Commun.* 182(2):644-65, Academic Press, United States (1992).
Lombardin, P., et al., "Study of thixotropic bases for the filling of hard capsules," *S.T.P. Pharma Sciences* 10(6):429-437, Editions de Santé, France (2000).
Notice of Allowance dated Mar. 8, 2013 From the U.S. Patent and Trademark Office Re: U.S. Appl. No. 13/085,542, filed Apr. 13, 2011.
Office Action dated Mar. 25, 2013 from the U.S. Patent and Trademark Office Re: U.S. Appl. No. 13/672,811, filed Nov. 9, 2012.
Office Action dated Mar. 15, 2013 from the US Patent and Trademark Office Re: U.S. Appl. No. 13/122,766, filed Apr. 6, 2011.
U.S. Appl. No. 13/792,633, filed Mar. 11, 2013, inventors Sher, N., et al. (now patented).
U.S. Appl. No. 13/709,198, filed Dec. 10, 2012, inventors Halperin, G. and Kovalevski-Ishai, E. (now patented).
U.S. Appl. No. 13/796,654, filed Mar. 12, 2013, inventors Halperin, G. and Kovalevski-Ishai, E. (now patented).
U.S. Appl. No. 13/833,940, filed Mar. 15, 2013, inventors Halperin, G. and Kovalevski-Ishai, E. (now patented).
U.S. Appl. No. 13/828,883, filed Mar. 14, 2013, inventors Kovalevski-Ishai, E., et al. (now patented).
U.S. Appl. No. 13/828,643, filed Mar. 14, 2013, inventors Cohen Y., et al. (now patented).
Bochkov, V.N., et al., "Protective role of phospholipid oxidation products in endotoxin induced tissue damage," *Nature*, 419:77-81, Nature Publishing Group, England (Sep. 2002).
Office Action dated Jan. 16, 2013 from the US Patent and Trademark Office Re: U.S. Appl. No. 13/431,262, filed Mar. 27, 2012.
Notice of Allowance dated Jun. 12, 2013 from the US Patent and Trademark Office Re: U.S. Appl. No. 13/431,262, filed Mar. 27, 2012.
English language abstract for JP50004040 A, Derwent World Patents Index, Dialog File No. 351, Accession No. 849902, Accessed on Mar. 25, 2013.
Langan, R.C., et al., "Ulcerative colitis: diagnosis and treatment," *Am. Fam. Physician* 76(9):1323-30, American Academy of Family Physicians, United States (2007).
Anand, S.S. and Yusuf, S., "C-reactive protein is a bystander of cardiovascular disease," *Eur. Heart. J.* 31(17),2092-2097, Oxford University Press, England (2010).
Office Action dated Apr. 10, 2013 from the US Patent and Trademark Office Re: U.S. Appl. No. 13/520,713, filed Jul. 5, 2012.
"Guidance for Industry: Estimating the Maximum Safe Starting Dose in Initial Clinical Trials for Therapeutics in Adult Healthy Volunteers," U.S. Department of Health and Human Services, Food and Drug Administration, Center for Drug Evaluation and Research, pp. 1-27 (Jul. 2005).

(56) References Cited

OTHER PUBLICATIONS

Office Action dated Aug. 30, 2013 from the US Patent and Trademark Office Re: U.S. Appl. No. 13/828,643, filed Mar. 14, 2013.
Office Action dated Aug. 7, 2013 from the US Patent and Trademark Office Re: U.S. Appl. No. 13/520,713, § 371(c) date: Jul. 5, 2012.
Office Action dated Aug. 22, 2013 from the US Patent and Trademark Office Re: U.S. Appl. No. 13/709,198, filed Dec. 10, 2012.
Office Action dated Aug. 22, 2013 from the US Patent and Trademark Office Re: U.S. Appl. No. 13/796,654, filed Mar. 12, 2013.
Office Action dated Sep. 16, 2013 from the US Patent and Trademark Office Re: U.S. Appl. No. 13/833,940, filed Mar. 15, 2013.
Bhattacharyya, S., et al., "Toll-Like Receptor 4 Signaling Augments Transforming Growth Factor-β Responses: A Novel Mechanism for Maintaining and Amplifying Fibrosis Scleroderma" *The American Journal of Pathology* 182(1):192-205, Elsevier Inc., United States (2013).
Csak, T., et al., "Deficiency in myeloid differentiation factor-2 and toll-like receptor 4 expression attenuates nonalcoholic steatohepatitis and fibrosis in mice," *Am J Physiol Gastrointest Liver Physiol* 300:G433-G441, American Physiological Society, United States (2011).
Franklin, C., et al., "Design, Synthesis, and Evaluation of Water-Soluble Phospholipid Analogues as Inhibitors of Phospholipase C from *Bacillus cereus,*" *Journal of Organic Chemistry* 68(19):7298-7307, American Chemical Society, United States (2003), Caplus AN 2003:643618.
Herre, J., et al., "Allergens as Immunomodulatory Proteins: The Cat Dander Protein Fel d 1 Enhances TLR Activation of Lipid Ligands," *J Immunol* 191:1529-1535, American Association of Immunologists, Inc., United States (2013).
Kwok, S-K., et al., "TLR2 litigation induces the production of IL-23/IL-17 via IL-6, STAT3 and NF-kB pathway in patients with primary Sjorgren's syndrome," *Arthritis Research & Therapy* 14(R64):1-13, BioMed Central, England (2012).
Lartigue, A., et al., "Critical Role of TLR2 and TLR4 in Autoantibody Production and Glomerulonephritis in lpr Mutation-Induced Mouse Lupus," *J Immunol* 183:6207-6216, American Association of Immunologists, Inc., United States (2009).
Li, J., et al., "Toll-like receptors as therapeutic targets for autoimmune connective tissue diseases," *Pharmacology & Therpeutics* 138:441-451, Pergamon Press, England (2013).
Millien, V.O., et al., "Cleavage of Fibrinogen by Proteinases Elicits Allergic Responses Through Toll-Like Receptor 4," *Science* 341(6147):792-796, American Association for the Advancement of Science, United States (2013).
Miura, K., et al., "TLR2 and palmitic acid cooperatively contribute to the development of nonalcoholic steatohepatitis through inflammasome activation," *Hepatology* 57(2):577-589, Wiley, United States (2013).
Wen, Z., et al., "Autoantibody Induction by DNA-Containing Immune Complexes Requires HMGB1 with the TLR2/MicroRNA-155 Pathaway," *J Immunol* 190:5411-5422, American Association for the Advancement of Science, United States (2013).
Office Action dated Mar. 7, 2014, in U.S. Appl. No. 13/833,940, Halperin, G. and Kovalevski-Ishai, E., filed Mar. 15, 2013.
Office Action dated Jul. 16, 2014, in U.S. Appl. No. 13/833,940, Halperin, G. and Kovalevski-Ishai, E., filed Mar. 15, 2013.
Office Action dated Apr. 23, 2014, in U.S. Appl. No. 13/122,766, Breitbart, E., et al., § 371(c) date: Apr. 6, 2011.
Office Action dated Mar. 11, 2014, in U.S. Appl. No. 13/520,713, Cohen, Y., et al., § 371(c) date: Jul. 5, 2012.
Office Action dated Feb. 25, 2014, in U.S. Appl. No. 13/828,643, Cohen, Y., et al., filed Mar. 14, 2013.
Office Action dated Jun. 16, 2014, in U.S. Appl. No. 13/520,719, Cohen, Y., et al., filed Mar. 7, 2013.
International Preliminary Report on Patentability for International Application No. PCT/IB2012/002930, International Bureau of WIPO, Geneva, Switzerland, dated Jun. 17, 2014.
Vascular Biogenics Ltd., operating as VBL Therapeutics, "Study to Assess VB-201 in Patients with Psoriasis," ClinicalTrials.gov, accessed at https://clinicaltrials.gov/ct2/show/NCT01001468?term=VB-201&rank=1, accessed on Aug. 28, 2014, 4 pages.
Vascular Biogenics Ltd., operating as VBL Therapeutics, "A Study to Evaluate the Efficacy and Safety of VB-201 in Patients with Psoriasis," ClinicalTrials.gov, accessed at https://clinicaltrials.gov/ct2/show/NCT01837420?term=VB-201&rank=2, accessed on Aug. 28, 2014, 4 pages.
Vascular Biogenics Ltd., operating as VBL Therapeutics, "Study to Assess the Safety and Efficacy of Multiple Doses of VB-201 on Biomarkers," ClinicalTrials.gov, accessed at https://clinicaltrials.gov/ct2/show/NCT01159730?term=VB-201&rank=3, accessed on Aug. 28, 2014, 2 pages.
Vascular Biogenics Ltd., operating as VBL Therapeutics, "A Study to Evaluate the Efficacy and Safety of VB-201 in Patients with Ulcerative Colitis," ClinicalTrials.gov, accessed at https://clinicaltrials.gov/ct2/show/NCT01839214?term=VB-201&rank=4, accessed on Aug. 28, 2014, 4 pages.
International Search Report and Written Opinion of the International Search Authority, or the Declaration for Int'l Appl. No. PCT/IB12/02930, dated May 21, 2013, U.S. International Searching Authority, Alexandria, Virginia.
International Preliminary Report on Patentability for Int'l Appl. No. PCT/IB12/02930, dated Jun. 26, 2014, International Bureau of WIPO, Geneva, Switzerland.
Final Office Action dated Aug. 26, 2014, in U.S. Appl. No. 13/520,713, Cohen, Y., et al., § 371(c) date: Jul. 5, 2012.
Final Office Action dated Aug. 13, 2014, in U.S. Appl. No. 13/828,643, Cohen, Y., et al., filed Mar. 14, 2013.
Feige, E., et al., "Modified phospholipids as anti-inflammatory compounds," *Curr. Opin. Lipidol.* 21:525-529, Wolters Kluwer Health/Lippincott Williams & Wilkins (2010).
Silva, M.M., et al., "Systemic Inflammatory Reaction After Silicone Breast Implant," *Aesth. Plast. Surg.* 35:789-794, Springer (2011).
Mendel, I., et al., "VB-201, an oxidized phospholipid small molecule, inhibits CD14- and Toll-like receptor-2-dependent innate cell activation and constrains atherosclerosis," *Clin. Exp. Immunol.* 175:126-137, British Society for Immunology (2013).
Office Action dated Mar. 1, 2016, in U.S. Appl. No. 14/364,705, Mendel, I., et al., filed Jun. 12, 2014.
Rivera, C.A., et al., "Toll-like receptor-4-signaling and Kupffer cells play pivotal roles in the pathogenesis of non-alcoholic steatohepatitis," J. Hepatol. 47:571-579, Elsevier (2007).
Pidkovka, N., et al., "POVPC induces the smooth muscle cells inflammatory phenotype," *FASEB J.* 21:599.1, FASEB (2007).
Reagan-Shaw, S., et al., "Dose translation from animal to human studies revisited," *FASEB J.* 22:659-661, FASEB (2007).
Final Office Action dated Mar. 30, 2015, in U.S. Appl. No. 13/520,719, Cohen, Y., et al., filed Mar. 7, 2013.
Final Office Action dated Jan. 15, 2016, in U.S. Appl. No. 13/520,719, Cohen, Y., et al., filed Mar. 7, 2013.
English language abstract of JP58154512, published Sep. 14, 1983.
Ali, M.H., et al., "The role of lipid geometry in designing liposomes for the solubilisation of poorly water soluble drugs," *Int. J. Pharmaceut.* 453. 1:225-232 (2013).
International Search Report and Written Opinion for International Application No. PCT/IB2015/059133, U.S. Patent and Trademark Office, United States, dated Feb. 25, 2016, 9 pages.
Notice of Allowance dated Aug. 29, 2013 from the U.S. Patent and Trademark Office Re: U.S. Appl. No. 13/672,811, filed Nov. 9, 2012.
Office Action dated Sep. 11, 2013, in U.S. Appl. No. 13/122,766, Breitbart, E., et al., § 371(c) date: Apr. 6, 2011.
Notice of Allowance dated Nov. 26, 2014, in U.S. Appl. No. 13/122,766, Breitbart, E., et al., § 371(c) date: Apr. 6, 2011.
Notice of Allowance dated Jan. 29, 2014 from the US Patent and Trademark Office Re: U.S. Appl. No. 13/709,198, filed Dec. 10, 2012.
Notice of Allowance dated Jan. 31, 2014 from the US Patent and Trademark Office Re: U.S. Appl. No. 13/796,654, filed Mar. 12, 2013.

(56) References Cited

OTHER PUBLICATIONS

Notice of Allowance dated Nov. 25, 2014, in U.S. Appl. No. 13/833,940, Halperin, G. and Kovalevski-Ishai, E., filed Mar. 15, 2013.

U.S. Appl. No. 15/430,715, filed Feb. 13, 2017 inventors Halperin G., et al. (not published).

Supplementary European Search Report for Application No. 15863247.1 dated Jan. 3, 2018 from the European Patent Office, 5 pages.

Shi, H., et al., "Chlorogenic acid reduces liver inflammation and fibrosis through inhibition of toll-like receptor 4 signaling pathway," Toxicology 303:107-114, Elsevier B.V., Netherlands (2013).

Huebener, P., et al., "Regulation of wound healing and organ fibrosis by toll-like receptors," Biochimica et Biophysica Acta 1832:1005-1017, Elsevier B.V., Netherlands (2013).

\* cited by examiner

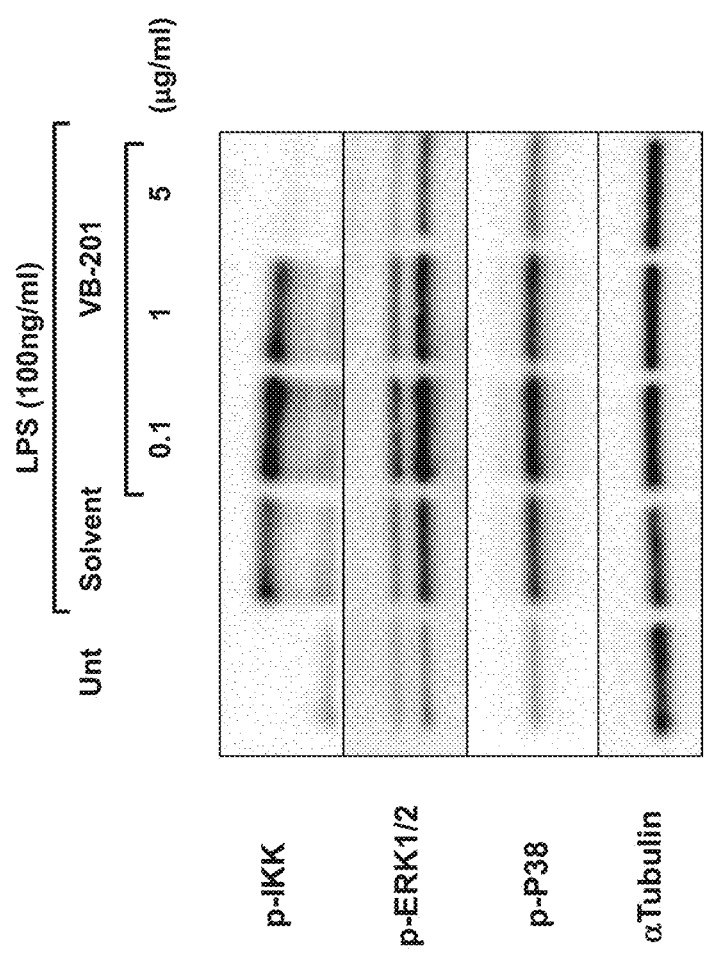

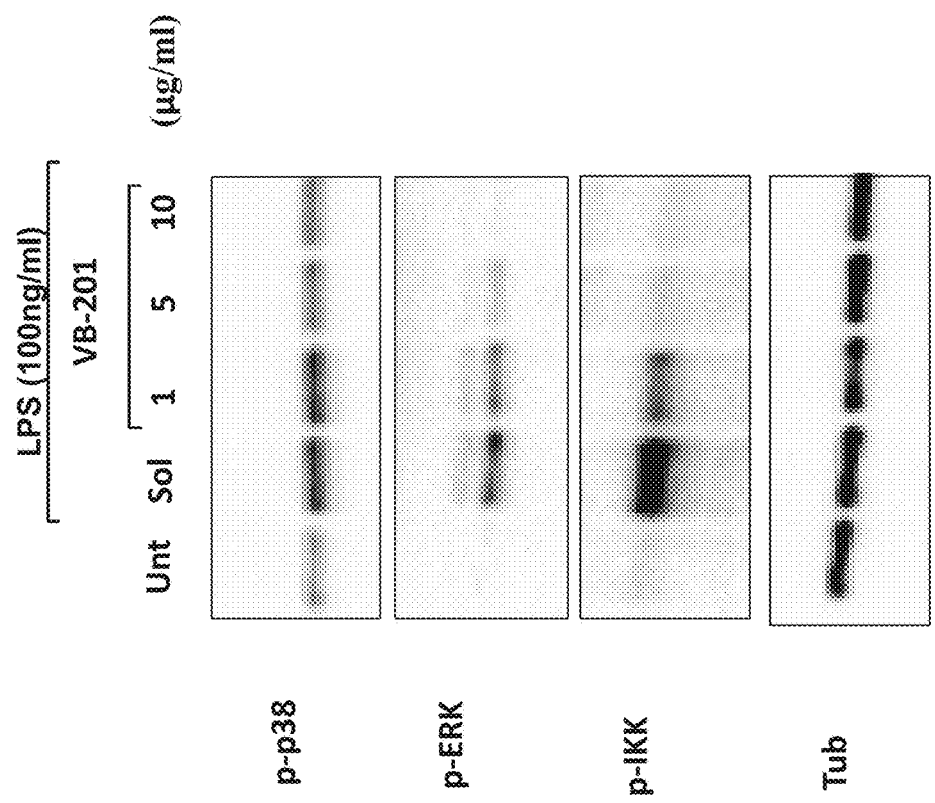

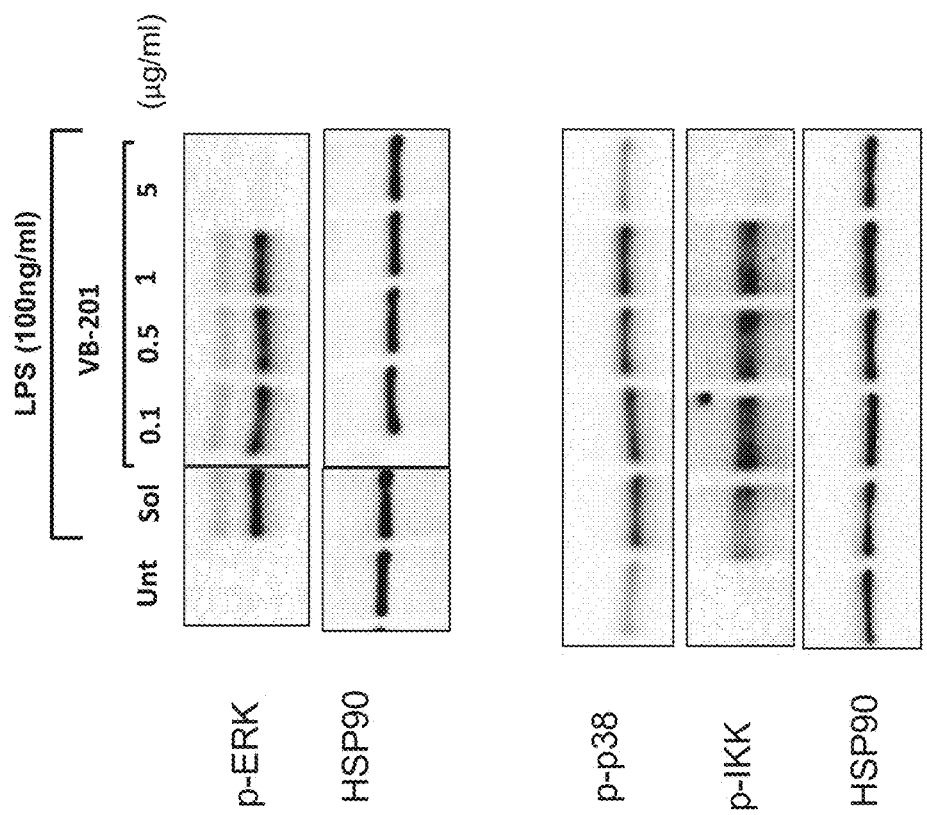

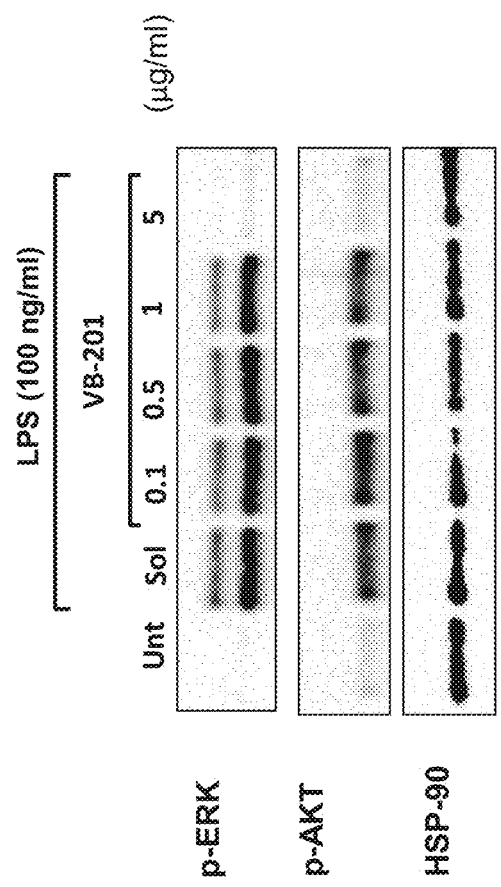

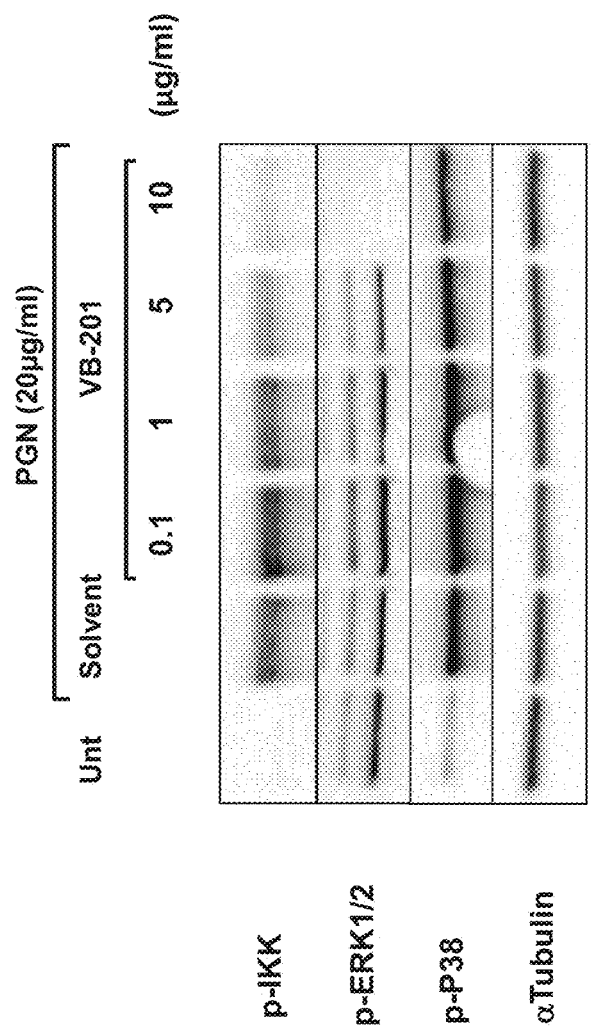

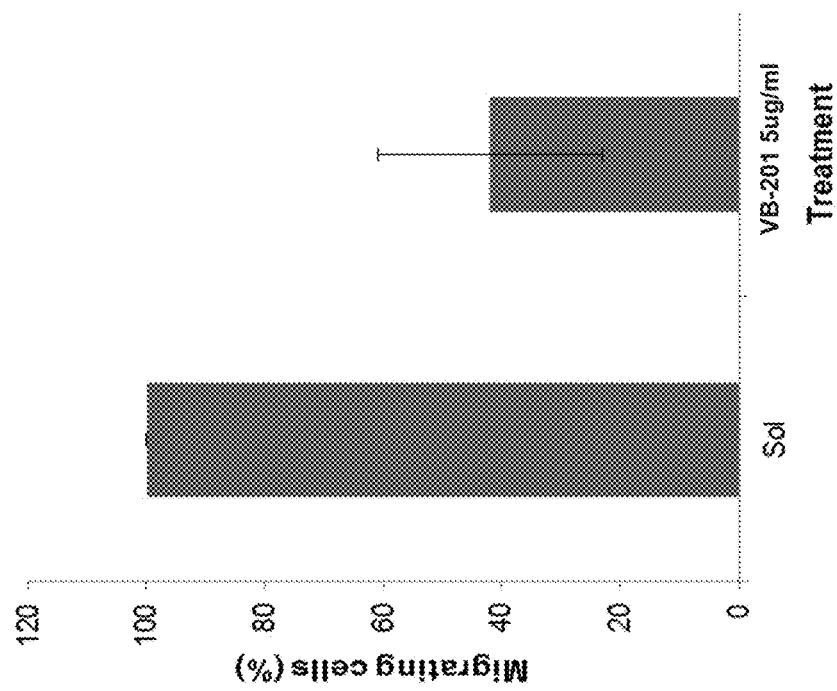

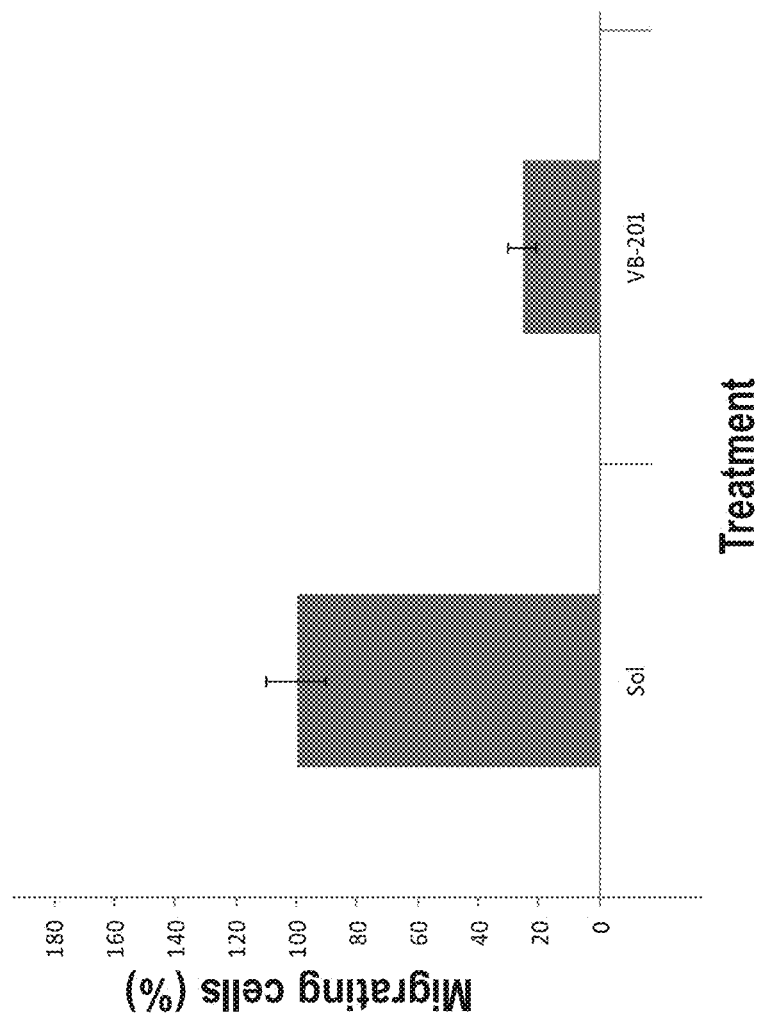

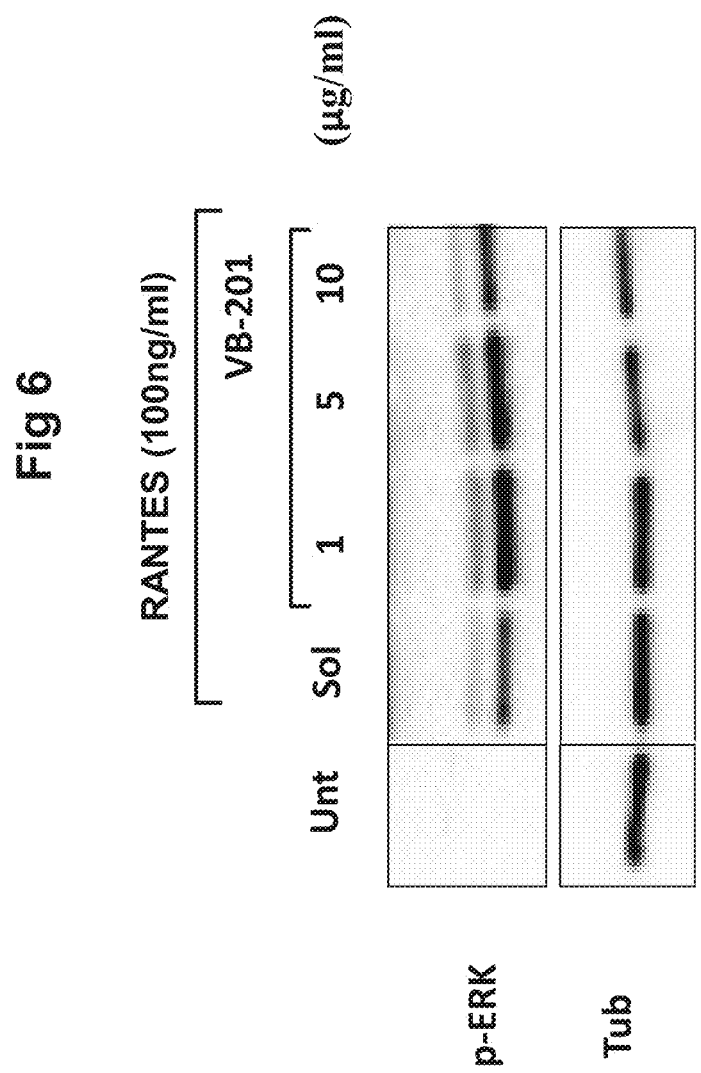

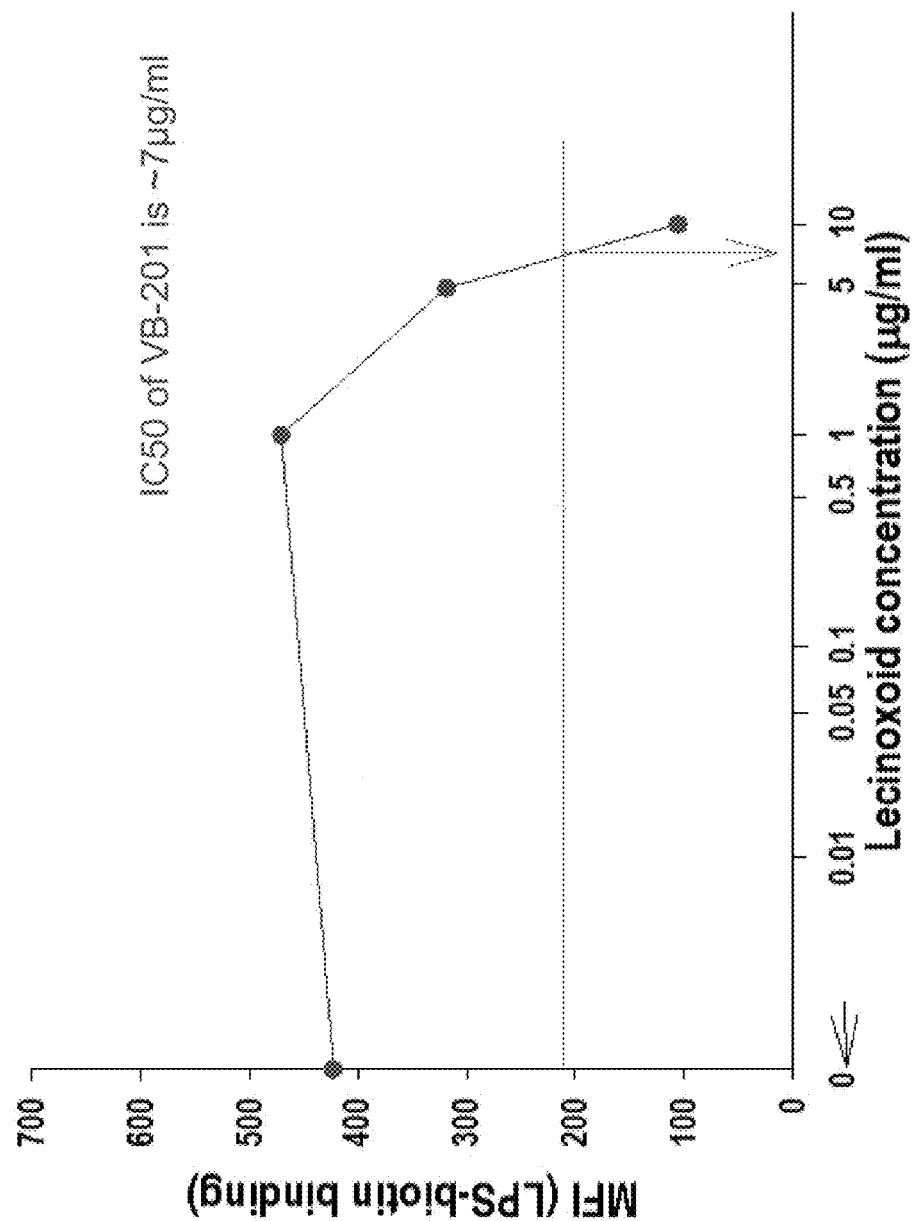

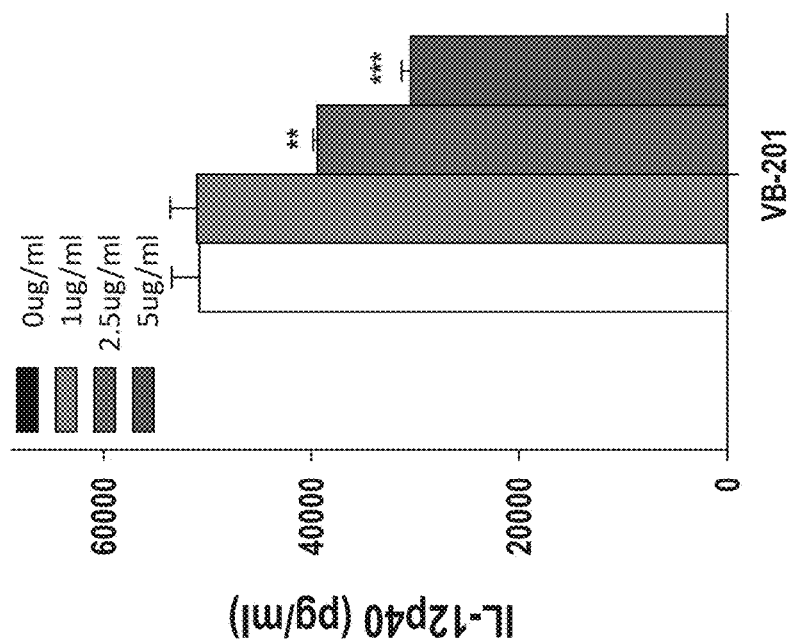

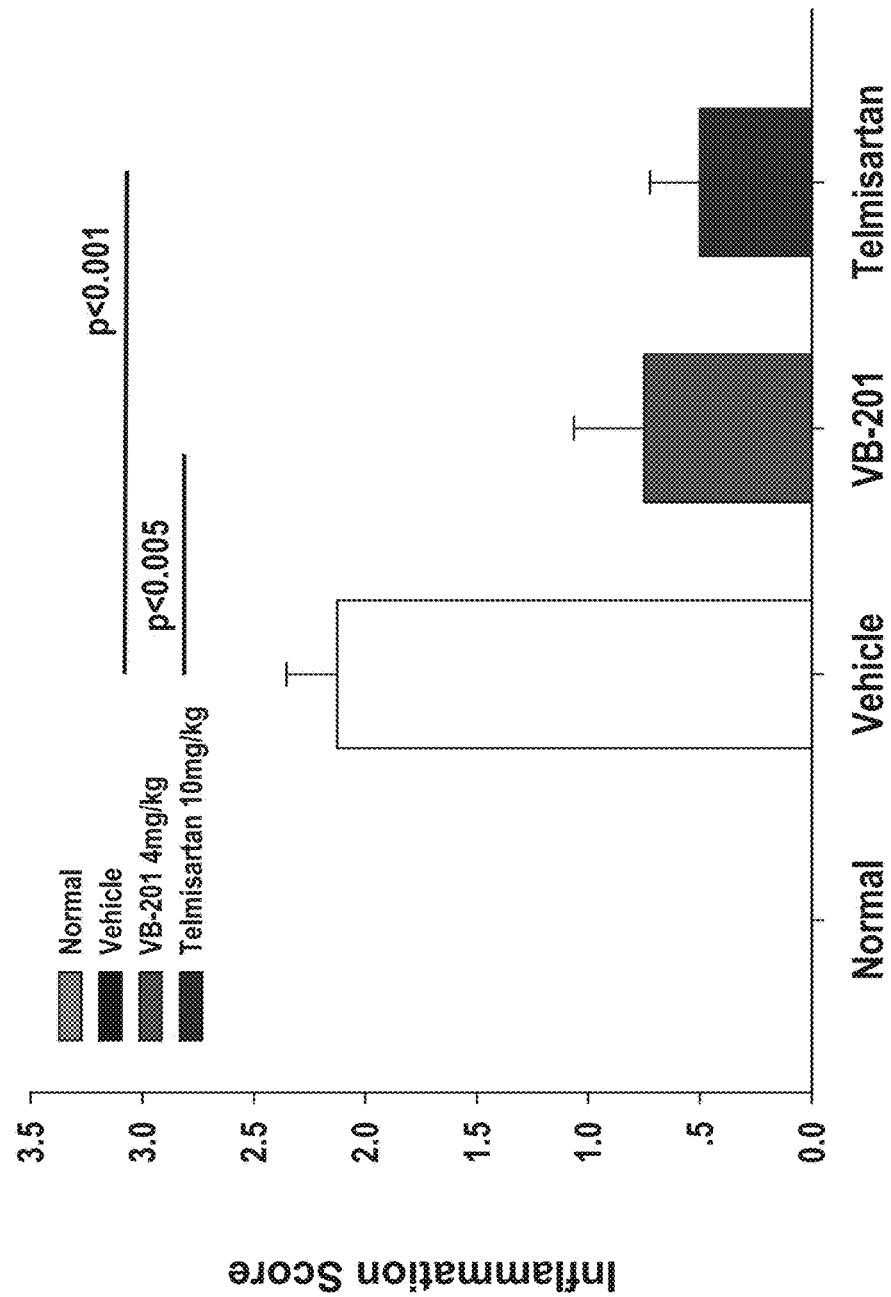

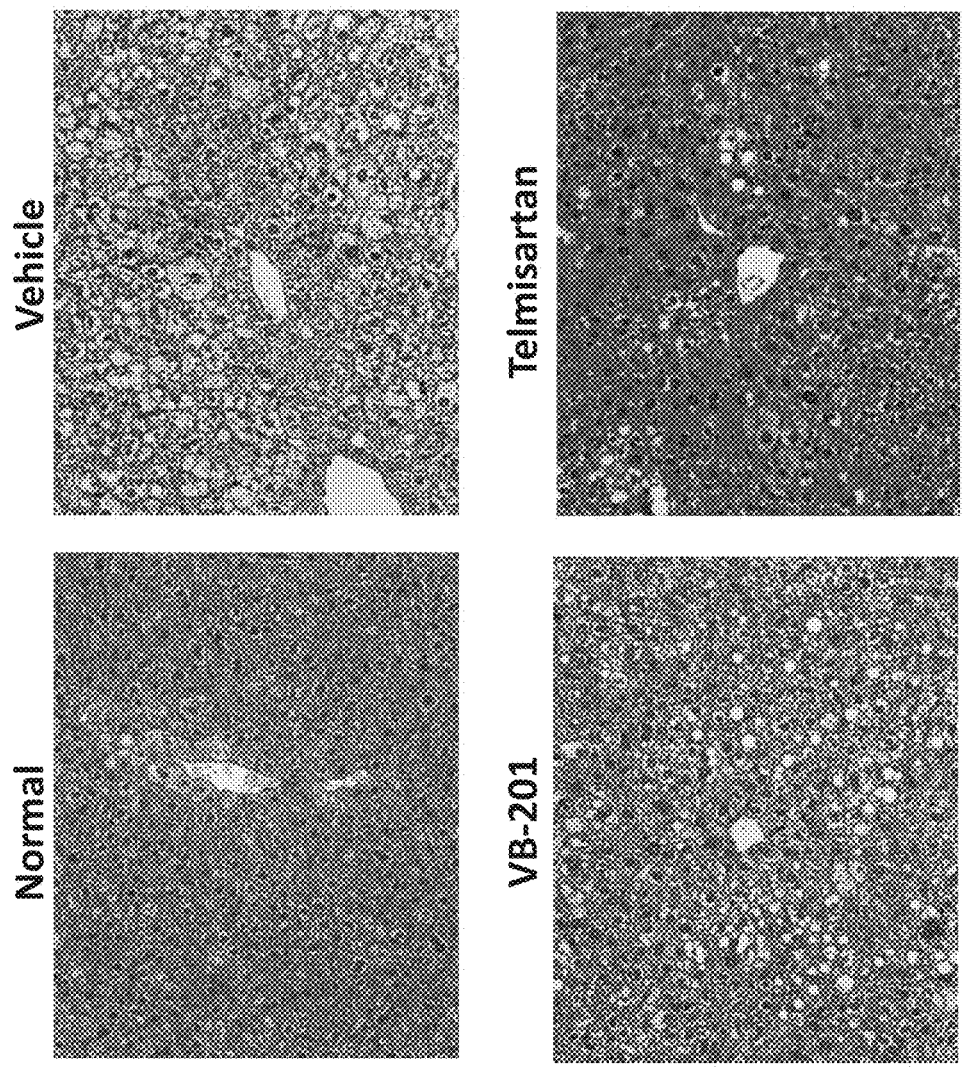

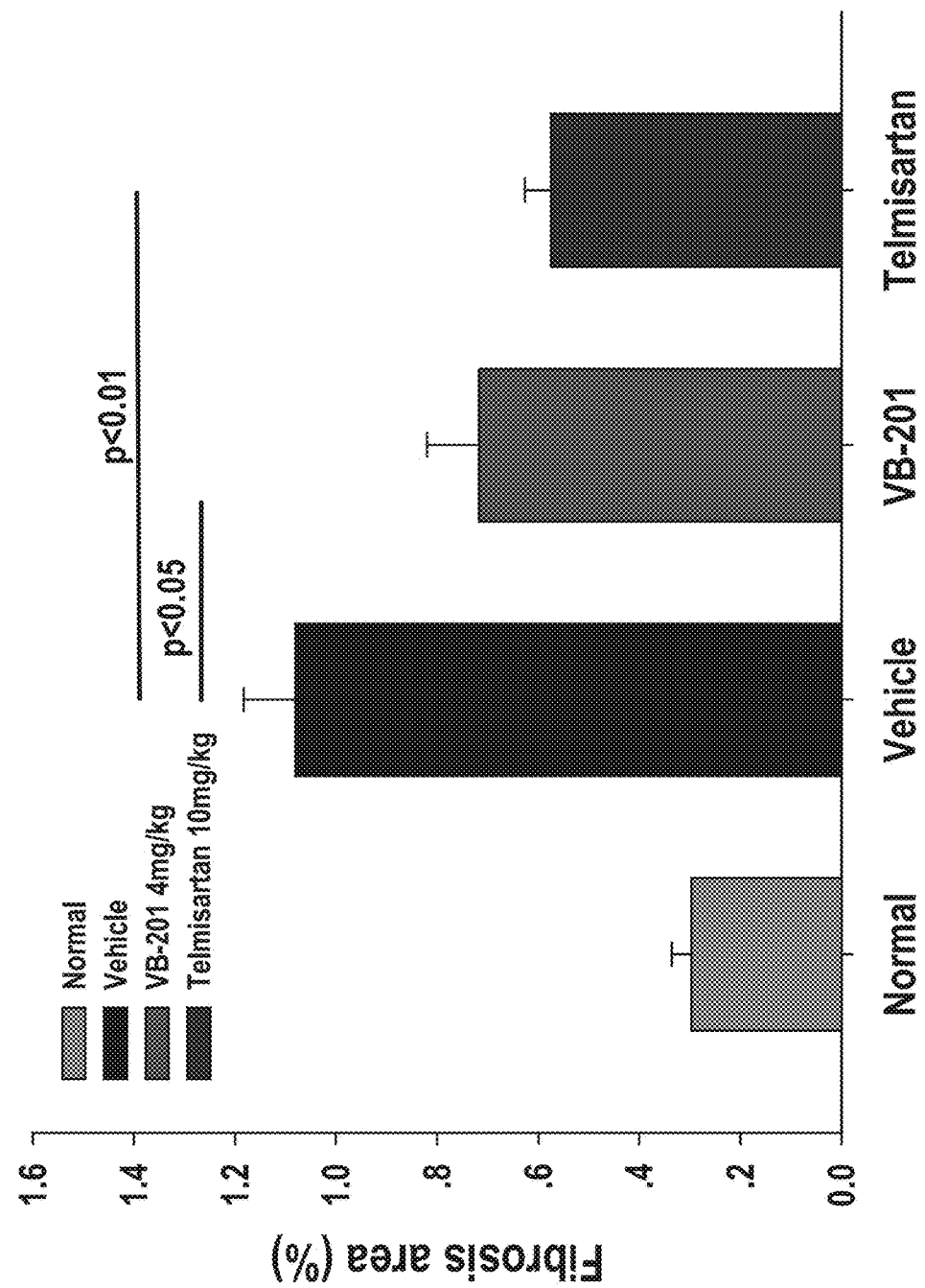

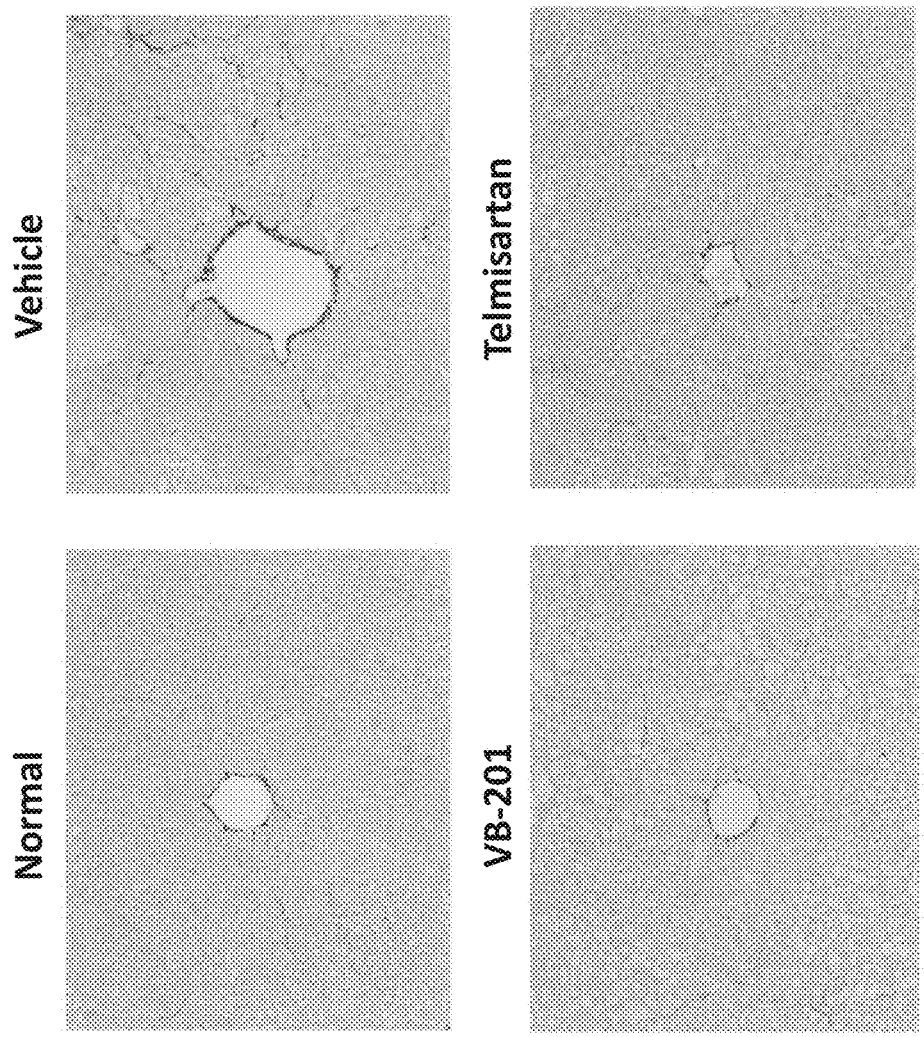

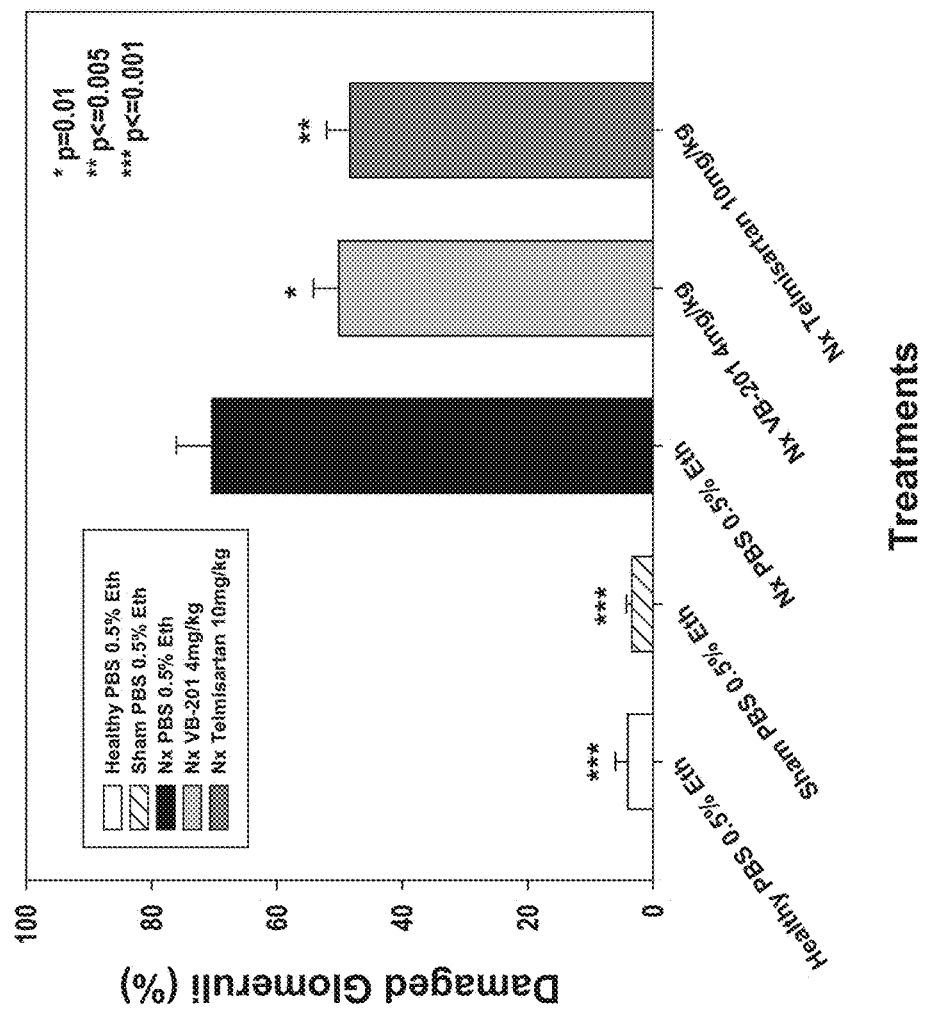

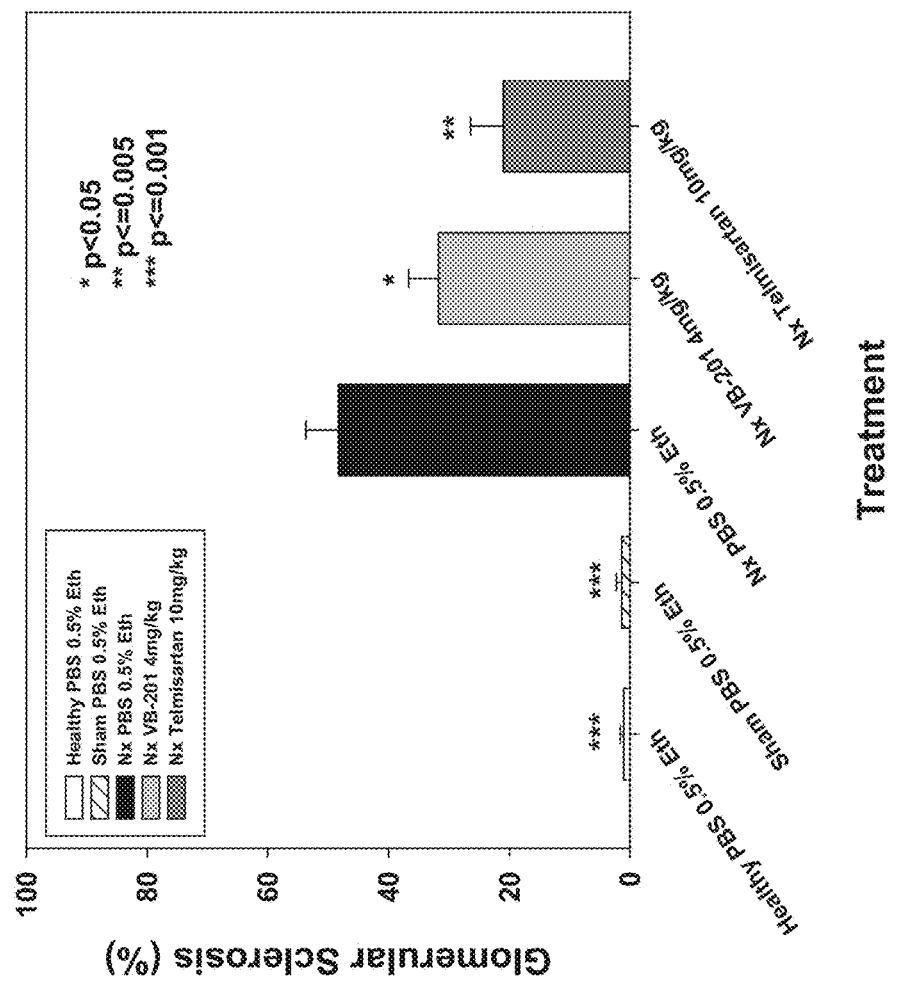

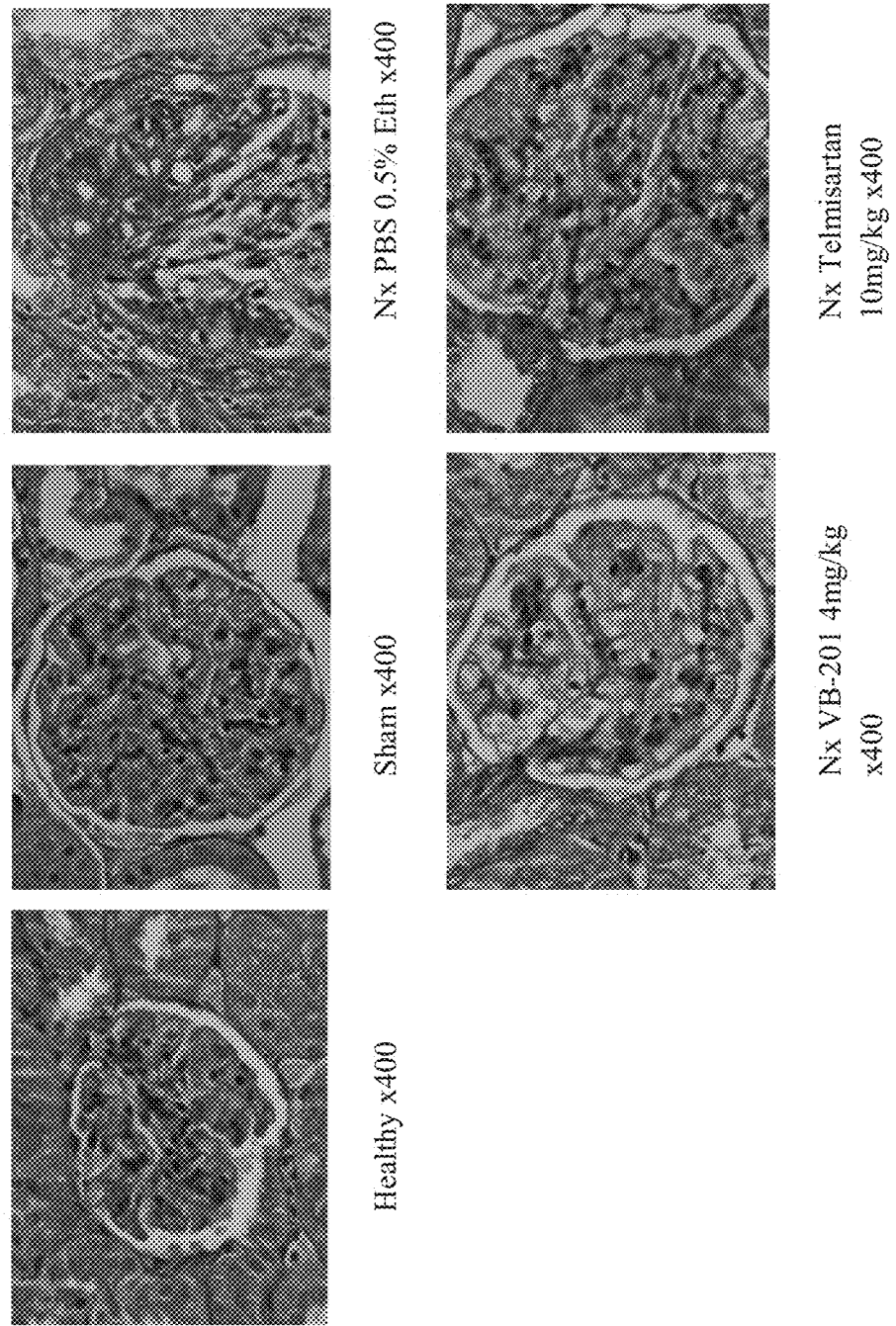

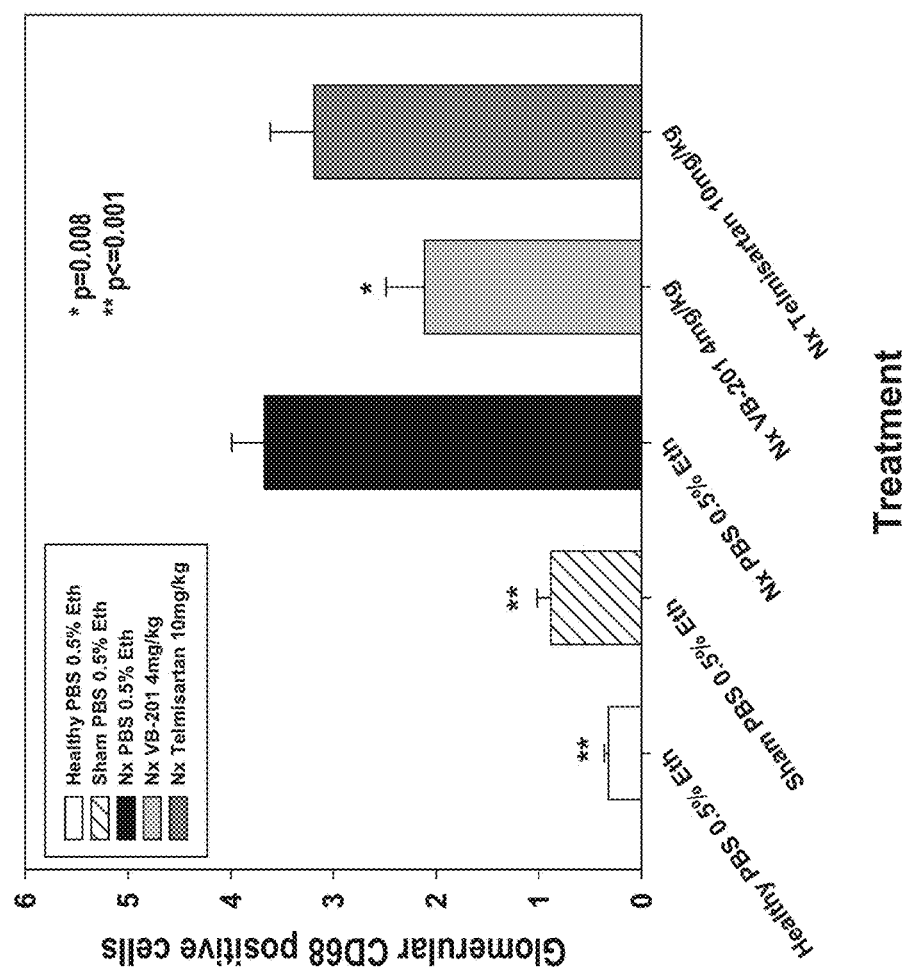

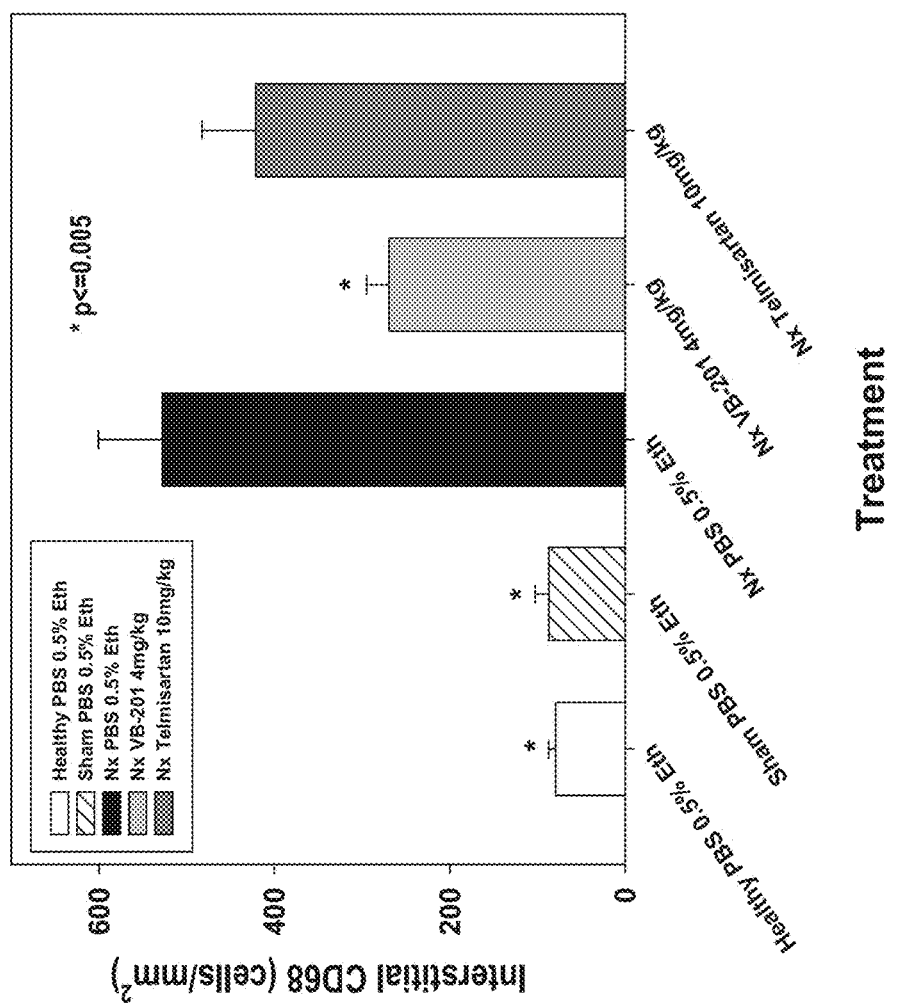

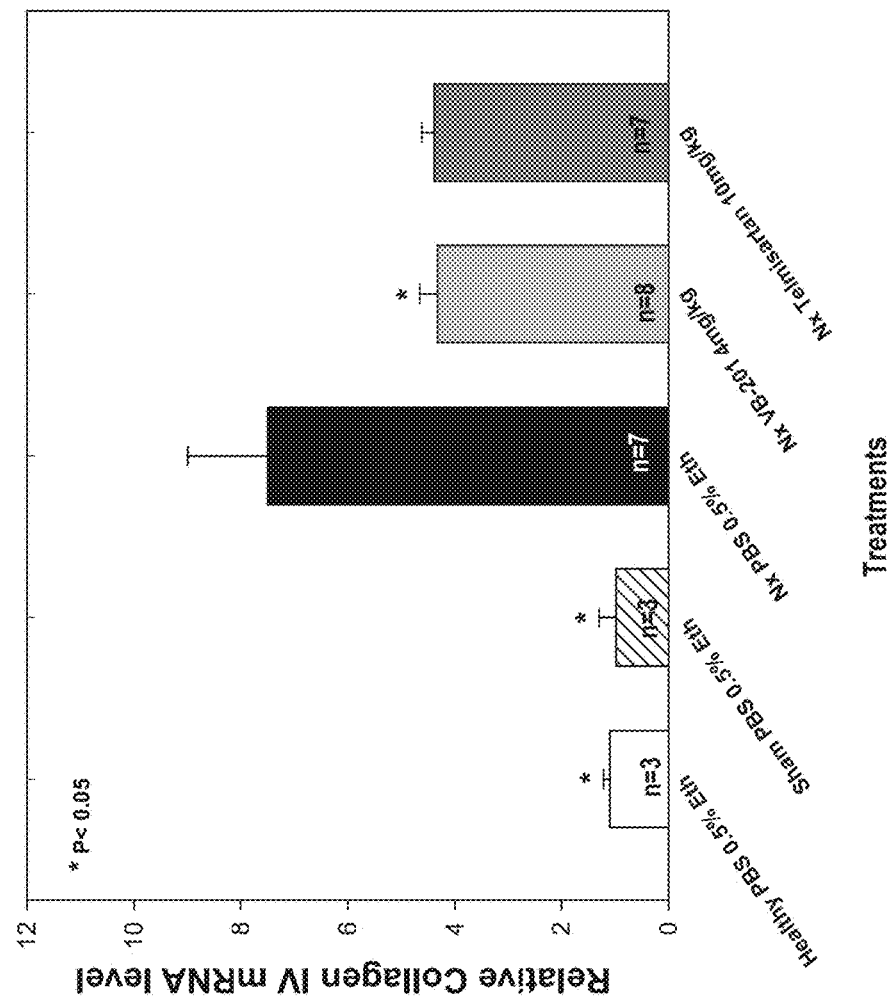

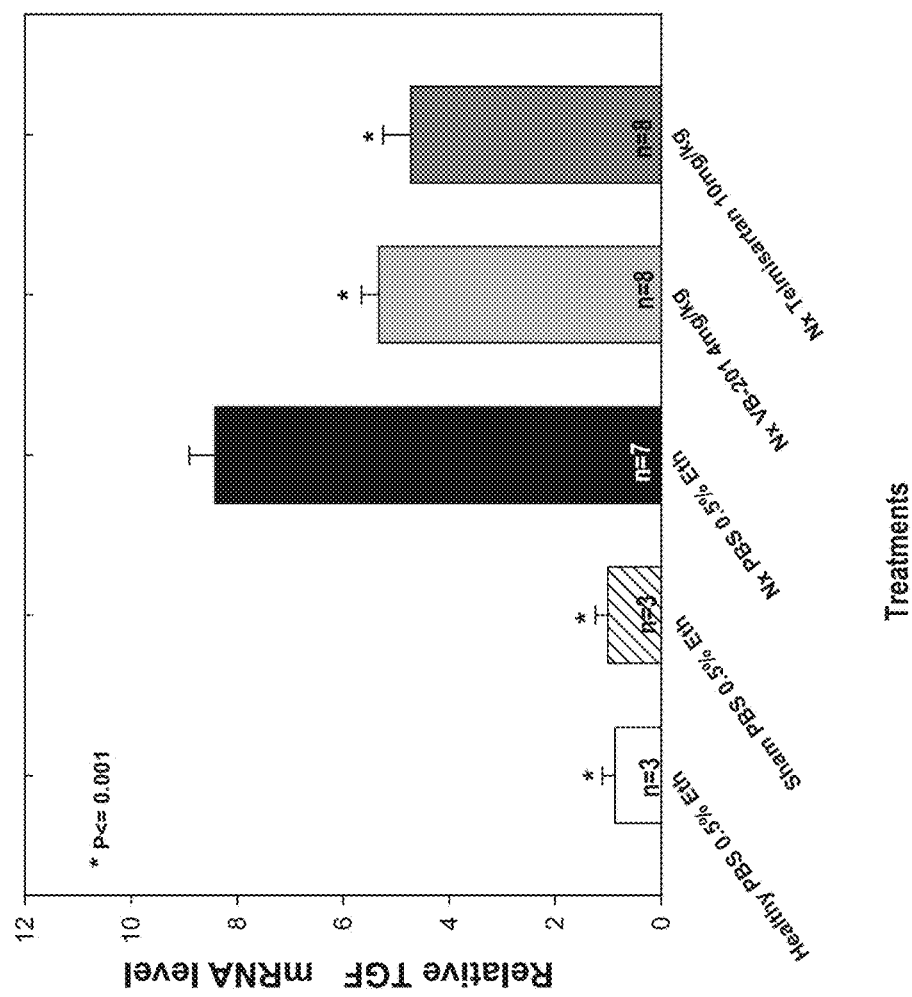

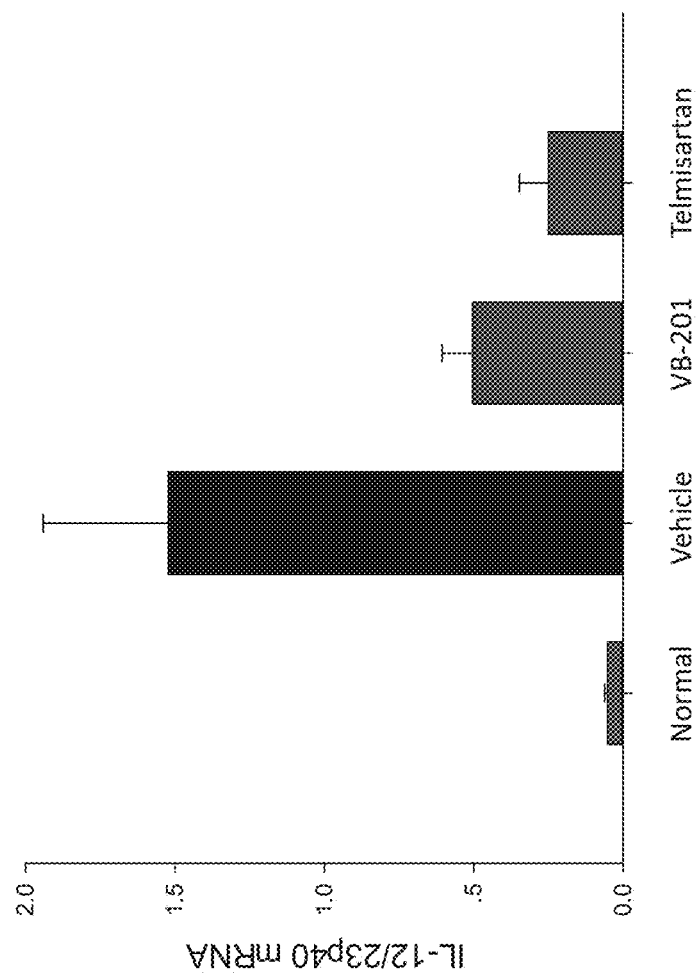

OXIDIZED LIPIDS AND TREATMENT OR PREVENTION OF FIBROSIS

CROSS-REFERENCE TO RELATED APPLICATIONS

This application is a continuation of International Appl. No. PCT/IB2015/059133, filed Nov. 26, 2015, which claims priority benefit to U.S. Provisional Appl. No. 62/085,051, filed Nov. 26, 2014, the contents of both are hereby incorporated by reference in their entireties.

FIELD OF THE INVENTION

The present invention relates to methods of treating or preventing fibrosis with oxidized lipid compounds and pharmaceutical compositions comprising the same.

BACKGROUND OF THE INVENTION

Fibrosis is the formation of excess fibrous connective tissue in an organ or tissue. Fibrosis encompasses the pathological state of excess deposition of fibrous tissue, as well as the process of connective tissue deposition in healing. Fibrosis is similar to the process of scarring, in that both involve stimulated cells (e.g., fibroblasts) laying down connective tissue, including collagen and glycosaminoglycans.

Fibrosis can be considered as a scarring process in response to chronic diseases where excessive extracellular matrix (ECM) deposition leads to irreversible tissue damage and failure or disturbance of proper organ function. The pathophysiology of fibrosis has generally been studied in the context of the particular organ or tissue affected, including lung, kidney, liver, heart and skin. Loss of metabolic homeostasis and chronic low-grade inflammation may play a role in the pathogenesis of fibrosis. Fibrogenesis is a dynamic process and occurs in four phases: i) initiation, due to injury of the organ/tissue; ii) inflammation and activation of effector cells; iii) enhanced synthesis of ECM; and iv) deposition of ECM with progression to end-organ failure.

Fibrosis can occur in many tissues within the body. Examples include pulmonary fibrosis (lungs), idiopathic pulmonary fibrosis (lungs), cystic fibrosis (lungs), progressive massive fibrosis (lungs), liver fibrosis, cirrhosis (liver), steatohepatitis (fatty liver disease), nonalcoholic fatty liver disease (NAFLD), nonalcoholic steatohepatitis (NASH), endomyocardial fibrosis (heart), myocardial infarction (heart), atrial fibrosis (heart), medastinal fibrosis (soft tissue of mediastinum), myelofibrosis (bone marrow), retroperitoneal fibrosis (soft tissue of the retroperitoneum), nephrogenic systemic fibrosis (skin), keloid (skin), Crohn's disease (intestine), scleroderma/systemic sclerosis (skin, lungs), arthrofibrosis (knee, shoulder, other joints), Peyronie's disease (penis), Dupuytren's contracture (hands, fingers), adhesive capsulitis (shoulder), kidney fibrosis, and focal and segmental glomerulosclerosis (kidney).

One of the major complications of insulin resistance and metabolic syndrome is nonalcoholic fatty liver disease (NAFLD), which can progress from fatty liver to liver inflammation (NASH) and liver fibrosis. It is believed that due to intestinal barrier leakage, accompanied by overgrowth and changes in the composition of gut flora, bacterial components travel through the portal vein into the liver, where they encounter toll-like receptors (TLRs).

TLRs are a family of receptors imperative for the innate immune response against microbial invasion. TLRs can be divided into two major subgroups based on their cellular localization. Plasma membrane expressed TLRs include TLR1, TLR2, TLR4, TLR5 and TLR6, whereas the intracellular TLRs include TLR3, TLR7, TLR8 and TLR9. The interaction between TLRs with their cognate agonists instigates a cascade of cues which include recruitment of the adaptor molecules MyD88/TRIF and downstream phosphorylation of MAPK kinases and NF-κB. These events culminate in the secretion of proinflammatory cytokines, including IL-12/23, IL-6 and TNF-α. TLR2 forms a heterodimer with TLR1 which recognizes bacterial triacylated lipopeptides, and a heterodimer with TLR6 which recognizes bacterial diacylated lipopeptides. TLR4 coupled to MD2 in complex with lipopolysaccharide-binding protein (LBP) and the co-receptor CD14 bind lipopolysaccharide (LPS) from gram negative bacteria.

Liver resident kupffer and hepatic stellate cells (HSC) express TLR2 which recognize triacylated lipopeptides from Gram-negative bacteria and *mycoplasma* and diacylated lipopeptides from Gram-negative bacteria and *mycoplasma* and TLR4 and its co-receptor CD14 which recognize lipopolysaccharide (LPS) from gram-negative bacteria. Both TLR2 and TLR4 can also bind to danger associated molecular patterns released from injured tissues. These TLR2 and TLR4 complexes mediate the production of pro-inflammatory cytokines and fibrogenic response by kupffer and stellate cells. Pre-clinical studies showed that nonalcoholic steatohepatitis and liver fibrosis are inhibited in TLR2 and TLR4 deficient mice, indicating its role in disease pathogenesis. In humans, LPS plasma levels are elevated in NAFLD patients and alterations in TLR4 and CD14 genes are associated with risks of developing nonalcoholic steatohepatitis and fibrogenesis.

Monocytes are key players in the immune system, with critical roles in innate and adaptive immunity, immune surveillance and particle scavenging. Whereas a subset of monocytes is "resident" and recruited to tissues independently of inflammatory stimuli to assist in steady-state surveillance, wound-healing and resolution of inflammation, the absolute majority (80-90%) of human circulating monocytes is classified as "inflammatory". These monocytes can sense inflammatory stimuli and quickly migrate through the vascular or lymphatic endothelium to the periphery, where they can differentiate into macrophages and dendritic cells (DCs) which cooperate with additional cell subsets (such as Th1-cells) to promote inflammation. While playing a necessary role in host defense, monocytes were nonetheless identified as critical mediators of several inflammatory diseases, including atherosclerosis, rheumatoid arthritis (RA) and multiple sclerosis (MS). Suppressing the accumulation of unwanted monocytes/macrophages in a chronically inflamed tissue has therapeutic potential, and migration inhibitors have accordingly demonstrated promising anti-inflammatory results in animal models and clinical trials.

Renal fibrosis (kidney fibrosis) is a wound healing/scarring response following kidney injury that occurs in many forms of chronic kidney disease (CKD). Following kidney injury, resident fibroblasts are activated by various pro-inflammatory and pro-fibrotic stimuli. Activated fibroblasts, also called myofibroblasts, produce excessive ECM proteins that accumulate in the interstitium, and therefore are considered a mediator of renal fibrosis. Regardless of the primary insult leading to renal fibrosis, chronic inflammation appears to be a process heralding renal fibrogenesis. Elevated levels of inflammatory markers were associated with an increased risk of developing CKD. Induction of various pro-inflammatory cytokines interleukin (IL)-6, IL-8, IL-10, chemokine (C—C motif) ligand 2 (CCL2), tumor necrosis factor-α (TNF-α) and adhesion molecules (intercellular adhesion molecule-1 and vascular cell adhesion molecule-1) attracted the transmigration of macrophages and T cells from the circulation to the interstitium, thereby further enhancing the inflammatory state. Evidence suggests that TLRs and macrophages are associated with the pathogenesis of renal fibrosis.

Fibrosis can cause severe morbidity and deleterious effects on patients' daily function, activity of daily living (ADL) and quality of life, and can lead to poor prognosis. For example, idiopathic pulmonary fibrosis (IPF) is a chronic intractable disease associated with worsening and debilitating shortness of breath. IPF patients become oxygen dependent, and have an average median survival time of three years and a five year survival rate of 20% to 40% after diagnosis. Therefore, the development of new therapies for fibrosis is needed.

SUMMARY OF THE INVENTION

In some embodiments, the present invention provides methods of treating or preventing fibrosis (e.g., liver fibrosis, kidney fibrosis, focal and segmental glomerulosclerosis, or any other fibrosis described herein), comprising administering to a subject in need thereof a therapeutically effective amount of a compound having a structure according to Formula 1:

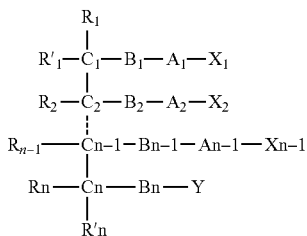

Formula 1 or a pharmaceutically acceptable salt, a hydrate or a solvate thereof, wherein:

n is an integer from 1 to 6, wherein when n is 1, Cn, Bn, Rn, and Y are absent, and $C_1$ is attached to R'n;

each of $B_1, B_2, \ldots Bn-1$ and Bn is independently selected from the group consisting of oxygen, sulfur, nitrogen, phosphorus and silicon, wherein each of said nitrogen, phosphorus and silicon is optionally substituted by one or more substituents selected from the group consisting of alkyl, halo, cycloalkyl, aryl, hydroxy, thiohydroxy, alkoxy, aryloxy, thioaryloxy, thioalkoxy, and oxo;

each of $A_1, A_2, \ldots An-1$ and An is independently selected from the group consisting of CR"R''', C=O and C=S, Y is selected from the group consisting of hydrogen, acyl, alkyl, aryl, cycloalkyl, carboxy, saccharide, phosphoric acid, phosphoryl choline, phosphoryl ethanolamine, phosphoryl serine, phosphoryl cardiolipin, phosphoryl inositol, ethylphosphocholine, phosphorylmethanol, phosphorylethanol, phosphorylpropanol, phosphorylbutanol, phosphoryletha-nolamine-N-lactose, phosphoethanolamine-N-glutaric acid, phosphoethanolamine-N-[methoxy (propylene glycol)], phosphoinositol-4-phosphate, phosphoinositol-4,5-biphosphonate, phosphoinositol-4,5-bisphosphate, pyrophosphate, phosphoethanolamine-diethylenetriamine-pentaacetate, dinitrophenyl-phosphoethanolamine, phosphoglycerol, and a moiety having the general formula:

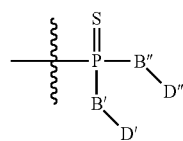

wherein:

each of B' and B" is independently selected from the group consisting of sulfur and oxygen; and each of D' and D" is independently selected from the group consisting of hydrogen, alkyl, amino substituted alkyl, cycloalkyl, phosphonate, and thiophosphonate; and each of $X_1, X_2, \ldots Xn-1$ is independently a saturated or unsaturated hydrocarbon having the general Formula 2:

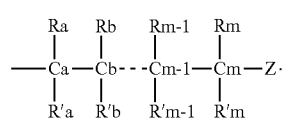

Formula 2 wherein m is an integer from 1 to 26; and

Z is selected from the group consisting of:

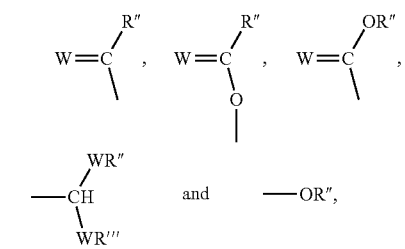

wherein W is selected from the group consisting of oxygen and sulfur;

wherein at least one of $X_1, X_2, \ldots Xn-1$ comprises a Z other than hydrogen, and wherein:

each of $R_1, R'_1, R_2, \ldots Rn-1, Rn, R'n$, each of R" and R''' and each of Ra, R'a, Rb, R'b, . . . Rm-1, R'm-1, Rm and R'm is independently selected from the group consisting of hydrogen, alkyl, alkenyl, alkynyl, cycloalkyl, aryl, heteroaryl, halo, trihalomethyl, hydroxy, alkoxy, aryloxy, thiohydroxy, thioalkoxy, thioaryloxy, phosphonate, phosphate, phosphinyl, sulfonyl, sulfinyl, sulfonamide, amide, carbonyl, thiocarbonyl, C-carboxy, O-carboxy, C-carbamate, N-carbamate, C-thiocarboxy, S-thiocarboxy and amino, or, alternatively, at least two of $R_1, R'_1, R2, \ldots Rn-1, Rn$ and Rn and/or at least two of Ra, R'a, Rb, R'b, . . . Rm-1, R'm-1, Rm and R'm form at least one four-, five- or six-membered aromatic, heteroaromatic, alicyclic or heteroalicyclic ring.

In some embodiments, the compound is 1-hexadecyl-2-(4'-carboxybutyl)-glycero-3-phosphocholine (VB-201). In some embodiments, the compound is (R)-1-hexadecyl-2-(4'-carboxybutyl)-sn-glycero-3-phosphocholine. In other embodiments, the compound has the following structure:

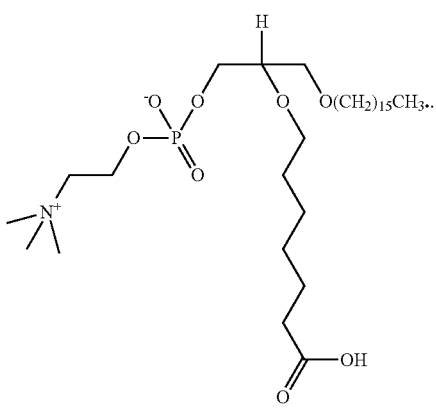

In other embodiments, the compound has the following structure:

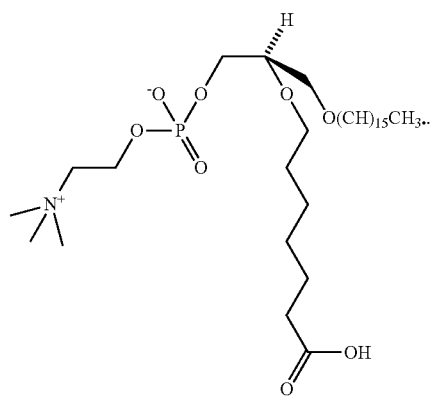

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention.

FIGS. 1A-1D show VB-201 inhibits lipopolysaccharide (LPS) (TLR4)-induced signaling in human monocytes (primary CD14+).

FIGS. 2A-2B show VB-201 inhibits PGN (TLR2)-induced signaling in human monocytes (THP-1 cell line).

FIG. 4 shows VB-201 inhibits chemokine-induced migration of human monocytes (primary CD14+).

FIG. 5 shows VB-201 inhibits SDF1-induced cell migration of human monocytes (THP-1 cell line).

FIG. 6 shows VB-201 inhibits RANTES-induced signaling in human monocytes (primary CD14+).

FIG. 8 shows the effect of VB-201 on LPS-binding by human primary monocytes. Samples were incubated with VB-201 at the indicated concentrations for 20 minutes before biotin-LPS (100 ng/ml) was added for an additional 15 minutes. Results are the mean fluorescence intensity (MFI) of triplicates.

FIG. 10 shows VB-201 inhibits IL-12p40 secretion in LPS (TLR4)-stimulated human Mo-derived DCs.

FIGS. 11A-11B show the effect of VB-201 on liver inflammation (FIG. 11A). NASH was induced by injection of mice with 200 μg streptozotocin (STZ) two days after birth and by feeding a high fat diet (HFD) from four weeks of age. Mice were then either treated with vehicle (negative control), VB-201 (4 mg/kg), or telmisartan (10 mg/kg; positive control) at six weeks of age for three weeks, or not treated (Normal). Mice were sacrificed at nine weeks of age. FIG. 11A shows the mean liver inflammation score following treatment (Mean±S.E; Normal—n=5, Vehicle—n=8, VB-201—n=8, Telmisartan—n=6). FIG. 11B shows H&E stained liver samples following treatment (200× magnification).

FIGS. 12A-12B show the effect of VB-201 on liver fibrosis. NASH was induced as explained in FIGS. 11A-11B. Staining of liver histological samples with Sirius red was used to determine the extent of fibrosis. FIG. 12A shows the mean fibrosis area following treatment (% from analyzed liver section; Mean±S.E; Normal—n=5, Vehicle—n=8, VB-201—n=8, Telmisartan—n=6). FIG. 12B shows Sirius red staining of liver samples following treatment (200× magnification).

FIG. 13 presents bar graphs showing the effect of VB-201 in reducing the number of damaged glomeruli (%) in a renal fibrosis model. Damaged glomeruli (%) in healthy rats (n=3) (white bar), sham operated rats (n=3) (white bar with stripes), nephrectomized rats treated with solvent control (0.5% ethanol/PBS) (black bar) (n=7), nephrectomized rats VB-201 4 mg/kg treated (n=7) (light gray bar) or nephrectomized rats telmisartan 10 mg/kg treated (n=8) (dark gray bar) were evaluated at 8 weeks. Statistical data vs. nephrectomized rats treated with solvent control (0.5% ethanol/PBS) is presented as follows: * represents p=0.01;  represents p≤0.005; and * represents p≤0.001. Abbreviations are: Nx, nephrectomized; Eth, ethanol.

FIG. 14 presents bar graphs showing the effect of VB-201 in reducing glomerular sclerosis (%). Glomerular sclerosis (%) in healthy rats (n=3) (white bar), sham operated rats (n=3) (white bar with stripes), nephrectomized rats treated with solvent control (0.5% ethanol/PBS) (black bar) (n=7), nephrectomized rats VB-201 4 mg/kg treated (n=8) (light gray bar) or nephrectomized rats telmisartan 10 mg/kg treated (n=8) (dark gray bar) were evaluated at 8 weeks. Statistical data vs. nephrectomized rats treated with solvent control (0.5% ethanol/PBS) is presented as follows: * represents p<0.05;  represents p≤0.005; and * represents p≤0.001. Abbreviations are: Nx, nephrectomized; Eth, ethanol.

FIG. 15 presents PAS staining (×400) images showing the effect of VB-201 in reducing glomerular sclerosis. Renal morphology was assessed by light microscope in PAS stained sections of healthy rats (Healthy ×400), sham operated rats (Sham ×400), nephrectomized rats treated with solvent control (0.5% ethanol/PBS) (Nx PBS 0.5% Eth ×400), nephrectomized rats VB-201 4 mg/kg treated (Nx VB-201 4 mg/kg ×400) or nephrectomized rats telmisartan 10 mg/kg treated (Nx Telmisartan 10 mg/kg ×400) at 8 weeks following the first surgery. Abbreviations are: Nx, nephrectomized; Eth, ethanol, PAS, Periodic Acid-Schiff.

FIGS. 16A-16C show the effect of VB-201 on monocyte/macrophage cell infiltration in the glomeruli (FIG. 16A) or in the interstitium (FIG. 16B). CD68 positive cells in the glomeruli (cells/glomeruli) and in the interstitium (cells/mm$^2$) were evaluated in healthy rats (n=3) (white bar), sham operated rats (n=3) (white bar with stripes), nephrectomized rats treated with solvent control (0.5% ethanol/PBS) (black bar) (n=7), nephrectomized rats VB-201 4 mg/kg treated (n=8) (light gray bar) or nephrectomized rats telmisartan 10 mg/kg treated (n=8) (dark gray bar) were evaluated at 8 weeks. Statistical data vs. nephrectomized rats treated with solvent control (0.5% ethanol/PBS) is presented as follows: in FIG. 16A, * represents p=0.008; and  represents p≤0.001; and in FIG. 16B**, * represents p≤0.005. FIG. 16C presents representative CD68 staining (×400) images showing the effect of VB-201 in reducing the number of CD68 cells. Abbreviations are: Nx, nephrectomized; Eth, ethanol.

FIGS. 17A-17B present bar graphs showing the effect of VB-201 on pro-fibrotic markers. Relative expression of Collagen IV (FIG. 17A) and TGF-β (FIG. 17B) in the kidney was evaluated in healthy rats (white bar), sham operated rats (white bar with stripes), nephrectomized rats treated with solvent control (0.5% ethanol/PBS) (black bar), nephrectomized rats VB-201 4 mg/kg treated (light gray bar) or nephrectomized rats telmisartan 10 mg/kg treated (dark gray bar) at 8 weeks. Statistical data vs. nephrectomized rats treated with solvent control (0.5% ethanol/PBS) is presented as follows: in FIG. 17A, * represents p≤0.05; and in FIG. 17B, * represents p≤0.001. Abbreviations are: Nx, nephrectomized; Eth, ethanol.

FIG. 18 presents bar graphs showing that VB-201 inhibits IL-12/23p40 expression in livers of NASH-induced mice. Mice were induced for NASH and VB-201 was administered orally at a dose of 4 mg/kg once daily from Week 6 to Week 9. Telmisartan was administered at a dose of 10 mg/kg once daily. Q-PCR was performed on RNA extracted from livers of NASH-induced mice treated with vehicle (solvent, n=8), VB-201 (n=7), telmisartan (n=5) as described above, or from livers of normal mice. Q-PCR was used to detect IL-12/23p40. GAPDH was used to normalize RNA levels. Analysis of IL-12/23p40 in the livers of NASH-induced mice shows that VB-201 significantly attenuated the expression of IL-12/23p40, with p≤0.05.

DETAILED DESCRIPTION OF THE INVENTION

Figure 2B:
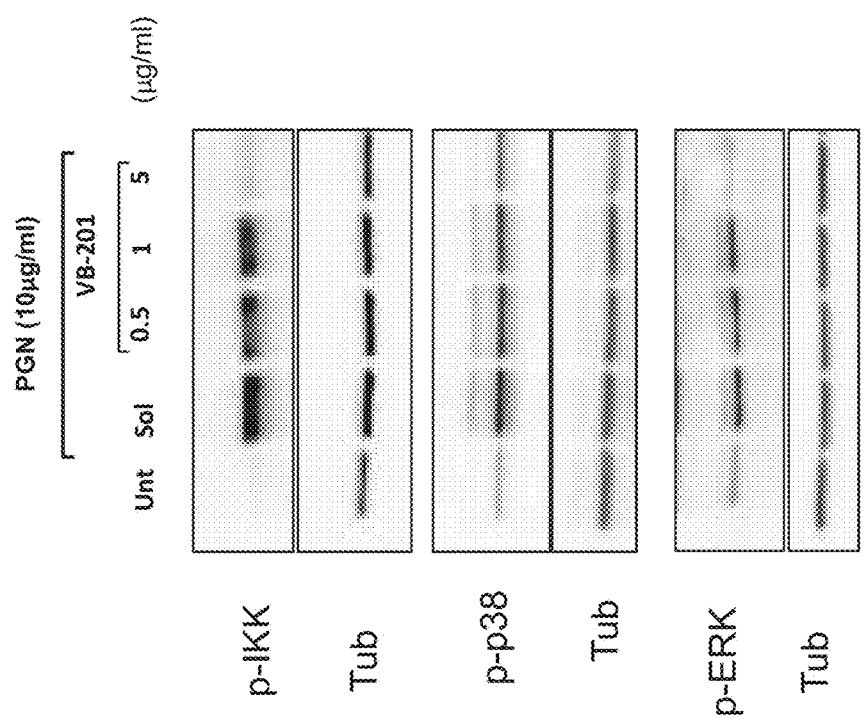

Before explaining embodiments of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

General Definitions

The terms "comprises", "comprising", "includes", "including", "having", and their conjugates mean "including but not limited to."

The word "optionally" is used herein to mean "is provided in some embodiments and not provided in other embodiments." Any particular embodiment of the invention can include a plurality of "optional" features unless such features conflict.

As used herein, the singular form "a", "an" and "the" include plural references unless the context clearly dictates otherwise. For example, the term "a compound" or "at least one compound" may include a plurality of compounds, including mixtures thereof.

As used herein, the term "about" modifying an amount related to the invention refers to variation in the numerical quantity that can occur, for example, through routine testing and handling; through inadvertent error in such testing and handling; through differences in the manufacture, source, or purity of ingredients employed in the invention; and the like. Whether or not modified by the term "about", the claims include equivalents of the recited quantities. In one embodiment, the term "about" means within 10% of the reported numerical value.

The term "therapeutically effective amount," as used herein, refers to that amount of a given therapeutic agent sufficient to result in amelioration of one or more symptoms of a disorder or condition, or prevent appearance or advancement of a disorder or condition, or cause regression of or cure from the disorder or condition. In some embodiments, a therapeutically effective amount of VB-201 is about 5 mg to about 160 mg VB-201 per day.

As used herein throughout, the term "alkyl" refers to a saturated aliphatic hydrocarbon including straight chain and branched chain groups. In some embodiments, the alkyl group has 1 to 20 carbon atoms. Whenever a numerical range; e.g., "1-20", is stated herein, it implies that the group, in this case the alkyl group, may contain 1 carbon atom, 2 carbon atoms, 3 carbon atoms, etc., up to and including 20 carbon atoms. In some embodiments, the alkyl is a medium size alkyl having 1 to 10 carbon atoms. In some embodiments, the alkyl is a lower alkyl having 1 to 4 carbon atoms. The alkyl group can be substituted (e.g., with 1 to 5 substituent groups) or unsubstituted. In any of the embodiments described herein, the alkyl can be unsubstituted. In any of the embodiments described herein, the alkyl can also be substituted by one to five substituent groups, wherein the substituent group can be, for example, cycloalkyl, alkenyl, alkynyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, azide, sulfonyl, sulfinyl, sulfonamide, phosphonyl, phosphinyl, oxo, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, and amino, as these terms are defined herein.

A "cycloalkyl" group refers to an all-carbon monocyclic or fused ring (i.e., rings which share an adjacent pair of carbon atoms) group wherein one of more of the rings does not have a completely conjugated pi-electron system. Examples, without limitation, of cycloalkyl groups are cyclopropane, cyclobutane, cyclopentane, cyclopentene, cyclohexane, cyclohexadiene, cycloheptane, cycloheptatriene, and adamantane. A cycloalkyl group can be substituted (e.g., with 1 to 5 substituent groups) or unsubstituted. In any of the embodiments described herein, the cycloalkyl can be unsubstituted. In any of the embodiments described herein, the cycloalkyl can also be substituted by one to five substituent groups, wherein the substituent group can be, for example, alkyl, alkenyl, alkynyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, azide, sulfonyl, sulfinyl, sulfonamide, phosphonyl, phosphinyl, oxo, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, and amino, as these terms are defined herein.

An "alkenyl" group refers to an aliphatic hydrocarbon group which contains at least two carbon atoms and at least one carbon-carbon double bond, which can be straight or branched. An alkenyl group can be substituted or unsubstituted.

An "alkynyl" group refers to an aliphatic hydrocarbon group which contains at least two carbon atoms and at least one carbon-carbon triple bond. An alkynyl group can be substituted or unsubstituted.

An "aryl" group refers to an all-carbon monocyclic or fused-ring polycyclic (i.e., rings which share adjacent pairs of carbon atoms) groups having a completely conjugated pi-electron system. In any of the embodiments described herein, aryl groups can have 6 to 14 carbons, e.g., 6 to 10 carbons. Examples, without limitation, of aryl groups are phenyl, naphthalenyl and anthracenyl. The aryl group can be substituted (e.g., with 1 to 5 substituent groups) or unsubstituted. When substituted, the substituent group can be, for example, alkyl, alkenyl, alkynyl, cycloalkyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, azide, sulfonyl, sulfinyl, sulfonamide, phosphonyl, phosphinyl, oxo, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, and amino, as these terms are defined herein. In any of the embodiments described herein, the aryl group can be a phenyl group, optionally substituted, for example, by one to five substituent such as halogens (e.g., fluorine or chlorine), alkyl groups (e.g., a $C_{1-4}$ alkyl), or halogen substituted alkyls (e.g., trifluoromethyl).

A "heteroaryl" group refers to a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. In any of the embodiments described herein, heteroaryl groups can have 5 to 14 ring atoms, e.g., 5 to 10 ring atoms (e.g., 5 or 6 ring atoms). Examples, without limitation, of heteroaryl groups include pyrrole, furan, thiophene, imidazole, oxazole, thiazole, pyrazole, pyridine, pyrimidine, quinoline, isoquinoline and purine. The heteroaryl group can be substituted (e.g., with 1 to 5 substituent groups) or unsubstituted. When substituted, the substituent group can be, for example, alkyl, alkenyl, alkynyl, cycloalkyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, azide, sulfonyl, sulfinyl, sulfonamide, phosphonyl, phosphinyl, oxo, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, and amino, as these terms are defined herein.

A "heteroalicyclic" group refers to a monocyclic or fused ring group having in the ring(s) one or more heteroatoms such as nitrogen, oxygen and sulfur. The rings may also have one or more double bonds. However, the rings do not have a completely conjugated pi-electron system. In any of the embodiments described herein, heteroalicyclic groups can have 3 to 10 ring atoms, e.g., 5 to 10 ring atoms (e.g., 5 or 6 ring atoms). The heteroalicyclic can be substituted (e.g., with 1 to 5 substituent groups) or unsubstituted. When substituted, the substituted group can be, for example, alkyl, alkenyl, alkynyl, cycloalkyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, azide, sulfonyl, sulfinyl, sulfonamide, phosphonyl, phosphinyl, oxo, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, and amino, as these terms are defined herein. Representative examples are piperidine, piperazine, tetrahydrofuran, tetrahydropyran, morpholine and the like.

An "alkoxy" group refers to both an —O-alkyl and an —O-cycloalkyl group, wherein the alkyl or cycloalkyl can be any of those as defined herein.

An "aryloxy" group refers to both an —O-aryl and an —O-heteroaryl group, wherein the aryl or heteroaryl can be any of those as defined herein.

A "thiohydroxy" group refers to a —SH group.

A "thioalkoxy" group refers to both an —S-alkyl group, and an —S-cycloalkyl group, wherein the alkyl or cycloalkyl can be any of those as defined herein.

A "thioaryloxy" group refers to both an —S-aryl and an —S-heteroaryl group, wherein the aryl or heteroaryl can be any of those as defined herein.

A "carbonyl" group refers to a —C(=O)—R group, wherein R is hydrogen, alkyl, alkenyl, cycloalkyl, aryl, heteroaryl (bonded through a ring carbon) or heteroalicyclic (bonded through a ring carbon) as defined herein.

An "aldehyde" group refers to a carbonyl group, wherein R is hydrogen.

A "thiocarbonyl" group refers to a —C(=S)—R group, wherein R is as defined herein.

A "C-carboxy" group refers to a —C(=O)—O—R groups, wherein R is as defined herein.

An "O-carboxy" group refers to an RC(=O)—O— group, wherein R is as defined herein.

An "oxo" group refers to a =O group.

A "carboxylic acid" group refers to a C-carboxyl group in which R is hydrogen.

A "halo" group or "halogen" refers to fluorine, chlorine, bromine or iodine.

A "trihalomethyl" group refers to a —$CX_3$ group wherein X is a halo group as defined herein, e.g., a $CF_3$ group.

A "sulfinyl" group refers to an —S(=O)—R group, wherein R is as defined herein.

A "sulfonyl" group refers to an —S(=O)$_2$—R group, wherein R is as defined herein.

An "S-sulfonamido" group refers to a —S(=O)$_2$—$NR_2$ group, with each of R as is defined herein.

An "N-sulfonamido" group refers to an RS(=O)$_2$—NR group, wherein each of R is as defined herein.

An "O-carbamyl" group refers to an —OC(=O)—$NR_2$ group, wherein each of R is as defined herein.

An "N-carbamyl" group refers to an ROC(=O)—NR— group, wherein each of R is as defined herein.

An "O-thiocarbamyl" group refers to an —OC(=S)—$NR_2$ group, wherein each of R is as defined herein.

An "N-thiocarbamyl" group refers to an ROC(=S)NR— group, wherein each of R is as defined herein.

An "amino" group refers to an —$NR_2$ group wherein each of R is as defined herein.

A "C-amido" group refers to a —C(=O)—$NR_2$ group, wherein each of R is as defined herein.

An "N-amido" group refers to an RC(=O)—NR— group, wherein each of R is as defined herein.

A "urea" group refers to an —NRC(=O)—$NR_2$ group, wherein each of R is as defined herein.

A "guanidino" group refers to an —RNC(=N)—$NR_2$ group, wherein each of R is as defined herein.

A "guanyl" group refers to an $R_2$NC(=N)— group, wherein each of R is as defined herein.

The term "phosphonyl" or "phosphonate" describes a —P(=O)(OR)$_2$ group, with R as defined herein.

The term "phosphate" describes an —O—P(=O)(OR)$_2$ group, with each of R as defined herein.

A "phosphoric acid" is a phosphate group wherein each of R is hydrogen.

The term "phosphinyl" describes a —PR$_2$ group, with each of R as defined herein.

The term "thiourea" describes a —NR—C(=S)—NR— group, with each of R as defined herein.

The term "saccharide" refers to one or more sugar units, either an open-chain sugar unit or a cyclic sugar unit (e.g., pyranose- or furanose-based units), and encompasses any monosaccharide, disaccharide and oligosaccharide, unless otherwise indicated.

The term "stereoisomer" includes geometric isomers, such as E or Z isomers, enantiomers, diastereomers, and the like.

The term "stereoisomeric mixture" includes any mixture in any ratio of stereoisomers defined herein. In some embodiments, a stereoisomeric mixture includes a racemic mixture. In some embodiments, a stereoisomeric mixture includes an enantiomerically enriched mixture. In some embodiments, a stereoisomeric mixture includes a mixture of diastereomers in any ratio.

The term "enantiomeric excess" or "ee" refers to a measure for how much of one enantiomer is present compared to the other. For a mixture of R and S enantiomers, the percent enantiomeric excess is defined as |R−S|*100, where R and S are the respective mole or weight fractions of enantiomers in a mixture such that R+S=1. With knowledge of the optical rotation of a chiral substance, the percent enantiomeric excess is defined as $([\alpha]_{obs}/[\alpha]_{max})*100$, where $[\alpha]_{obs}$ is the optical rotation of the mixture of enantiomers and $[\alpha]_{max}$ is the optical rotation of the pure enantiomer.

The term "salt" includes both internal salt or external salt. In some embodiments, the salt is an internal salt, i.e., a zwitterion structure. In some embodiments, the salt is an external salt. In some embodiments, the external salt is a pharmaceutically acceptable salt having a suitable counter ion. Suitable counterions for pharmaceutical use are known in the art.

Throughout this application, various embodiments of this invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range, such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5 and 6. This applies regardless of the breadth of the range.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Oxidized Lipids

The present invention is directed, in part, to oxidized lipid compounds. In some embodiments, an oxidized lipid on the invention is a compound having a structure according to Formula 1:

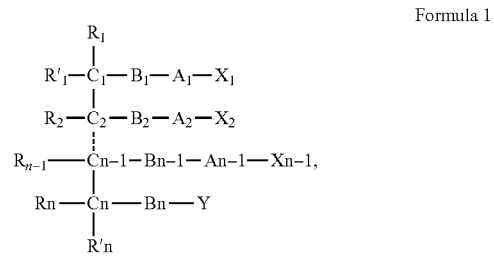

Formula 1 or a pharmaceutically acceptable salt, a hydrate or a solvate thereof, wherein:

n is an integer from 1 to 6, wherein when n is 1, Cn, Bn, Rn, and Y are absent, and $C_1$ is attached to R'n;

each of $B_1, B_2, \ldots Bn-1$ and Bn is independently selected from the group consisting of oxygen, sulfur, nitrogen, phosphorus and silicon, wherein each of said nitrogen, phosphorus and silicon is optionally substituted by one or more substituents selected from the group consisting of alkyl, halo, cycloalkyl, aryl, hydroxy, thiohydroxy, alkoxy, aryloxy, thioaryloxy, thioalkoxy and oxo;

each of $A_1, A_2, \ldots An-1$ and An is independently selected from the group consisting of CR"R"', C=O and C=S, Y is selected from the group consisting of hydrogen, acyl, alkyl, aryl, cycloalkyl, carboxy, saccharide, phosphoric acid, phosphoryl choline, phosphoryl ethanolamine, phosphoryl serine, phosphoryl cardiolipin, phosphoryl inositol, ethylphosphocholine, phosphorylmethanol, phosphorylethanol, phosphorylpropanol, phosphorylbutanol, phosphoryletha-nolamine-N-lactose, phosphoethanolamine-N-glutaric acid, phosphoethanolamine-N-[methoxy(propylene glycol)], phosphoinositol-4-phosphate, phosphoinositol-4,5-biphosphonate, phosphoinositol-4,5-bisphosphate, pyrophosphate, phosphoethanolamine-diethylenetriamine-pentaacetate, dinitrophenyl-phosphoethanolamine, phosphoglycerol and a moiety having the general formula:

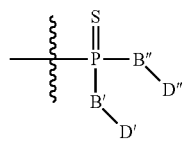

wherein:

each of B' and B" is independently selected from the group consisting of sulfur and oxygen; and each of D' and D" is independently selected from the group consisting of hydrogen, alkyl, amino substituted alkyl, cycloalkyl, phosphonate and thiophosphonate; and each of $X_1, X_2, \ldots, Xn-1$ is independently a saturated or unsaturated hydrocarbon having the general Formula 2:

Formula 2

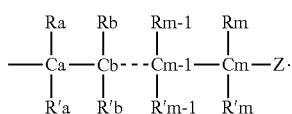

wherein, m is an integer from 1 to 26; and
Z is selected from the group consisting of:

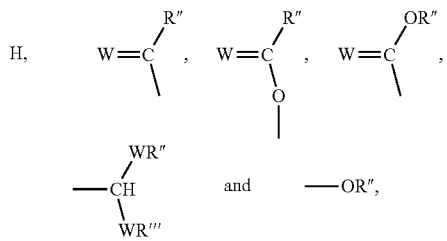

wherein W is selected from the group consisting of oxygen and sulfur;
wherein at least one of $X_1, X_2, \ldots X_{n-1}$ comprises a Z other than hydrogen,
and wherein:
each of $R_1, R'_1, R_2, \ldots R_{n-1}, R_n, R'_n$, each of R" and R'" and each of Ra, R'a, Rb, R'b, ... Rm-1, R'm-1, Rm and R'm is independently selected from the group consisting of hydrogen, alkyl, alkenyl, alkynyl, cycloalkyl, aryl, heteroaryl, halo, trihalomethyl, hydroxy, alkoxy, aryloxy, thiohydroxy, thioalkoxy, thioaryloxy, phosphonate, phosphate, phosphinyl, sulfonyl, sulfonyl, sulfonamide, amide, carbonyl, thiocarbonyl, C-carboxy, O-carboxy, C-carbamate, N-carbamate, C-thiocarboxy, S-thiocarboxy and amino, or, alternatively, at least two of $R_1, R'_1, R2, \ldots R_{n-1}, R_n$ and R'n and/or at least two of Ra, R'a, Rb, R'b, Rm-1, R'm-1, Rm and R'm form at least one four-, five- or six-membered aromatic, heteroaromatic, alicyclic or heteroalicyclic ring,
or a pharmaceutically acceptable salt, a hydrate or a solvate thereof.

In other embodiments, an oxidized lipid on the invention is a compound having a structure according to Formula 3:

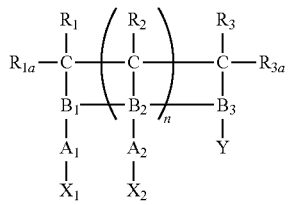

Formula 3 or a pharmaceutically acceptable salt, hydrate or solvate thereof.

In Formula 3, n is an integer selected from 1 to 4.

In Formula 3, $B_1$, each $B_2$, and $B_3$ are independently selected from the group consisting of oxygen, sulfur, and $NR_4$, wherein $R_4$ is selected from hydrogen, alkyl, cycloalkyl, aryl, and acyl.

In Formula 3, $A_1$ and each $A_2$ are independently selected from the group consisting of $CR_eR_{ee}$, $CR_e=CR_{ee}$, C=O and C=S, wherein $R_e$ and $R_{ee}$ are independently selected from hydrogen, alkyl, alkenyl, alkynyl, cycloalkyl, aryl, and heteroaryl.

In Formula 3, Y is selected from the group consisting of hydrogen, acyl, aryl, cycloalkyl, carboxy, saccharide, phosphoric acid, phosphoryl choline, phosphoryl ethanolamine, phosphoryl serine, phosphoryl cardiolipin, phosphoryl inositol, ethylphosphocholine, phosphorylmethanol, phosphorylethanol, phosphorylpropanol, phosphorylbutanol, phosphorylethanolamine-N-lactose, phosphoethanolamine-N-glutaric acid, phosphoethanolamine-N-[methoxy(propylene glycol)], phosphoinositol-4-phosphate, phosphoinositol-4,5-bisphosphate, pyrophosphate, phosphoethanolamine-diethylenetriamine-pentaacetate, dinitrophenyl-phosphoethanolamine, phosphoglycerol, and a moiety having the general formula:

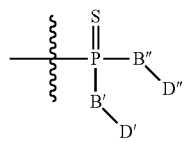

wherein:
each of B' and B" is independently selected from the group consisting of sulfur and oxygen; and
D' and D" are independently selected from the group consisting of hydrogen, alkyl, aminoalkyl, cycloalkyl, phosphonate and thiophosphonate.

In Formula 3, $X_1$ and each $X_2$ are independently a saturated or unsaturated, linear or branched hydrocarbon, wherein at least one of $X_1$ and $X_2$ is substituted with an oxidized moiety Z selected from the group consisting of:

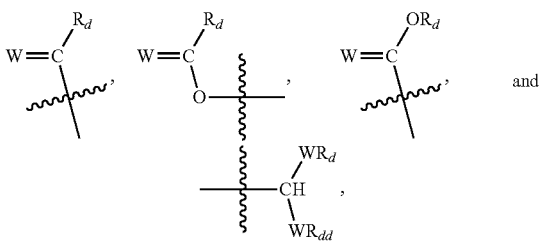

wherein W is oxygen or sulfur; and $R_d$ and $R_{dd}$ are independently selected from hydrogen, alkyl, alkenyl, alkynyl, cycloalkyl, aryl, and heteroaryl.

In one embodiment in Formula 3, $X_1$ and each $X_2$ independently have the general Formula 4:

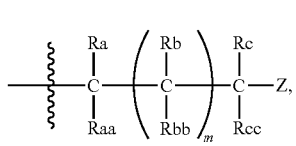

Formula 4

In Formula 4, m is an integer selected from 1 to 26.
In Formula 4, Z is selected from the group consisting of:

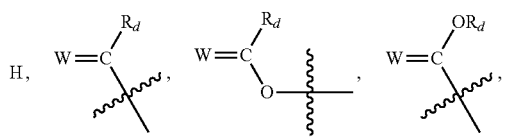

-continued

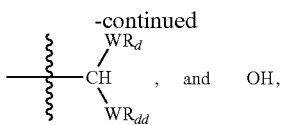, and OH, wherein W is oxygen or sulfur; and $R_d$ and $R_{dd}$ are independently selected from hydrogen, alkyl, alkenyl, alkynyl, cycloalkyl, aryl, and heteroaryl, wherein at least one of $X_1$ and $X_2$ comprises a Z other than hydrogen.

In Formula 3 and Formula 4, $R_1$, $R_{1a}$, each $R_2$, $R_3$, $R_{3a}$, $R_a$, $R_{aa}$, each $R_b$, each $R_{bb}$, $R_b$ and $R_{cc}$ are independently selected from the group consisting of hydrogen, alkyl, alkenyl, alkynyl, cycloalkyl, aryl, heteroaryl, halo, trihalomethyl, hydroxy, alkoxy, aryloxy, thiohydroxy, thioalkoxy, thioaryloxy, phosphonate, phosphate, phosphinyl, sulfonyl, sulfinyl, sulfonamide, amide, carbonyl, thiocarbonyl, C-carboxy, O-carboxy, C-carbamate, N-carbamate, C-thiocarboxy, S-thiocarboxy and amino, wherein at least two of $R_1$, $R_{1a}$, $R_2$, $R_3$ and $R_{3a}$ are optionally joined to form a four-, five- or six-membered aromatic, heteroaromatic, alicyclic or heteroalicyclic ring, and wherein at least two of $R_a$, $R_{aa}$, $R_b$, $R_{bb}$, $R_c$, and $R_{cc}$ are optionally joined to form a four-, five- or six-membered aromatic, heteroaromatic, alicyclic or heteroalicyclic ring.

In one embodiment in Formula 3, n is 1 or 2. In another embodiment in Formula 3, n is 1.

In one embodiment in Formula 3, Y is selected from the group consisting of hydrogen, acyl, alkyl, aryl, cycloalkyl, carboxy, saccharide, phosphoric acid, phosphoryl choline, phosphoryl ethanolamine, phosphoryl serine, phosphoryl cardiolipin, phosphoryl inositol, ethylphosphocholine, phosphorylmethanol, phosphorylethanol, phosphorylpropanol, phosphorylbutanol, phosphorylethanolamine-N-lactose, phosphoethanolamine-N-glutaric acid, phosphoethanolamine-N-[methoxy(propylene glycol)], phosphoinositol-4-phosphate, phosphoinositol-4,5-bisphosphate, pyrophosphate, phosphoethanolamine-diethylenetriamine-pentaacetate, dinitrophenyl-phosphoethanolamine, and phosphoglycerol.

In another embodiment in Formula 3, Y is selected from the group consisting of hydrogen, phosphoryl choline, and phosphoryl ethanolamine.

In another embodiment in Formula 3, Y is selected from the group consisting of phosphoryl choline, and phosphoryl ethanolamine.

In one embodiment in Formula 3, Y is phosphoryl choline.
In one embodiment in Formula 3, Z is

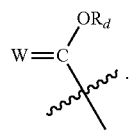

In another embodiment in Formula 3, Z is a carboxylic acid group.

In a further embodiment in Formula 3, n is 1 and Y is phosphoryl choline.

In a further embodiment in Formula 3, each of $B_1$, $B_2$, and $B_3$ is oxygen.

In a further embodiment in Formula 3, n is 1, Y is phosphoryl choline, and each of $B_1$, $B_2$, and $B_3$ is oxygen.

In one embodiment, the oxidized phospholipid useful in any of the methods of the present disclosure has a structure according to Formula 3a:

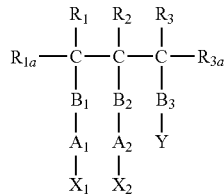

Formula 3a or a pharmaceutically acceptable salt, hydrate or solvate thereof.

In Formula 3a, $B_1$, $B_2$, and $B_3$ are independently selected from oxygen and sulfur.

In Formula 3a, $A_1$ and $A_2$ are independently selected from the group consisting of $CH_2$, $CH=CH$, $C=O$ and $C=S$.

In Formula 3a, Y is selected from the group consisting of hydrogen, acyl, alkyl, aryl, cycloalkyl, carboxy, saccharide, phosphoric acid, phosphoryl choline, phosphoryl ethanolamine, phosphoryl serine, phosphoryl cardiolipin, phosphoryl inositol, ethylphosphocholine, phosphorylmethanol, phosphorylethanol, phosphorylpropanol, phosphorylbutanol, phosphorylethanolamine-N-lactose, phosphoethanolamine-N-glutaric acid, phosphoethanolamine-N-[methoxy(propylene glycol)], phosphoinositol-4-phosphate, phosphoinositol-4,5-bisphosphate, pyrophosphate, phosphoethanolamine-diethylenetriamine-pentaacetate, dinitrophenyl-phosphoethanolamine, phosphoglycerol, and a moiety having the general formula:

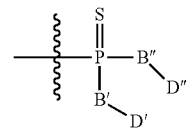

wherein:
each of B' and B'' is independently selected from the group consisting of sulfur and oxygen; and
each of D' and D'' is independently selected from the group consisting of hydrogen, alkyl, amino substituted alkyl, cycloalkyl, phosphonate and thiophosphonate.

In Formula 3a, $R_1$, $R_{1a}$, $R_2$, $R_3$, and $R_{3a}$ are independently selected from the group consisting of hydrogen, alkyl, alkenyl, alkynyl, cycloalkyl, aryl, heteroaryl, halo, trihalomethyl, hydroxy, alkoxy, aryloxy, thiohydroxy, thioalkoxy, thioaryloxy, phosphonate, phosphate, phosphinyl, sulfonyl, sulfinyl, sulfonamide, amide, carbonyl, thiocarbonyl, C-carboxy, O-carboxy, C-carbamate, N-carbamate, C-thiocarboxy, S-thiocarboxy and amino, wherein at least two of $R_1$, $R_{1a}$, $R_2$, $R_3$ and $R_{3a}$ are optionally joined to form a four-, five- or six-membered aromatic, heteroaromatic, alicyclic or heteroalicyclic ring, and wherein at least two of $R_a$, $R_{aa}$, $R_b$, $R_{bb}$, $R_c$, and $R_{cc}$ are optionally joined to form a four-, five- or six-membered aromatic, heteroaromatic, alicyclic or heteroalicyclic ring;

In Formula 3a, $X_1$ and $X_2$ are independently a saturated or unsaturated, linear or branched hydrocarbon, wherein at least one of $X_1$ and $X_2$ is substituted with an oxidized moiety Z having a formula selected from:

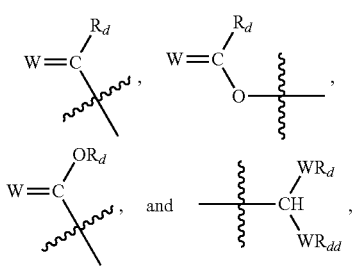

wherein W is oxygen or sulfur; and $R_d$ and $R_{dd}$ are independently selected from hydrogen, alkyl, alkenyl, alkynyl, cycloalkyl, aryl, and heteroaryl.

In one embodiment in Formula 3a, $X_1$ and $X_2$ independently have a structure according to Formula 4a:

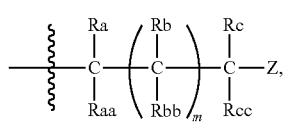

Formula 4a

In Formula 4a, m is an integer selected from 1 to 26.

In Formula 4a, $R_a$, $R_{aa}$, each $R_b$, each $R_{bb}$, $R_c$, and $R_{cc}$ are independently selected from the group consisting of hydrogen, alkyl, alkenyl, alkynyl, cycloalkyl, aryl, heteroaryl, halo, trihalomethyl, hydroxy, alkoxy, aryloxy, thiohydroxy, thioalkoxy, thioaryloxy, phosphonate, phosphate, phosphinyl, sulfonyl, sulfinyl, sulfonamide, amide, carbonyl, thiocarbonyl, C-carboxy, O-carboxy, C-carbamate, N-carbamate, C-thiocarboxy, S-thiocarboxy and amino, wherein at least two of $R_a$, $R_{aa}$, $R_b$, $R_{bb}$, $R_c$, and $R_{cc}$ are optionally joined to form a four-, five- or six-membered aromatic, heteroaromatic, alicyclic or heteroalicyclic ring.

In Formula 4a, Z is selected from the group consisting of:

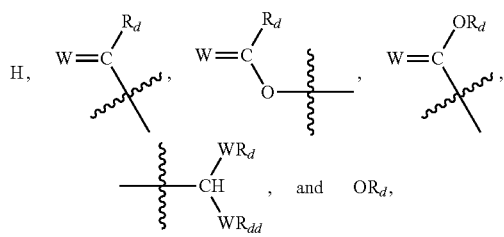

wherein W is oxygen or sulfur; and $R_d$ and $R_{dd}$ are independently selected from hydrogen, alkyl, alkenyl, alkynyl, cycloalkyl, aryl, and heteroaryl, wherein at least one of $X_1$ and $X_2$ comprises a Z other than hydrogen.

In one embodiment in Formula 3a, Z is

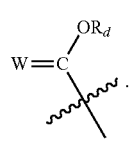

In another embodiment in Formula 3a, Z is a carboxylic acid group.

In one embodiment in Formula 3a, Y is selected from the group consisting of hydrogen, acyl, alkyl, aryl, cycloalkyl, carboxy, saccharide, phosphoric acid, phosphoryl choline, phosphoryl ethanolamine, phosphoryl serine, phosphoryl cardiolipin, phosphoryl inositol, ethylphosphocholine, phosphorylmethanol, phosphorylethanol, phosphorylpropanol, phosphorylbutanol, phosphorylethanolamine-N-lactose, phosphoethanolamine-N-glutaric acid, phosphoethanolamine-N-[methoxy(propylene glycol)], phosphoinositol-4-phosphate, phosphoinositol-4,5-bisphosphate, phosphoethanolamine-diethylenetriamine-pentaacetate, dinitrophenyl-phosphoethanolamine, and phosphoglycerol.

In one embodiment in Formula 3a, Y is selected from the group consisting of hydrogen, phosphoryl choline, and phosphoryl ethanolamine.

In another embodiment in Formula 3a, Y is selected from the group consisting of phosphoryl choline, and phosphoryl ethanolamine.

In one embodiment in Formula 3a, Y is phosphoryl choline.

In a further embodiment in Formula 3a, each of $B_1$, $B_2$, and $B_3$ is oxygen.

In a further embodiment in Formula 3a, Y is phosphoryl choline, and each of $B_1$, $B_2$, and $B_3$ is oxygen.

In one embodiment in Formula 3a, the oxidized phospholipid has a structure according to Formula 4b:

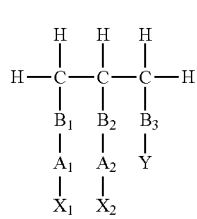

Formula 4b wherein $B_1$, $B_2$, $B_3$, $A_1$, $A_2$, $X_1$, $X_2$, and Y are defined as for Formula 3a.

In one embodiment, each of $B_1$, $B_2$, $B_3$ in Formula 4b is oxygen and the oxidized phospholipid has a structure according to the Formula 4c:

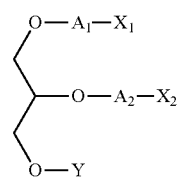

Formula 4c

In Formula 4c, $A_1$ is selected from the group consisting of $CH_2$, CH=CH and C=O. In one example, $A_1$ in Formula 4c is $CH_2$.

In Formula 4c, $A_2$ is absent or $CH_2$.

In Formula 4c, $X_1$ is an alkyl having from 1 to 30 carbon atoms.

In Formula 4c, $X_2$ is

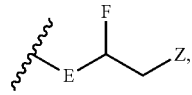

wherein

E is absent or is an alkyl chain having from 1 to 24 carbon atoms;

F is selected from the group consisting of hydrogen, hydroxy, alkyl, alkoxy, halide, acetoxy and aryl; and Z is selected from the group consisting of:

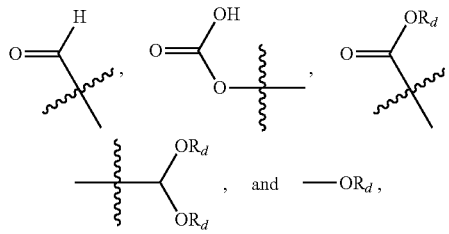

wherein $R_d$ is selected from H, alkyl and aryl.

In Formula 4c, Y is selected from the group consisting of hydrogen, alkyl, aryl, phosphoric acid, phosphoryl choline, phosphoryl ethanolamine, phosphoryl serine, phosphatidyl choline, phosphatidyl ethanolamine, phosphatidyl serine, phosphatidyl cardiolipin, phosphatidyl inositol, phosphoryl cardiolipin, phosphoryl inositol, ethylphosphocholine, phosphorylmethanol, phosphorylethanol, phosphorylpropanol, phosphorylbutanol, phosphorylethanolamine-N-lactose, phosphoethanolamine-N-[methoxy(propylene glycol)], phosphoinositol-4-phosphate, phosphoinositol-4,5-bisphosphate, pyrophosphate, phosphoethanolamine-diethylenetriamine-pentaacetate, dinitrophenyl-phosphoethanolamine, phosphoglycerol and a moiety having the general formula:

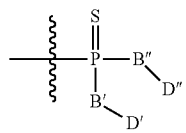

wherein:

each of B' and B" is independently selected from the group consisting of sulfur and oxygen; and each of D' and D" is independently selected from the group consisting of hydrogen, alkyl, amino substituted alkyl, cycloalkyl, phosphonate and thiophosphonate.

In one embodiment in Formula 4c, $X_1$ is alkyl having from 10 to 30 carbon atoms, or from 8 to 30 carbon atoms.

In one embodiment in Formula 4c, E is alkyl having from 1 to 10 carbon atoms, or from 1 to 4 carbon atoms.

In one embodiment in Formula 4c, Y is phosphoryl choline.

Each carbon atom in Formula 1, 2, 3, 3a, 4b and 4c is a chiral or non-chiral carbon atom, wherein each chiral carbon atom can have S-configuration or R-configuration.

In one embodiment, the oxidized lipid is 1-hexadecyl-2-(4'-carboxy)butyl-glycero-3-phosphocholine or 1-hexadecyl-2-(4'-carboxybutyl)-glycero-3-phosphocholine. As used herein, 1-hexadecyl-2-(4'-carboxy)butyl-glycero-3-phosphocholine and 1-hexadecyl-2-(4'-carboxybutyl)-glycero-3-phosphocholine are the same and both refer to the same compound, VB-201. VB-201 according to embodiments of this application may be a chiral enantiomer of 1-hexadecyl-2-(4'-carboxybutyl)-glycero-3-phosphocholine, i.e., either the (R)-enantiomer ((R)-1-hexadecyl-2-(4'-carboxybutyl)-sn-glycero-3-phosphocholine) or the (S)-enantiomer ((S)-1-hexadecyl-2-(4'-carboxybutyl)-sn-glycero-3-phosphocholine), or a mixture thereof (e.g., a racemate). In one embodiment, the oxidized phospholipid is (R)-1-hexadecyl-2-(4'-carboxy)butyl-sn-glycero-3-phosphocholine. In some embodiments, the (R)-1-hexadecyl-2-(4'-carboxy)butyl-sn-glycero-3-phosphocholine has an enantiomeric purity of about 80% ee or more, e.g., about 85% ee, about 90% ee, about 91% ee, about 92% ee, about 93% ee, about 94% ee, about 95% ee, about 96% ee, about 97% ee, about 98% ee, about 99% ee, about 99.5% ee or more. In other embodiments, the (R)-1-hexadecyl-2-(4'-carboxy)butyl-sn-glycero-3-phosphocholine has an enantiomeric purity of from about 80% ee to about 100% ee, about 85% ee to about 100% ee, about 90% ee to about 100% ee, about 95% ee to about 100%, about 80% ee to about 99.5% ee, about 85% ee to about 99.5% ee, about 90% ee to about 99.5% ee, about 95% ee to about 99.5%, or any range thereof.

In other embodiments, the oxidized lipid has the following structure:

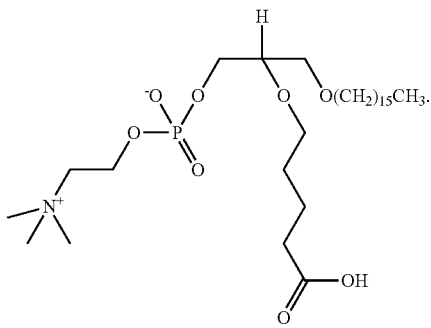

In other embodiments, the oxidized lipid has the following structure:

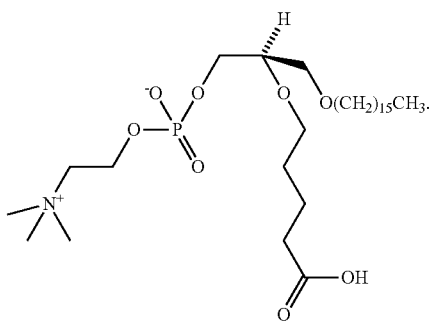

In some embodiments, an oxidized lipid compound of the invention treats or prevents fibrosis (e.g., liver fibrosis, kidney fibrosis, focal and segmental glomerulosclerosis, or any other fibrosis described herein) as well as, or better than, telmisartan. In other embodiments, an oxidized lipid compound of the invention reduces liver inflammation as well as, or better than, telmisartan. In other embodiments, an oxidized lipid compound of the invention reduces liver fibrosis as well as, or better than, telmisartan. In other embodiments, an oxidized lipid compound of the invention treats or prevents kidney fibrosis as well as, or better than, telmisartan. In other embodiments, an oxidized lipid compound of the invention treats or prevents focal and segmental glomerulosclerosis as well as, or better than, telmisartan.

Methods for synthesizing oxidized lipids of the invention have been described in, for example, International Publication Nos. WO 04/106486, WO 02/41827, and WO 2011/083469.

Pharmaceutical Compositions

Other embodiments of the invention relate to a pharmaceutical composition comprising an oxidized lipid of the invention. In some embodiments, the pharmaceutical composition comprises an oxidized lipid of the invention and a pharmaceutically acceptable vehicle. In other embodiments, the pharmaceutical composition comprises a therapeutically effective amount of the oxidized lipid. In some embodiments, the pharmaceutical composition comprises a therapeutically effective amount of the oxidized lipid and a pharmaceutically acceptable vehicle. As used herein, a therapeutically effective amount of an oxidized lipid is an amount effective to treat or prevent a disease or disorder of the present invention.

In other embodiments, the pharmaceutical compositions of the present invention can be orally administered.

In other embodiments, the pharmaceutical composition comprises a compound having a structure according to Formula 1:

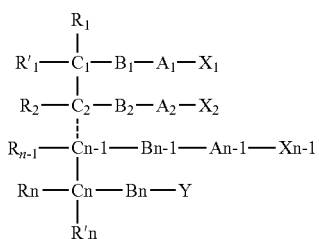

Formula 1 or a pharmaceutically acceptable salt, a hydrate or a solvate thereof, wherein:

n is an integer from 1 to 6, wherein when n is 1, $C_n$, $B_n$, $R_n$, and Y are absent, and $C_1$ is attached to R'n;

each of $B_1, B_2, \ldots B_{n-1}$ and $B_n$ is independently selected from the group consisting of oxygen, sulfur, nitrogen, phosphorus and silicon, wherein each of said nitrogen, phosphorus and silicon is optionally substituted by one or more substituents selected from the group consisting of alkyl, halo, cycloalkyl, aryl, hydroxy, thiohydroxy, alkoxy, aryloxy, thioaryloxy, thioalkoxy and oxo;

each of $A_1, A_2, \ldots A_{n-1}$ and $A_n$ is independently selected from the group consisting of CR"R'", C=O and C=S, Y is selected from the group consisting of hydrogen, acyl, alkyl, aryl, cycloalkyl, carboxy, saccharide, phosphoric acid, phosphoryl choline, phosphoryl ethanolamine, phosphoryl serine, phosphoryl cardiolipin, phosphoryl inositol, ethylphosphocholine, phosphorylmethanol, phosphorylethanol, phosphorylpropanol, phosphorylbutanol, phosphorylethanolamine-N-lactose, phosphoethanolamine-N-glutaric acid, phosphoethanolamine-N-[methoxy(propylene glycol)], phosphoinositol-4-phosphate, phosphoinositol-4,5-biphosphonate, phosphoinositol-4,5-bisphosphate, pyrophosphate, phosphoethanolamine-diethylenetriamine-pentaacetate, dinitrophenyl-phosphoethanolamine, phosphoglycerol and a moiety having the general formula:

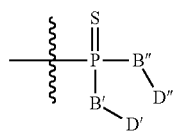

wherein:

each of B' and B" is independently selected from the group consisting of sulfur and oxygen; and each of D' and D'" is independently selected from the group consisting of hydrogen, alkyl, amino substituted alkyl, cycloalkyl, phosphonate and thiophosphonate; and each of $X_1, X_2, \ldots X_{n-1}$ is independently a saturated or unsaturated hydrocarbon having the general Formula 2:

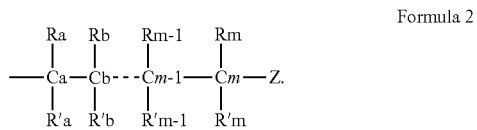

Formula 2 wherein, m is an integer from 1 to 26; and

Z is selected from the group consisting of:

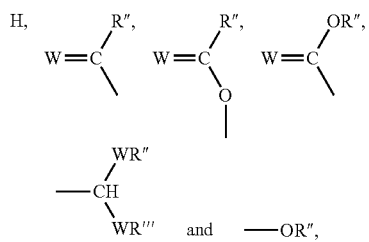

wherein W is selected from the group consisting of oxygen and sulfur;

wherein at least one of $X_1, X_2, \ldots X_{n-1}$ comprises a Z other than hydrogen, and wherein:

each of $R_1, R'_1, R_2, \ldots R_{n-1}, R_n, R'n$, each of R" and R'" and each of Ra, R'a, Rb, R'b, ... Rm-1, R'm-1, Rm and R'm is independently selected from the group consisting of hydrogen, alkyl, alkenyl, alkynyl, cycloalkyl, aryl, heteroaryl, halo, trihalomethyl, hydroxy, alkoxy, aryloxy, thiohydroxy, thioalkoxy, thioaryloxy, phosphonate, phosphate, phosphinyl, sulfonyl, sulfinyl, sulfonamide, amide, carbonyl, thiocarbonyl, C-carboxy, O-carboxy, C-carbamate, N-carbamate, C-thiocarboxy, S-thiocarboxy and amino, or, alternatively, at least two of $R_1, R'_1, R2, \ldots R_{n-1}, R_n$ and Rn and/or at least two of Ra, R'a, Rb, R'b, Rm-1, R'm-1, Rm and R'm form at least one four-, five- or six-membered aromatic, heteroaromatic, alicyclic or heteroalicyclic ring, or a pharmaceutically acceptable salt, a hydrate or a solvate thereof.

In other embodiments, the pharmaceutical composition comprises a compound having a structure according to Formula 3:

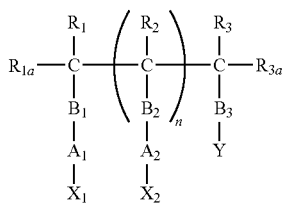

Formula 3 or a pharmaceutically acceptable salt, hydrate or solvate thereof.

In Formula 3, n is an integer selected from 1 to 4.

In Formula 3, $B_1$, each $B_2$, and $B_3$ are independently selected from the group consisting of oxygen, sulfur, and $NR_4$, wherein $R_4$ is selected from hydrogen, alkyl, cycloalkyl, aryl, and acyl.

In Formula 3, $A_1$ and each $A_2$ are independently selected from the group consisting of $CR_eR_{ee}$, $CR_e=CR_{ee}$, $C=O$ and $C=S$, wherein $R_e$ and $R_{ee}$ are independently selected from hydrogen, alkyl, alkenyl, alkynyl, cycloalkyl, aryl, and heteroaryl.

In Formula 3, Y is selected from the group consisting of hydrogen, acyl, aryl, cycloalkyl, carboxy, saccharide, phosphoric acid, phosphoryl choline, phosphoryl ethanolamine, phosphoryl serine, phosphoryl cardiolipin, phosphoryl inositol, ethylphosphocholine, phosphorylmethanol, phosphorylethanol, phosphorylpropanol, phosphorylbutanol, phosphorylethanolamine-N-lactose, phosphoethanolamine-N-glutaric acid, phosphoethanolamine-N-[methoxy(propylene glycol)], phosphoinositol-4-phosphate, phosphoinositol-4,5-bisphosphate, pyrophosphate, phosphoethanolamine-diethylenetriamine-pentaacetate, dinitrophenyl-phosphoethanolamine, phosphoglycerol, and a moiety having the general formula:

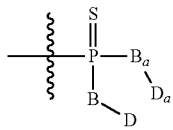

wherein:

each of B and $B_a$ is independently selected from the group consisting of sulfur and oxygen; and D and $D_a$ are independently selected from the group consisting of hydrogen, alkyl, aminoalkyl, cycloalkyl, phosphonate and thiophosphonate.

In Formula 3, $X_1$ and each $X_2$ are independently a saturated or unsaturated, linear or branched hydrocarbon, wherein at least one of $X_1$ and $X_2$ is substituted with an oxidized moiety Z selected from the group consisting of:

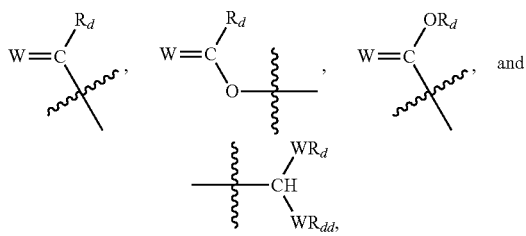

wherein W is oxygen or sulfur; and $R_d$ and $R_{dd}$ are independently selected from hydrogen, alkyl, alkenyl, alkynyl, cycloalkyl, aryl, and heteroaryl.

In one embodiment in Formula 3, $X_1$ and each $X_2$ independently have the general Formula 4:

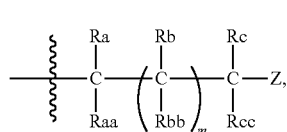

Formula 4

In Formula 4, m is an integer selected from 1 to 26.
In Formula 4, Z is selected from the group consisting of:

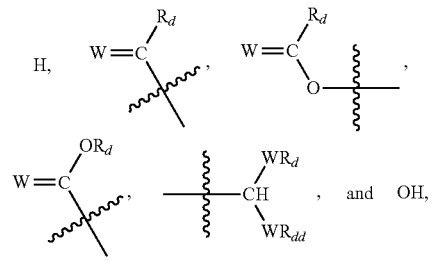

wherein W is oxygen or sulfur; and $R_d$ and $R_{dd}$ are independently selected from hydrogen, alkyl, alkenyl, alkynyl, cycloalkyl, aryl, and heteroaryl, wherein at least one of $X_1$ and $X_2$ comprises a Z other than hydrogen.

In Formula 3 and Formula 4, $R_1$, $R_{1a}$, each $R_2$, $R_3$, $R_{3a}$, $R_a$, $R_{aa}$, each $R_b$, each $R_{bb}$, $R_c$ and $R_{cc}$ are independently selected from the group consisting of hydrogen, alkyl, alkenyl, alkynyl, cycloalkyl, aryl, heteroaryl, halo, trihalomethyl, hydroxy, alkoxy, aryloxy, thiohydroxy, thioalkoxy, thioaryloxy, phosphonate, phosphate, phosphinyl, sulfonyl, sulfinyl, sulfonamide, amide, carbonyl, thiocarbonyl, C-carboxy, O-carboxy, C-carbamate, N-carbamate, C-thiocarboxy, S-thiocarboxy and amino, wherein at least two of $R_1$, $R_{1a}$, $R_2$, $R_3$ and $R_{3a}$ are optionally joined to form a four-, five- or six-membered aromatic, heteroaromatic, alicyclic or heteroalicyclic ring, and wherein at least two of $R_a$, $R_{aa}$, $R_b$, $R_{bb}$, $R_c$, and $R_{cc}$ are optionally joined to form a four-, five- or six-membered aromatic, heteroaromatic, alicyclic or heteroalicyclic ring.

In one embodiment in Formula 3, n is 1 or 2. In another embodiment in Formula 3, n is 1.

In one embodiment in Formula 3, Y is selected from the group consisting of hydrogen, acyl, alkyl, aryl, cycloalkyl, carboxy, saccharide, phosphoric acid, phosphoryl choline, phosphoryl ethanolamine, phosphoryl serine, phosphoryl cardiolipin, phosphoryl inositol, ethylphosphocholine, phosphorylmethanol, phosphorylethanol, phosphorylpropanol, phosphorylbutanol, phosphorylethanolamine-N-lactose, phosphoethanolamine-N-glutaric acid, phosphoethanolamine-N-[methoxy(propylene glycol)], phosphoinositol-4-phosphate, phosphoinositol-4,5-bisphosphate, pyrophosphate, phosphoethanolamine-diethylenetriamine-pentaacetate, dinitrophenyl-phosphoethanolamine, and phosphoglycerol.

In another embodiment in Formula 3, Y is selected from the group consisting of hydrogen, phosphoryl choline, and phosphoryl ethanolamine.

In another embodiment in Formula 3, Y is selected from the group consisting of phosphoryl choline, and phosphoryl ethanolamine.

In one embodiment in Formula 3, Y is phosphoryl choline.

In one embodiment in Formula 3, Z is

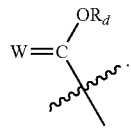

In another embodiment in Formula 3, Z is a carboxylic acid group.

In a further embodiment in Formula 3, n is 1 and Y is phosphoryl choline.

In a further embodiment in Formula 3, each of $B_1$, $B_2$, and $B_3$ is oxygen.

In a further embodiment in Formula 3, n is 1, Y is phosphoryl choline, and each of $B_1$, $B_2$, and $B_3$ is oxygen.

In one embodiment, the pharmaceutical composition comprises a compound having a structure according to Formula 3a:

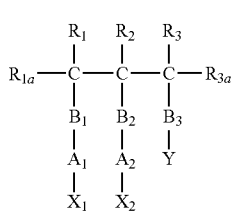

Formula 3a or a pharmaceutically acceptable salt, hydrate or solvate thereof.

In Formula 3a, $B_1$, $B_2$, and $B_3$ are independently selected from oxygen and sulfur.

In Formula 3a, $A_1$ and $A_2$ are independently selected from the group consisting of $CH_2$, CH=CH, C=O and C=S.

In Formula 3a, Y is selected from the group consisting of hydrogen, acyl, alkyl, aryl, cycloalkyl, carboxy, saccharide, phosphoric acid, phosphoryl choline, phosphoryl ethanolamine, phosphoryl serine, phosphoryl cardiolipin, phosphoryl inositol, ethylphosphocholine, phosphorylmethanol, phosphorylethanol, phosphorylpropanol, phosphorylbutanol, phosphorylethanolamine-N-lactose, phosphoethanolamine-N-glutaric acid, phosphoethanolamine-N-[methoxy(propylene glycol)], phosphoinositol-4-phosphate, phosphoinositol-4,5-bisphosphate, pyrophosphate, phosphoethanolamine-diethylenetriamine-pentaacetate, dinitrophenyl-phosphoethanolamine, and phosphoglycerol.

In Formula 3a, $R_1$, $R_{1a}$, $R_2$, $R_3$, and $R_{3a}$, are independently selected from the group consisting of hydrogen, alkyl, alkenyl, alkynyl, cycloalkyl, aryl, heteroaryl, halo, trihalomethyl, hydroxy, alkoxy, aryloxy, thiohydroxy, thioalkoxy, thioaryloxy, phosphonate, phosphate, phosphinyl, sulfonyl, sulfinyl, sulfonamide, amide, carbonyl, thiocarbonyl, C-carboxy, O-carboxy, C-carbamate, N-carbamate, C-thiocarboxy, S-thiocarboxy and amino, wherein at least two of $R_1$, $R_{1a}$, $R_2$, $R_3$ and $R_{3a}$ are optionally joined to form a four-, five- or six-membered aromatic, heteroaromatic, alicyclic or heteroalicyclic ring, and wherein at least two of $R_a$, $R_{aa}$, $R_b$, $R_{bb}$, $R_c$, and $R_{cc}$ are optionally joined to form a four-, five- or six-membered aromatic, heteroaromatic, alicyclic or heteroalicyclic ring;

In Formula 3a, $X_1$ and $X_2$ are independently a saturated or unsaturated, linear or branched hydrocarbon, wherein at least one of $X_1$ and $X_2$ is substituted with an oxidized moiety Z having a formula selected from:

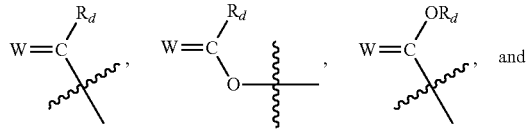

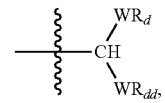

wherein W is oxygen or sulfur; and $R_d$ and $R_{dd}$ are independently selected from hydrogen, alkyl, alkenyl, alkynyl, cycloalkyl, aryl, and heteroaryl.

In one embodiment in Formula 3a, $X_1$ and $X_2$ independently have a structure according to Formula 4a:

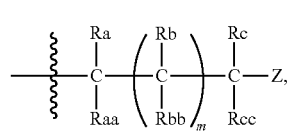

Formula 4a

In Formula 4a, m is an integer selected from 1 to 26.

In Formula 4a, $R_a$, $R_{aa}$, each $R_b$, each $R_{bb}$, $R_c$, and $R_{cc}$ are independently selected from the group consisting of hydrogen, alkyl, alkenyl, alkynyl, cycloalkyl, aryl, heteroaryl, halo, trihalomethyl, hydroxy, alkoxy, aryloxy, thiohydroxy, thioalkoxy, thioaryloxy, phosphonate, phosphate, phosphinyl, sulfonyl, sulfinyl, sulfonamide, amide, carbonyl, thiocarbonyl, C-carboxy, O-carboxy, C-carbamate, N-carbamate, C-thiocarboxy, S-thiocarboxy and amino, wherein at least two of $R_a$, $R_{aa}$, $R_b$, $R_{bb}$, $R_c$, and $R_{cc}$ are optionally joined to form a four-, five- or six-membered aromatic, heteroaromatic, alicyclic or heteroalicyclic ring.

In Formula 4a, Z is selected from the group consisting of:

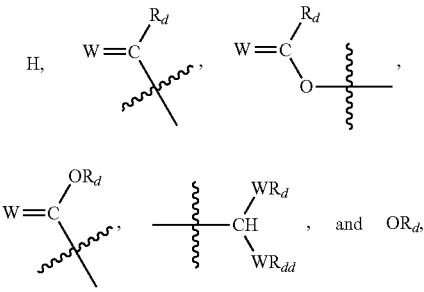

wherein W is oxygen or sulfur; and $R_d$ and $R_{dd}$ are independently selected from hydrogen, alkyl, alkenyl, alkynyl, cycloalkyl, aryl, and heteroaryl, wherein at least one of $X_1$ and $X_2$ comprises a Z other than hydrogen.

In one embodiment in Formula 3a, Z is

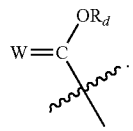

In another embodiment in Formula 3a, Z is a carboxylic acid group.

In one embodiment in Formula 3a, Y is selected from the group consisting of hydrogen, acyl, alkyl, aryl, cycloalkyl, carboxy, saccharide, phosphoric acid, phosphoryl choline, phosphoryl ethanolamine, phosphoryl serine, phosphoryl cardiolipin, phosphoryl inositol, ethylphosphocholine, phosphorylmethanol, phosphorylethanol, phosphorylpropanol, phosphorylbutanol, phosphorylethanolamine-N-lactose, phosphoethanolamine-N-glutaric acid, phosphoethanolamine-N-[methoxy(propylene glycol)], phosphoinositol-4-phosphate, phosphoinositol-4,5-bisphosphate, phosphoethanolamine-diethylenetriamine-pentaacetate, dinitrophenyl-phosphoethanolamine, and phosphoglycerol.

In one embodiment in Formula 3a, Y is selected from the group consisting of hydrogen, phosphoryl choline, and phosphoryl ethanolamine.

In another embodiment in Formula 3a, Y is selected from the group consisting of phosphoryl choline, and phosphoryl ethanolamine.

In one embodiment in Formula 3a, Y is phosphoryl choline.

In a further embodiment in Formula 3a, each of $B_1$, $B_2$, and $B_3$ is oxygen.

In a further embodiment in Formula 3a, Y is phosphoryl choline, and each of $B_1$, $B_2$, and $B_3$ is oxygen.

In one embodiment in Formula 3a, the oxidized phospholipid has a structure according to Formula 4b:

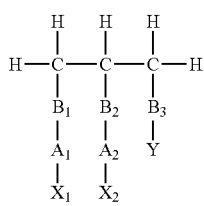

Formula 4b wherein $B_1$, $B_2$, $B_3$, $A_1$, $A_2$, $X_1$, $X_2$, and Y are defined as for Formula 3a.

In one embodiment, each of $B_1$, $B_2$, $B_3$ in Formula 4b is oxygen and the oxidized phospholipid has a structure according to the Formula 4c:

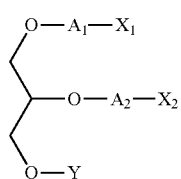

Formula 4c

In Formula 4c, $A_1$ is selected from the group consisting of $CH_2$, $CH=CH$ and $C=O$. In one example, $A_1$ in Formula 4c is $CH_2$.

In Formula 4c, $A_2$ is absent or $CH_2$.

In Formula 4c, $X_1$ is an alkyl having from 1 to 30 carbon atoms.

In Formula 4c, $X_2$ is

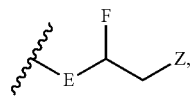

wherein
E is absent or is an alkyl chain having from 1 to 24 carbon atoms;
F is selected from the group consisting of hydrogen, hydroxy, alkyl, alkoxy, halide, acetoxy and aryl; and
Z is selected from the group consisting of:

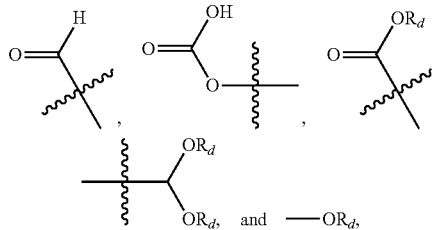

wherein $R_d$ is selected from H, alkyl and aryl.

In Formula 4c, Y is selected from the group consisting of hydrogen, alkyl, aryl, phosphoric acid, phosphoryl choline, phosphoryl ethanolamine, phosphoryl serine, phosphatidyl choline, phosphatidyl ethanolamine, phosphatidyl serine, phosphatidyl cardiolipin, phosphatidyl inositol, phosphoryl cardiolipin, phosphoryl inositol, ethylphosphocholine, phosphorylmethanol, phosphorylethanol, phosphorylpropanol, phosphorylbutanol, phosphorylethanolamine-N-lactose, phosphoethanolamine-N-[methoxy(propylene glycol)], phosphoinositol-4-phosphate, phosphoinositol-4,5-bisposphate, pyrophosphate, phosphoethanolamine-diethylenetriamine-pentaacetate, dinitrophenyl-phosphoethanolamine, phosphoglycerol.

In one embodiment in Formula 4c, $X_1$ is alkyl having from 10 to 30 carbon atoms, or from 8 to 30 carbon atoms.

In one embodiment in Formula 4c, E is alkyl having from 1 to 10 carbon atoms, or from 1 to 4 carbon atoms.

In one embodiment in Formula 4c, Y is phosphoryl choline.

Each carbon atom in Formula 1, 2, 3, 3a, 4b and 4c is a chiral or non-chiral carbon atom, wherein each chiral carbon atom can have S-configuration or R-configuration.

In another embodiment, the pharmaceutical compositions of the invention comprise 1-hexadecyl-2-(4'-carboxy)butyl-glycero-3-phosphocholine or 1-hexadecyl-2-(4'-carboxybutyl)-glycero-3-phosphocholine (VB-201). In another embodiment, the pharmaceutical compositions of the invention comprise (R)-1-hexadecyl-2-(4'-carboxy)butyl-sn-glycero-3-phosphocholine. In some embodiments, the (R)-1-hexadecyl-2-(4'-carboxy)butyl-sn-glycero-3-phosphocholine has an enantiomeric purity of about 80% ee or more, e.g., about 85% ee, about 90% ee, about 91% ee, about 92% ee, about 93% ee, about 94% ee, about 95% ee, about 96% ee, about 97% ee, about 98% ee, about 99% ee, about 99.5% ee or more. In other embodiments, the (R)-1-hexadecyl-2-(4'-carboxy)butyl-sn-glycero-3-phosphocholine has an enantiomeric purity of from about 80% ee to about 100% ee, about 85% ee to about 100% ee, about 90% ee to about 100% ee, about 95% ee to about 100%, about 80% ee to about 99.5% ee, about 85% ee to about 99.5% ee, about 90% ee to about 99.5% ee, about 95% ee to about 99.5%, or any range thereof.

In other embodiments, the pharmaceutical compositions of the invention comprise a compound of the following structure:

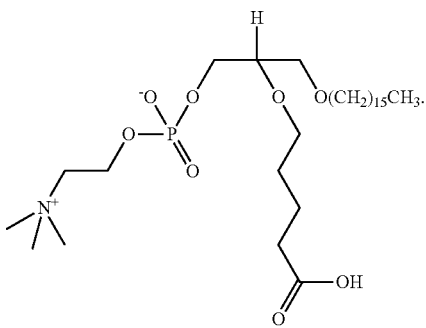

In other embodiments, the pharmaceutical compositions of the invention comprise a compound of the following structure:

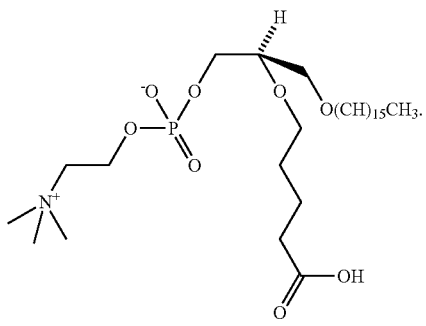

In other embodiments, the pharmaceutical composition treats or prevents fibrosis (e.g., liver fibrosis, kidney fibrosis, focal and segmental glomerulosclerosis, or any other fibrosis described herein) as well as, or better than, telmisartan. In other embodiments, the pharmaceutical composition reduces liver inflammation as well as, or better than, telmisartan. In other embodiments, the pharmaceutical composition reduces liver fibrosis as well as, or better than, telmisartan. In other embodiments, the pharmaceutical composition treats or prevents kidney fibrosis as well as, or better than, telmisartan. In other embodiments, the pharmaceutical composition treats or prevents focal and segmental glomerulosclerosis as well as, or better than, telmisartan.

Methods of Treating or Preventing Fibrosis

Embodiments of the invention relate to a method for treating or preventing fibrosis or liver inflammation comprising administering an oxidized lipid of the invention. In other embodiments, the method comprises administering a therapeutically effective amount of an oxidized lipid of the invention to a subject in need thereof. In other embodiments, the method comprises administering a pharmaceutical composition of the invention.

In some embodiments of the methods of the invention, the fibrosis is pulmonary fibrosis, liver fibrosis, skin fibrosis, or kidney fibrosis. In some embodiments of the methods of the invention, the fibrosis is heart fibrosis, bone marrow fibrosis, intestine fibrosis, joint fibrosis (knee, shoulder, or other joints), hand fibrosis, finger fibrosis, skeletal muscle fibrosis, neurofibrosis, and penis fibrosis. In other embodiments, the fibrosis is idiopathic pulmonary fibrosis (IPF), cystic fibrosis, progressive massive fibrosis, cirrhosis, steatohepatitis (fatty liver disease), nonalcoholic fatty liver disease (NAFLD), nonalcoholic steatohepatitis (NASH), endomyocardial fibrosis, myocardial infarction, atrial fibrosis, medastinal fibrosis, myelofibrosis, retroperitoneal fibrosis, nephrogenic systemic fibrosis, keloid, Crohn's disease, scleroderma/systemic sclerosis, arthrofibrosis, Peyronie's disease. Dupuytren's contracture, adhesive capsulitis, or focal and segmental glomerulosclerosis. In some embodiments the fibrosis is associated with liver inflammation. In some embodiments, the fibrosis is liver fibrosis. In some embodiments, the fibrosis is kidney fibrosis. In some embodiments, the subject in need of treatment or prevention of kidney fibrosis has a chronic kidney disease. In some embodiments, the fibrosis is focal and segmental glomerulosclerosis. In some embodiments, the subject in need of treatment or prevention of focal and segmental glomerulosclerosis has a chronic kidney disease.

In some embodiments, the fibrosis is a fibrosis that does not include idiopathic pulmonary fibrosis. In other embodiments, the fibrosis is a fibrosis that does not include cystic fibrosis. In other embodiments, the fibrosis is a fibrosis that does not include progressive massive fibrosis. In some embodiments, the fibrosis is a fibrosis that does not include cirrhosis. In some embodiments, the fibrosis is a fibrosis that does not include steatohepatitis (fatty liver disease). In some embodiments, the fibrosis is a fibrosis that does not include nonalcoholic fatty liver disease (NAFLD). In some embodiments, the fibrosis is a fibrosis that does not include nonalcoholic steatohepatitis (NASH). In some embodiments, the fibrosis is a fibrosis that does not include endomyocardial fibrosis. In some embodiments, the fibrosis is a fibrosis that does not include myocardial infarction. In some embodiments, the fibrosis is a fibrosis that does not include atrial fibrosis. In some embodiments, the fibrosis is a fibrosis that does not include medastinal fibrosis. In some embodiments, the fibrosis is a fibrosis that does not include myelofibrosis. In some embodiments, the fibrosis is a fibrosis that does not include retroperitoneal fibrosis. In some embodiments, the fibrosis is a fibrosis that does not include nephrogenic systemic fibrosis. In some embodiments, the fibrosis is a fibrosis that does not include keloid. In some embodiments, the fibrosis is a fibrosis that does not include Crohn's disease. In some embodiments, the fibrosis is a fibrosis that does not include scleroderma/systemic sclerosis. In some embodiments, the fibrosis is a fibrosis that does not include arthrofibrosis. In some embodiments, the fibrosis is a fibrosis that does not include Peyronie's disease. In some embodiments, the fibrosis is a fibrosis that does not include Dupuytren's contracture. In some embodiments, the fibrosis is a fibrosis that does not include adhesive capsulitis. In some embodiments, the fibrosis is a fibrosis that does not include focal and segmental glomerulosclerosis. In some embodiments, the fibrosis is a fibrosis that does not include fibrous lesions or plaques in the arteries.

In some embodiments, the oxidized lipid treats or prevents liver inflammation, but does not alter liver fibrosis. In other embodiments, the oxidized lipid treats or prevents liver fibrosis, but does not alter liver inflammation.

In some embodiments of the methods of the invention, activity of TLR2, TLR4 and/or CD14 is inhibited in a treated cell. In some embodiments, activity of TLR2 and TLR4 is inhibited; activity of TLR4 and CD14 is inhibited; activity of TLR2 and CD14 is inhibited; or activity of TLR2, TLR4 and CD14 is inhibited.

In some embodiments of the methods of the invention, steatosis in a subject treated with an oxidized lipid of the invention is not reduced, compared to that in untreated or placebo-treated subjects. In other embodiments, liver lobular formation in a subject treated with an oxidized lipid of the invention is decreased, compared to that in untreated or placebo-treated subjects. In other embodiments, liver lobular formulation in a subject treated with an oxidized lipid of the invention is not decreased, compared to that in untreated or placebo-treated subjects. In other embodiments, steatosis in a subject treated with an oxidized lipid of the invention is not reduced and liver lobular formation in a subject treated with an oxidized lipid of the invention is decreased, compared to those in untreated or placebo-treated subjects, respectively. In other embodiments, steatosis in a subject treated with an oxidized lipid of the invention is not reduced and liver lobular formation in a subject treated with an oxidized lipid of the invention is not decreased, compared to those in untreated or placebo-treated subjects, respectively. In other embodiments, foam cell-like macrophages are decreased in a subject treated with an oxidized lipid of the invention, compared to that in untreated or placebo-treated subjects. In some embodiments, liver lobular formation and foam cell-like macrophages in a subject treated with an oxidized lipid of the invention are decreased, compared to those in untreated or placebo-treated subjects, respectively. In some embodiments, liver lobular inflammation in a subject treated with an oxidized lipid of the invention is decreased, compared to that in untreated or placebo-treated subjects. In some embodiments, liver lobular inflammation and foam cell-like macrophages in a subject treated with an oxidized lipid of the invention are decreased, compared to those in untreated or placebo-treated subjects, respectively. In some embodiments, liver lobular formation, liver lobular inflammation and foam cell-like macrophages in a subject treated with an oxidized lipid of the invention are decreased, compared to those in untreated or placebo-treated subjects, respectively. In some embodiments, liver lobular formation in a subject treated with an oxidized lipid of the invention is decreased by about 5% to about 50% (e.g., about 5%, about 10%, about 20%, about 30%, about 40%, about 50%, or any ranges between the specified values) compared to that in untreated or placebo-treated subjects. In some embodiments, the formation of foam cell-like macrophages in a subject treated with an oxidized lipid of the invention is decreased by about 5% to about 50% (e.g., about 5%, about 10%, about 20%, about 30%, about 40%, about 50%, or any ranges between the specified values) compared to that in untreated or placebo-treated subjects. In some embodiments, liver lobular inflammation in a subject treated with an oxidized lipid of the invention is decreased by about 5% to about 50% (e.g., about 5%, about 10%, about 20%, about 30%, about 40%, about 50%, or any ranges between the specified values) compared to that in untreated or placebo-treated subjects.

In some embodiments, the oxidized lipid is a compound having a structure according to Formula 1:

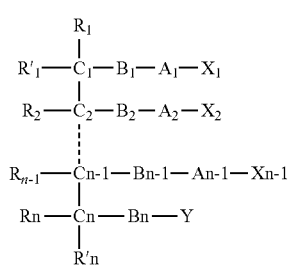

Formula 1 or a pharmaceutically acceptable salt, a hydrate or a solvate thereof, wherein:

n is an integer from 1 to 6, wherein when n is 1, Cn, Bn, Rn, and Y are absent, and $C_1$ is attached to R'n;

each of $B_1, B_2, \ldots Bn-1$ and Bn is independently selected from the group consisting of oxygen, sulfur, nitrogen, phosphorus and silicon, wherein each of said nitrogen, phosphorus and silicon is optionally substituted by one or more substituents selected from the group consisting of alkyl, halo, cycloalkyl, aryl, hydroxy, thiohydroxy, alkoxy, aryloxy, thioaryloxy, thioalkoxy and oxo;

each of $A_1, A_2, \ldots An-1$ and An is independently selected from the group consisting of CR"R"', C=O and C=S, Y is selected from the group consisting of hydrogen, acyl, alkyl, aryl, cycloalkyl, carboxy, saccharide, phosphoric acid, phosphoryl choline, phosphoryl ethanolamine, phosphoryl serine, phosphoryl cardiolipin, phosphoryl inositol, ethylphosphocholine, phosphorylmethanol, phosphorylethanol, phosphorylpropanol, phosphorylbutanol, phosphorylethanolamine-N-lactose, phosphoethanolamine-N-glutaric acid, phosphoethanolamine-N-[methoxy(propylene glycol)], phosphoinositol-4-phosphate, phosphoinositol-4,5-biphosphonate, phosphoinositol-4,5-bisphosphate, pyrophosphate, phosphoethanolamine-diethylenetriamine-pentaacetate, dinitrophenyl-phosphoethanolamine, phosphoglycerol and a moiety having the general formula:

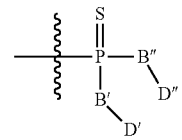

wherein:

each of B' and B" is independently selected from the group consisting of sulfur and oxygen; and each of D' and D" is independently selected from the group consisting of hydrogen, alkyl, amino substituted alkyl, cycloalkyl, phosphonate and thiophosphonate; and each of $X_1, X_2, \ldots Xn-1$ is independently a saturated or unsaturated hydrocarbon having the general Formula 2:

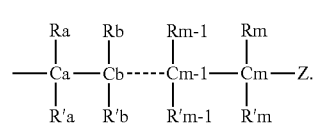

Formula 2 wherein, m is an integer from 1 to 26; and

Z is selected from the group consisting of:

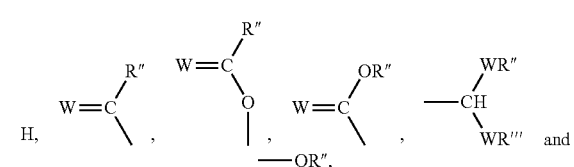

wherein W is selected from the group consisting of oxygen and sulfur;

wherein at least one of $X_1, X_2, \ldots X_{n-1}$ comprises a Z other than hydrogen, and wherein:

each of $R_1, R'_1, R_2, R_{n-1}, R_n, R'_n$, each of R" and R'" and each of $R_a, R'_a, R_b, R'_b, \ldots R_{m-1}, R'_{m-1}, R_m$ and $R'_m$ is independently selected from the group consisting of hydrogen, alkyl, alkenyl, alkynyl, cycloalkyl, aryl, heteroaryl, halo, trihalomethyl, hydroxy, alkoxy, aryloxy, thiohydroxy, thioalkoxy, thioaryloxy, phosphonate, phosphate, phosphinyl, sulfonyl, sulfinyl, sulfonamide, amide, carbonyl, thiocarbonyl, C-carboxy, O-carboxy, C-carbamate, N-carbamate, C-thiocarboxy, S-thiocarboxy and amino, or, alternatively, at least two of $R_1, R'_1, R2, \ldots R_{n-1}, R_n$ and $R'_n$ and/or at least two of $R_a, R'_a, R_b, R'_b, R_{m-1}, R'_{m-1}, R_m$ and $R'_m$ form at least one four-, five- or six-membered aromatic, heteroaromatic, alicyclic or heteroalicyclic ring, or a pharmaceutically acceptable salt, a hydrate or a solvate thereof.

In other embodiments, the oxidized lipid is a compound having a structure according to Formula 3:

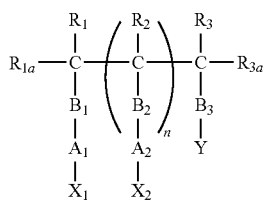

Formula 3 or a pharmaceutically acceptable salt, hydrate or solvate thereof.

In Formula 3, n is an integer selected from 1 to 4.

In Formula 3, $B_1$, each $B_2$, and $B_3$ are independently selected from the group consisting of oxygen, sulfur, and $NR_4$, wherein $R_4$ is selected from hydrogen, alkyl, cycloalkyl, aryl, and acyl.

In Formula 3, $A_1$ and each $A_2$ are independently selected from the group consisting of $CR_eR_{ee}$, $CR_e=CR_{ee}$, C=O and C=S, wherein $R_e$ and $R_{ee}$ are independently selected from hydrogen, alkyl, alkenyl, alkynyl, cycloalkyl, aryl, and heteroaryl.

In Formula 3, Y is selected from the group consisting of hydrogen, acyl, alkyl, aryl, cycloalkyl, carboxy, saccharide, phosphoric acid, phosphoryl choline, phosphoryl ethanolamine, phosphoryl serine, phosphoryl cardiolipin, phosphoryl inositol, ethylphosphocholine, phosphorylmethanol, phosphorylethanol, phosphorylpropanol, phosphorylbutanol, phosphorylethanolamine-N-lactose, phosphoethanolamine-N-glutaric acid, phosphoethanolamine-N-[methoxy(propylene glycol)], phosphoinositol-4-phosphate, phosphoinositol-4,5-bisphosphate, pyrophosphate, phosphoethanolamine-diethylenetriamine-pentaacetate, dinitrophenyl-phosphoethanolamine, phosphoglycerol, and a moiety having the general formula:

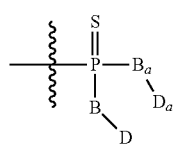

wherein:

each of B and $B_a$ is independently selected from the group consisting of sulfur and oxygen; and D and $D_a$ are independently selected from the group consisting of hydrogen, alkyl, aminoalkyl, cycloalkyl, phosphonate and thiophosphonate.

In Formula 3, $X_1$ and each $X_2$ are independently a saturated or unsaturated, linear or branched hydrocarbon, wherein at least one of $X_1$ and $X_2$ is substituted with an oxidized moiety Z selected from the group consisting of:

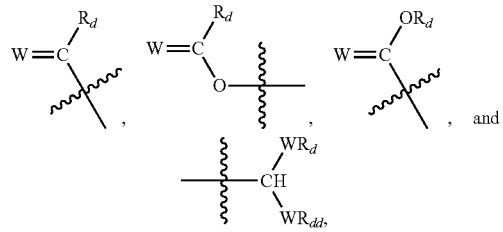

wherein W is oxygen or sulfur; and $R_d$ and $R_{dd}$ are independently selected from hydrogen, alkyl, alkenyl, alkynyl, cycloalkyl, aryl, and heteroaryl.

In one embodiment in Formula 3, $X_1$ and each $X_2$ independently have the general Formula 4:

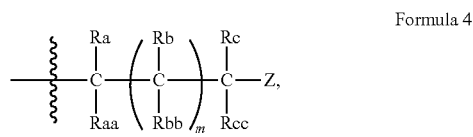

Formula 4

In Formula 4, m is an integer selected from 1 to 26.

In Formula 4, Z is selected from the group consisting of:

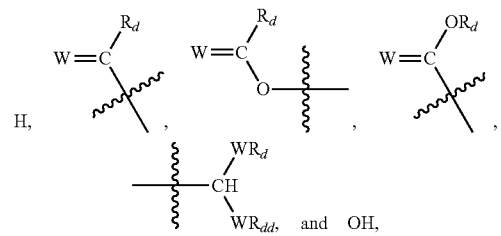

wherein W is oxygen or sulfur; and $R_d$ and $R_{dd}$ are independently selected from hydrogen, alkyl, alkenyl, alkynyl, cycloalkyl, aryl, and heteroaryl, wherein at least one of $X_1$ and $X_2$ comprises a Z other than hydrogen.

In Formula 3 and Formula 4, $R_1, R_{1a}$, each $R_2, R_3, R_{3a}, R_a, R_{aa}$, each $R_b$, each $R_{bb}, R_c$ and $R_{cc}$ are independently selected from the group consisting of hydrogen, alkyl, alkenyl, alkynyl, cycloalkyl, aryl, heteroaryl, halo, trihalomethyl, hydroxy, alkoxy, aryloxy, thiohydroxy, thioalkoxy, thioaryloxy, phosphonate, phosphate, phosphinyl, sulfonyl, sulfinyl, sulfonamide, amide, carbonyl, thiocarbonyl, C-carboxy, O-carboxy, C-carbamate, N-carbamate, C-thiocarboxy, S-thiocarboxy and amino, wherein at least two of $R_1, R_{1a}, R_2, R_3$ and $R_{3a}$ are optionally joined to form a four-, five- or six-membered aromatic, heteroaromatic, alicyclic or heteroalicyclic ring, and wherein at least two of $R_a, R_{aa}, R_b$, $R_{bb}$, $R_c$, and $R_{cc}$ are optionally joined to form a four-, five- or six-membered aromatic, heteroaromatic, alicyclic or heteroalicyclic ring.

In one embodiment in Formula 3, n is 1 or 2. In another embodiment in Formula 3, n is 1.

In one embodiment in Formula 3, Y is selected from the group consisting of hydrogen, acyl, alkyl, aryl, cycloalkyl, carboxy, saccharide, phosphoric acid, phosphoryl choline, phosphoryl ethanolamine, phosphoryl serine, phosphoryl cardiolipin, phosphoryl inositol, ethylphosphocholine, phosphorylmethanol, phosphorylethanol, phosphorylpropanol, phosphorylbutanol, phosphorylethanolamine-N-lactose, phosphoethanolamine-N-glutaric acid, phosphoethanolamine-N-[methoxy(propylene glycol)], phosphoinositol-4-phosphate, phosphoinositol-4,5-bisphosphate, pyrophosphate, phosphoethanolamine-diethylenetriaminepentaacetate, dinitrophenyl-phosphoethanolamine, and phosphoglycerol.

In another embodiment in Formula 3, Y is selected from the group consisting of hydrogen, phosphoryl choline, and phosphoryl ethanolamine.

In another embodiment in Formula 3, Y is selected from the group consisting of phosphoryl choline, and phosphoryl ethanolamine.

In one embodiment in Formula 3, Y is phosphoryl choline.

In one embodiment in Formula 3, Z is

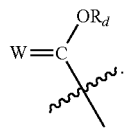

In another embodiment in Formula 3, Z is a carboxylic acid group.

In a further embodiment in Formula 3, n is 1 and Y is phosphoryl choline.

In a further embodiment in Formula 3, each of $B_1$, $B_2$, and $B_3$ is oxygen.

In a further embodiment in Formula 3, n is 1, Y is phosphoryl choline, and each of $B_1$, $B_2$, and $B_3$ is oxygen.

In one embodiment, the oxidized lipid has a structure according to Formula 3a:

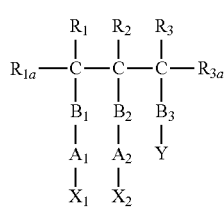

Formula 3a or a pharmaceutically acceptable salt, hydrate or solvate thereof.

In Formula 3a, $B_1$, $B_2$, and $B_3$ are independently selected from oxygen and sulfur.

In Formula 3a, $A_1$ and $A_2$ are independently selected from the group consisting of $CH_2$, $CH=CH$, $C=O$ and $C=S$.

In Formula 3a, Y is selected from the group consisting of hydrogen, acyl, alkyl, aryl, cycloalkyl, carboxy, saccharide, phosphoric acid, phosphoryl choline, phosphoryl ethanolamine, phosphoryl serine, phosphoryl cardiolipin, phosphoryl inositol, ethylphosphocholine, phosphorylmethanol, phosphorylethanol, phosphorylpropanol, phosphorylbutanol, phosphorylethanolamine-N-lactose, phosphoethanolamine-N-glutaric acid, phosphoethanolamine-N-[methoxy (propylene glycol)], phosphoinositol-4-phosphate, phosphoinositol-4,5-bisphosphate, pyrophosphate, phosphoethanolamine-diethylenetriaminepentaacetate, dinitrophenyl-phosphoethanolamine, and phosphoglycerol.

In Formula 3a, $R_1$, $R_{1a}$, $R_2$, $R_3$, and $R_{3a}$, are independently selected from the group consisting of hydrogen, alkyl, alkenyl, alkynyl, cycloalkyl, aryl, heteroaryl, halo, trihalomethyl, hydroxy, alkoxy, aryloxy, thiohydroxy, thioalkoxy, thioaryloxy, phosphonate, phosphate, phosphinyl, sulfonyl, sulfinyl, sulfonamide, amide, carbonyl, thiocarbonyl, C-carboxy, O-carboxy, C-carbamate, N-carbamate, C-thiocarboxy, S-thiocarboxy and amino, wherein at least two of $R_1$, $R_{1a}$, $R_2$, $R_3$ and $R_{3a}$ are optionally joined to form a four-, five- or six-membered aromatic, heteroaromatic, alicyclic or heteroalicyclic ring, and wherein at least two of $R_a$, $R_{aa}$, $R_b$, $R_{bb}$, $R_c$, and $R_{cc}$ are optionally joined to form a four-, five- or six-membered aromatic, heteroaromatic, alicyclic or heteroalicyclic ring;

In Formula 3a, $X_1$ and $X_2$ are independently a saturated or unsaturated, linear or branched hydrocarbon, wherein at least one of $X_1$ and $X_2$ is substituted with an oxidized moiety Z having a formula selected from:

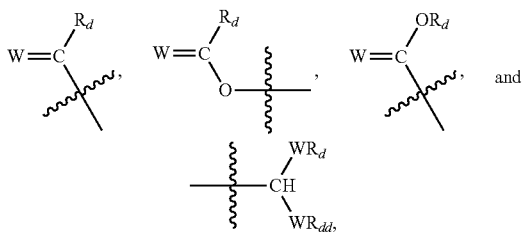

and wherein W is oxygen or sulfur; and $R_d$ and $R_{ad}$ are independently selected from hydrogen, alkyl, alkenyl, alkynyl, cycloalkyl, aryl, and heteroaryl.

In one embodiment in Formula 3a, $X_1$ and $X_2$ independently have a structure according to Formula 4a:

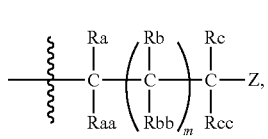

Formula 4a

In Formula 4a, m is an integer selected from 1 to 26.

In Formula 4a, $R_a$, $R_{aa}$, each $R_b$, each $R_{bb}$, $R_c$, and $R_{cc}$ are independently selected from the group consisting of hydrogen, alkyl, alkenyl, alkynyl, cycloalkyl, aryl, heteroaryl, halo, trihalomethyl, hydroxy, alkoxy, aryloxy, thiohydroxy, thioalkoxy, thioaryloxy, phosphonate, phosphate, phosphinyl, sulfonyl, sulfinyl, sulfonamide, amide, carbonyl, thiocarbonyl, C-carboxy, O-carboxy, C-carbamate, N-carbamate, C-thiocarboxy, S-thiocarboxy and amino, wherein at least two of $R_a$, $R_{aa}$, $R_b$, $R_{bb}$, $R_c$, and $R_{cc}$ are optionally joined to form a four-, five- or six-membered aromatic, heteroaromatic, alicyclic or heteroalicyclic ring.

In Formula 4a, Z is selected from the group consisting of:

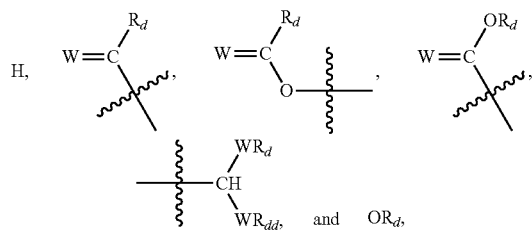

wherein W is oxygen or sulfur; and $R_d$ and $R_{dd}$ are independently selected from hydrogen, alkyl, alkenyl, alkynyl, cycloalkyl, aryl, and heteroaryl, wherein at least one of $X_1$ and $X_2$ comprises a Z other than hydrogen.

In one embodiment in Formula 3a, Z is

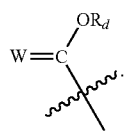

In another embodiment in Formula 3a, Z is a carboxylic acid group.

In one embodiment in Formula 3a, Y is selected from the group consisting of hydrogen, acyl, alkyl, aryl, cycloalkyl, carboxy, saccharide, phosphoric acid, phosphoryl choline, phosphoryl ethanolamine, phosphoryl serine, phosphoryl cardiolipin, phosphoryl inositol, ethylphosphocholine, phosphorylmethanol, phosphorylethanol, phosphorylpropanol, phosphorylbutanol, phosphorylethanolamine-N-lactose, phosphoethanolamine-N-glutaric acid, phosphoethanolamine-N-[methoxy(propylene glycol)], phosphoinositol-4-phosphate, phosphoinositol-4,5-bisphosphate, phosphoethanolamine-diethylenetriamine-pentaacetate, dinitrophenyl-phosphoethanolamine, and phosphoglycerol.

In one embodiment in Formula 3a, Y is selected from the group consisting of hydrogen, phosphoryl choline, and phosphoryl ethanolamine.

In another embodiment in Formula 3a, Y is selected from the group consisting of phosphoryl choline, and phosphoryl ethanolamine.

In one embodiment in Formula 3a, Y is phosphoryl choline.

In a further embodiment in Formula 3a, each of $B_1$, $B_2$, and $B_3$ is oxygen.

In a further embodiment in Formula 3a, Y is phosphoryl choline, and each of $B_1$, $B_2$, and $B_3$ is oxygen.

In one embodiment in Formula 3a, the oxidized phospholipid has a structure according to Formula 4b:

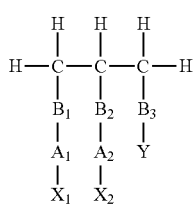

Formula 4b wherein $B_1$, $B_2$, $B_3$, $A_1$, $A_2$, $X_1$, $X_2$, and Y are defined as for Formula 3a.

In one embodiment, each of $B_1$, $B_2$, $B_3$ in Formula 4b is oxygen and the oxidized phospholipid has a structure according to the Formula 4c:

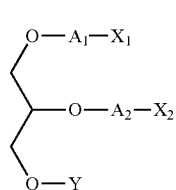

Formula 4c

In Formula 4c, $A_1$ is selected from the group consisting of $CH_2$, $CH=CH$ and $C=O$. In one example, $A_1$ in Formula 4c is $CH_2$.

In Formula 4c, $A_2$ is absent or $CH_2$.

In Formula 4c, $X_1$ is an alkyl having from 1 to 30 carbon atoms.

In Formula 4c, $X_2$ is

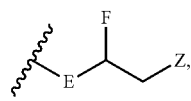

wherein

E is absent or is an alkyl chain having from 1 to 24 carbon atoms;

F is selected from the group consisting of hydrogen, hydroxy, alkyl, alkoxy, halide, acetoxy and aryl; and Z is selected from the group consisting of:

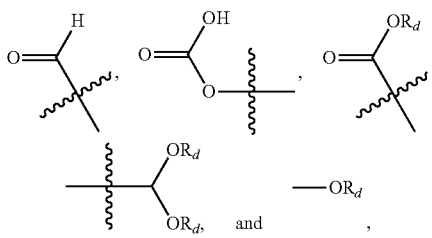

wherein $R_d$ is selected from H, alkyl and aryl.

In Formula 4c, Y is selected from the group consisting of hydrogen, alkyl, aryl, phosphoric acid, phosphoryl choline, phosphoryl ethanolamine, phosphoryl serine, phosphatidyl choline, phosphatidyl ethanolamine, phosphatidyl serine, phosphatidyl cardiolipin, phosphatidyl inositol, phosphoryl cardiolipin, phosphoryl inositol, ethylphosphocholine, phosphorylmethanol, phosphorylethanol, phosphorylpropanol, phosphorylbutanol, phosphorylethanolamine-N-lactose, phosphoethanolamine-N-[methoxy(propylene glycol)], phosphoinositol-4-phosphate, phosphoinositol-4,5-bisphosphate, pyrophosphate, phosphoethanolamine-diethylenetriamine-pentaacetate, dinitrophenyl-phosphoethanolamine, and phosphoglycerol.

In one embodiment in Formula 4c, $X_1$ is alkyl having from 10 to 30 carbon atoms, or from 8 to 30 carbon atoms.

In one embodiment in Formula 4c, E is alkyl having from 1 to 10 carbon atoms, or from 1 to 4 carbon atoms.

In one embodiment in Formula 4c, Y is phosphoryl choline.

Each carbon atom in Formula 1, 2, 3, 3a, 4b, and 4c is a chiral or non-chiral carbon atom, wherein each chiral carbon atom can have S-configuration or R-configuration.

In another embodiment, the oxidized lipid is 1-hexadecyl-2-(4'-carboxy)butyl-glycero-3-phosphocholine or 1-hexadecyl-2-(4'-carboxybutyl)-glycero-3-phosphocholine (VB-201). In another embodiment, the oxidized lipid is (R)-1-hexadecyl-2-(4'-carboxy)butyl-sn-glycero-3-phosphocholine. In some embodiments, the (R)-1-hexadecyl-2-(4'-carboxy)butyl-sn-glycero-3-phosphocholine has an enantiomeric purity of about 80% ee or more, e.g., about 85% ee, about 90% ee, about 91% ee, about 92% ee, about 93% ee, about 94% ee, about 95% ee, about 96% ee, about 97% ee, about 98% ee, about 99% ee, about 99.5% ee or more. In other embodiments, the (R)-1-hexadecyl-2-(4'-carboxy)butyl-sn-glycero-3-phosphocholine has an enantiomeric purity of from about 80% ee to about 100% ee, about 85% ee to about 100% ee, about 90% ee to about 100% ee, about 95% ee to about 100%, about 80% ee to about 99.5% ee, about 85% ee to about 99.5% ee, about 90% ee to about 99.5% ee, about 95% ee to about 99.5%, or any range thereof.

In other embodiments, the oxidized lipid has the following structure:

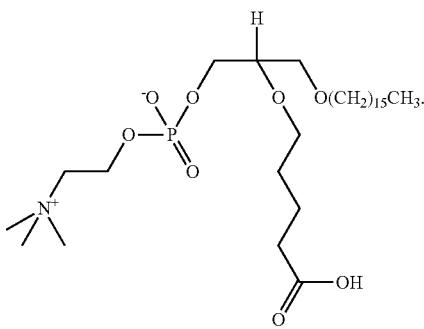

In other embodiments, the oxidized lipid has the following structure:

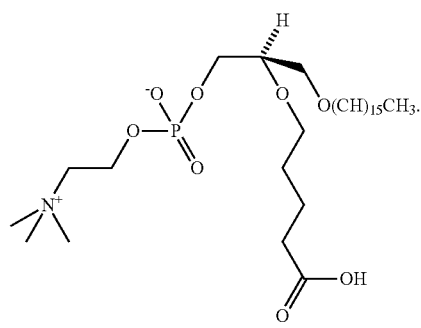

In other embodiments, the oxidized lipid compound treats or prevents fibrosis (e.g., liver fibrosis, kidney fibrosis, focal and segmental glomerulosclerosis, or any other fibrosis described herein) as well as, or better than, telmisartan. In other embodiments, the oxidized lipid compound reduces liver inflammation as well as, or better than, telmisartan. In other embodiments, the oxidized lipid compound reduces liver fibrosis as well as, or better than, telmisartan. In other embodiments, the oxidized lipid compound treats or prevents kidney fibrosis as well as, or better than, telmisartan. In other embodiments, the oxidized lipid compound treats or prevents focal and segmental glomerulosclerosis as well as, or better than, telmisartan.

In some embodiments, the subject is a mammal or a human. In other embodiments, the human is a female. In other embodiments, the human is a male.

EXAMPLES

Reference is now made to the following examples, which together with the above descriptions illustrate some embodiments of the invention in a non-limiting fashion.

Example 1

VB-201 Inhibits LPS (TLR4)-Induced Signaling in Human Monocytes (Primary CD14+)

Methods and Materials

Isolation of Monocytes

Venous blood samples were obtained from healthy male donors in compliance with the Institutional Review Board at the Sheba Medical Center, Ramat Gan, Israel. PBMCs were isolated on Ficoll-Paque PLUS (GE Healthcare, Uppsala, Sweden) using 50 ml Leucosep tubes (Greiner Bio-One, Frickenhausen, Germany). Cells were washed in PBS (Kibbutz Beit Haemek, Israel) and incubated at 4° C. for 15 minutes in a buffer containing PBS and 0.5% bovine serum albumin (BSA) with human CD14 microbeads (Miltenyi Biotec, Bergisch Gladbach, Germany).

Activation of Cells and Western Blotting

Cells ($10^6$/ml) were pretreated for 20 min with VB-201 at the doses indicated in FIG. 1, or with solvent (Sol), followed by 15 min activation with 100 ng/ml lipopolysaccharide (LPS) or were untreated (Unt). Cells were washed and resuspended in lysis buffer containing 1:100 dithiothreitol (DTT), phosphatase and protease inhibitors (Thermo Scientific). Samples were loaded onto a precast Criterion TGX gel (Bio-Rad, Hemel Hempstead, UK) and transferred onto nitrocellulose membrane. Blots were blocked with 5% milk or BSA in Tris buffered saline and Tween 20 (TBST) for 1 h, followed by incubation with primary and secondary antibodies. Membranes were developed using an ECL kit (Thermo Scientific). The following antibodies were used for immunoblotting:

Primary antibodies: p-p38 (Cat. No. 4511; 1:1000) and p-IKK (Cat. No. 2697; 1:1000) were from Cell Signaling Technology (Danvers, Mass., USA). p-ERK1/2 (Cat. No. M8159; 1:10 000) was purchased from Sigma (Israel). αTubulin (Tub) or Heat Shock Protein 90 (HSP90) served as a loading control.

Secondary antibodies: HRP donkey anti-rabbit (1:5000) and HRP goat anti-mouse (1:3000) were from Jackson ImmunoResearch (West Grove, Pa., USA). HRP donkey anti-goat (1:5000) was from Santa Cruz Biotechnology.

Results

To determine the effect of VB-201 on TLR4-mediated signaling pathways, isolated human primary monocytes (CD14+) were preincubated with VB-201 and then activated with LPS. FIGS. 1A-1D show that VB-201 inhibits formation of p-IKK, p-ERK and p-p38 and p-AKT induced by LPS in human monocytes in a dose dependent manner. Accordingly, VB-201 inhibits LPS (TLR4)-induced signaling.

Example 2

VB-201 Inhibits PGN (TLR2)-Induced Signaling in Human Monocytes (THP-1 Cell Line)

Methods and Materials
Activation of Cells and Western Blotting

The monocytic THP-1 cell line was purchased from the American Type Tissue Culture Collection (ATCC Cat. No. TIB-202). Cells ($10^6$/ml) were pretreated for 20 min with VB-201 at the doses indicated in FIG. 2, or with solvent, followed by activation with 20 µg/ml peptidoglycan (PGN) (InvivoGen, San Diego, Calif.) for 15 minutes, or were untreated ("Unt"). Cells were washed and resuspended in lysis buffer containing 1:100 dithiothreitol (DTT), phosphatase and protease inhibitors (Thermo Scientific). Samples were loaded onto a precast Criterion TGX gel (Bio-Rad, Hemel Hempstead, UK) and transferred onto nitrocellulose membrane. Blots were blocked with 5% milk or BSA in Tris buffered saline and Tween 20 (TBST) for 1 h, followed by incubation with primary and secondary antibodies. Membranes were developed using an ECL kit (Thermo Scientific). The following antibodies were used for immunoblotting:

Primary antibodies: p-p38 (Cat. No. 4511; 1:1000) and p-IKK (Cat. No. 2697; 1:1000) were from Cell Signaling Technology (Danvers, Mass., USA). p-ERK1/2 (Cat. No. M8159; 1:10000) was purchased from Sigma (Israel). αTubulin served as a loading control.

Secondary antibodies: HRP donkey anti-rabbit (1:5000) and HRP goat anti-mouse (1:3000) were from Jackson ImmunoResearch (West Grove, Pa., USA). HRP donkey anti-goat (1:5000) was from Santa Cruz Biotechnology.
Results THP-1 cells were treated and analyzed by western blot. FIGS. 2A-2B show that VB-201 inhibits formation of p-IKK, p-ERK and p-p38 induced by PGN in THP-1 cells. Accordingly, VB-201 inhibits PGN (TLR2)-induced signaling.

Example 3

VB-201 Inhibits MCP-1-Induced Signaling in Human Monocytes (THP-1 Cell Line)

Methods and Materials
Activation of Cells and Western Blotting

THP-1 cells ($10^6$/ml) were pretreated for 20 min with VB-201 at the doses indicated in FIG. 4, or with solvent, followed by activation with 50 ng/ml MCP1, or were untreated ("Unt"). Cells were washed and resuspended in lysis buffer containing 1:100 dithiothreitol (DTT), phosphatase and protease inhibitors (Thermo Scientific). Samples were loaded onto a precast Criterion TGX gel (Bio-Rad, Hemel Hempstead, UK) and transferred onto nitrocellulose membrane. Blots were blocked with 5% milk or BSA in Tris buffered saline and Tween 20 (TBST) for 1 h, followed by incubation with primary and secondary antibodies. Membranes were developed using an ECL kit (Thermo Scientific). The following antibodies were used for immunoblotting:

Primary antibodies: p-ERK1/2 (Cat. No. M8159; 1:10000) was purchased from Sigma (Israel). p-AKT (Cat. No. 4060; 1:1000) was purchased from Cell Signaling Technology (Danvers, Mass.). αTubulin served as a loading control and was purchased from Sigma (Israel).

Figure 3:
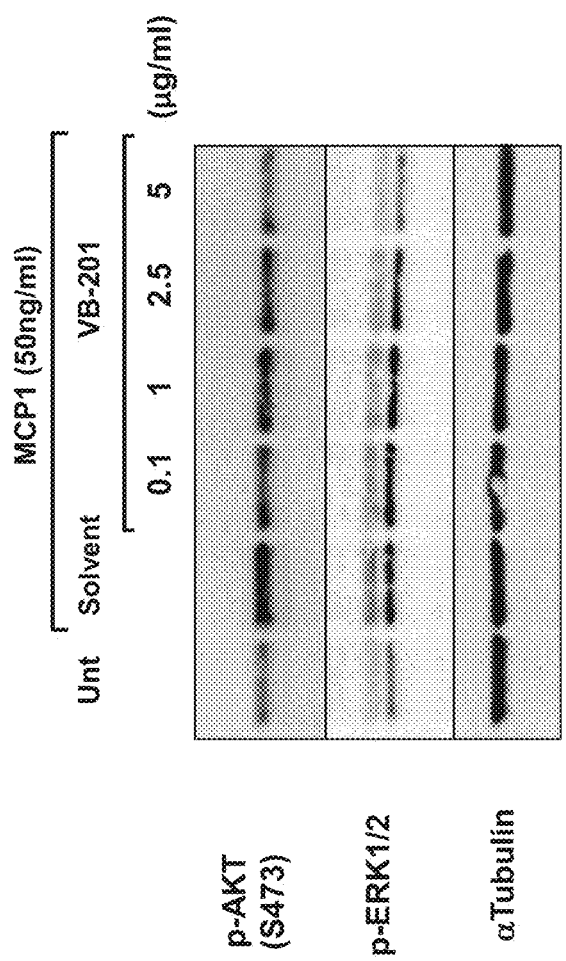
FIG. 3 shows VB-201 inhibits MCP-1-induced signaling in human monocytes (THP-1 cell line).

Secondary antibodies: HRP donkey anti-rabbit (1:5000) and HRP goat anti-mouse (1:3000) were from Jackson ImmunoResearch (West Grove, Pa., USA). HRP donkey anti-goat (1:5000) was from Santa Cruz Biotechnology.
Results FIG. 3 shows that VB-201 inhibits formation of p-AKT and p-ERK induced by MCP-1 in THP-1 cells. Accordingly, VB-201 inhibits MCP-1-induced signaling.

Example 4

VB-201 Inhibits Chemokine-Induced Migration of Human Monocytes (Primary CD14+)

Methods and Materials
Isolation of Monocytes

Venous blood samples were obtained from healthy male donors in compliance with the Institutional Review Board at the Sheba Medical Center, Ramat Gan, Israel. PBMCs were isolated on Ficoll-Paque PLUS (GE Healthcare, Uppsala, Sweden) using 50 ml Leucosep tubes (Greiner Bio-One, Frickenhausen, Germany). Cells were washed in PBS (Kibbutz Beit Haemek, Israel) and incubated at 4° C. for 15 minutes in a buffer containing PBS and 0.5% bovine serum albumin (BSA) with human CD14 microbeads (Miltenyi Biotec, Bergisch Gladbach, Germany).

Activation of Cells and Cell Migration Trans-Well Assay

Cells ($10^6$/ml) were pretreated for 20 min with VB-201 at the doses indicated in FIG. 5, or with solvent (Sol).

To test for chemokine-induced cell migration, RANTES (100 ng/ml; Cat. No. 300-06, PeproTech, Israel) and MCP-1 (50 ng/ml; Cat. No. 300-04, PeproTech, Israel) were dissolved in RPMI-1640 medium supplemented with 0.5% fetal bovine serum (FBS) and placed at the lower chamber of QCM 24-well, 5 mm pore, migration assay plates (Corning-Costar, Corning, N.Y.). Cells ($3 \times 10^5$) were seeded in the upper chamber and incubated for 2-4 hours. Subsequently, the number of cells which migrated to the lower compartment was determined by fluorescence-activated cell sorting (FACS).
Results Human monocytes were treated and analyzed for cell migration by trans-well assay. FIG. 4 shows that VB-201 inhibits chemokine-induced migration of human monocytes (primary CD14+).

Example 5

VB-201 Inhibits SDF1-Induced Migration in Human Monocytes (THP-1 Cell Line)

Methods and Materials

THP-1 cells ($10^6$/ml) were pretreated for 20 min with VB-201 or with solvent (Sol). To test for chemokine-induced cell migration, RANTES (100 ng/ml, Cat. No. 300-06) (PeproTech, Israel) and MCP-1 (50 ng/ml, Cat. No. 300-04) (PeproTech, Israel) were dissolved in RPMI-1640 medium supplemented with 0.5% fetal bovine serum (FBS) and placed at the lower chamber of QCM 24-well, 5 mm pore, migration assay plates (Corning-Costar, Corning, N.Y.). Cells ($3 \times 10^5$) were seeded in the upper chamber and incubated for 2-4 hours. Subsequently, the number of cells which migrated to the lower compartment was determined by fluorescence-activated cell sorting (FACS).

Results

FIG. 5 shows VB-201 inhibits SDF1-induced migration of human monocytes (THP-1 cell line).

Example 6

VB-201 Inhibits RANTES-Induced Signaling in Human Monocytes (Primary CD14+)

Human monocytes were obtained, treated and analyzed by western blot as described in Example 1 and FIG. 6, except that cells were induced with RANTES (100 ng/ml; Cat. No. 300-06, PeproTech, Israel) for 15 minutes. FIG. 6 shows that VB-201 inhibits formation of p-ERK. induced by RANTES in human monocytes. Accordingly, VB-201 inhibits RANTES-induced signaling.

Example 7

VB-201 Inhibits IL-12p40 Levels in Human Monocytes (Primary CD14+), Stimulated by LPS (Via TLR4) or Pam3CSK4 (Via TLR2)

Methods and Materials

Human monocytes were seeded ($10^6$/ml) and pretreated for 1 hour with VB-201, followed by 24 hour activation with 100 ng/ml LPS from *Escherichia coli* strain 055:B5 (Sigma, Israel) (FIG. 7A) or 300 ng/ml Pam3CSK4 (InvivoGen, San Diego, Calif., USA) (FIG. 7B) to induce cytokine production. IL-12/23p40 concentration in the supernatant was then measured by ELISA (R&D systems, Cat. No. DY1240). Cells activated with solvent (0.5% ethanol in PBS) were used as a control.

Results

Figure 7B:
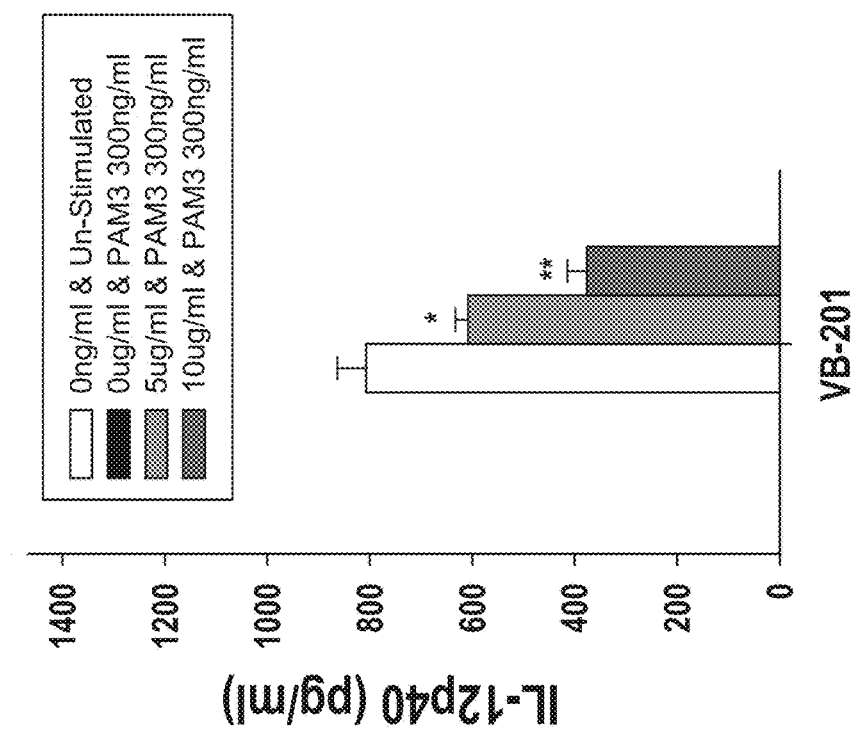
FIGS. 7A-7B show VB-201 inhibits IL-12p40 levels in human monocytes (primary CD14+) that are LPS (TLR4)-stimulated (FIG. 7A) and Pam3CSK4 (TLR2)-stimulated (FIG. 7B).
Figure 7A:
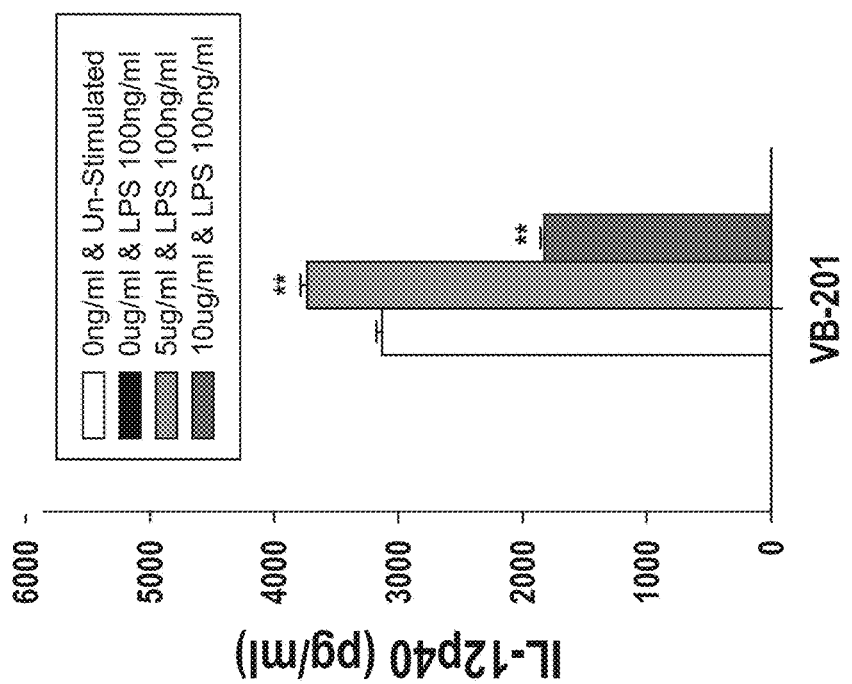

FIGS. 7A-7B show that VB-201 inhibits secretion of IL-12p40 by LPS (TLR4)-stimulated and Pam3CSK4 (TLR2)-stimulated human monocytes (primary CD14+).

Example 8

VB-201 Inhibits LPS Binding by Human Monocytes (Primary CD14+)

Methods and Materials

Isolation of Monocytes

Venous blood samples were obtained from healthy male donors in compliance with the Institutional Review Board at the Sheba Medical Center, Ramat Gan, Israel. PBMCs were isolated on Ficoll-Paque PLUS (GE Healthcare, Uppsala, Sweden) using 50 ml Leucosep tubes (Greiner Bio-One, Frickenhausen, Germany). Cells were washed in PBS (Kibbutz Beit Haemek, Israel) and incubated at 4° C. for 15 minutes in a buffer containing PBS and 0.5% bovine serum albumin (BSA) with human CD14 microbeads (Miltenyi Biotec, Bergisch Gladbach, Germany).

LPS Binding Inhibition Assay

To assess interference with lipopolysaccharide (LPS) binding, VB-201 were incubated for 20 min with cells ($10^6$/ml) after which 100 ng/ml of biotin-LPS (InvivoGen) was added for an additional 15 minutes, all at 4° C. Cells were washed, resuspended in FACS buffer and analyzed on a FACS-Calibur device.

FIG. 8 shows that VB-201 inhibited the binding to human monocytes (primary CD14+) of LPS with an IC50 of ~7 µg/ml.

Example 9

VB-201 Inhibits IL-6 Secretion in LPS (TLR4)-Stimulated Monocyte-Derived Dendritic Cells (Mo-Derived DCs)

Methods and Materials

To generate monocyte-derived DC (Mo-Derived DCs), CD14+ monocytes were counted, washed and seeded ($10^6$/ml) in medium containing RPMI-1640, L-glutamine, β-mercaptoethanol, 10% fetal calf serum (FCS), sodium pyruvate, non-essential amino acids, 0.01 M HEPES, antibiotics (penicillin, streptomycin), 50 ng/ml human granulocyte-macrophage colony-stimulating factor (GMCSF) and 20 ng/ml human IL-4 (both from PeproTech Asia, Israel). Medium was replaced every 2-3 days. Mo-DCs were collected 5-6 days post-culture, counted and seeded ($10^6$/ml). Cells were pretreated for 1 hour with VB-201, followed by 24 hours activation with 100 ng/ml LPS from *Escherichia coli* strain 055:B5 (Sigma, Israel) to induce cytokine production. IL-6 concentration (FIG. 9) in supernatant was measured by ELISA (R&D systems, Cat. No. DY206). Cells activated with solvent (0.5% ethanol in PBS) were used as a control.

Results

Figure 9:
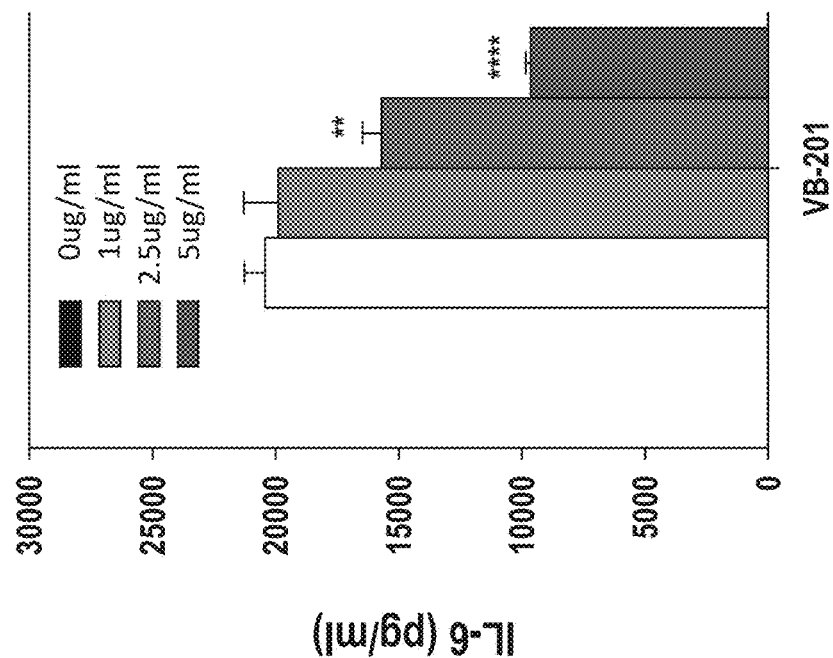
FIG. 9 shows VB-201 inhibits IL-6 secretion in LPS (TLR4)-stimulated human monocytes derived dendritic cells (Mo-derived DCs).

FIG. 9 shows VB-201 inhibits IL-6 secretion in LPS (TLR4) stimulated Mo-Derived DCs.

Example 10

VB-201 Inhibits IL-12p40 Secretion in LPS (TLR4) Stimulated Mo-Derived DCs

Mo-Derived DCs were obtained, treated and analyzed by ELISA as described in Example 9 and FIG. 10, except that IL-12p40 concentration in supernatant was measured by ELISA (R&D systems, cat. no DY1240). FIG. 10 shows VB-201 inhibits IL-12p40 secretion in LPS (TLR4) stimulated Mo-Derived DCs.

Example 11

VB-201 Effect on Liver Inflammation and Fibrosis

Methods and Materials

Induction of NASH and Liver Fibrosis

Neonatal male mice exposed to low-dose streptozotocin (STZ) develop liver steatosis with diabetes. Continuous high fat diet (HFD) increases lobular inflammation with foam cell-like macrophages, showing nonalcoholic steatohepatitis (NASH) pathology. NASH was induced in 40 male mice by a single subcutaneous injection of 200 μg per mouse of STZ two days after birth and feeding HFD [57 kcal % fat]) from four weeks of age. Vehicle, VB-201 (4 mg/kg), or telmisartan (10 mg/kg) as positive control, were administered once daily for three weeks, starting from six weeks of age. Mice were sacrificed at nine weeks of age.

Steatohepatitis and Fibrosis Evaluation

Liver pathology was used to determine the effect of VB-201 on liver inflammation and fibrosis. Histology slides were stained with hematoxylin/eosin (H&E) to assess inflammation. The inflammation score was determined as follows:

0—no inflammatory foci
1—<2 inflammatory foci
2—2-4 inflammatory foci
3—>4 inflammatory foci Histology slides were stained with Sirius red to determine collagen content as a marker for the extent of fibrosis.

Results

The effects of VB-201 on liver inflammation and fibrosis in a NASH mouse model were tested. FIGS. 11A-11B show that disease induction resulted in notable inflammation in the liver of vehicle treated mice. Treatment with VB-201 significantly curtailed inflammation by 65%. Administration with the positive control telmisartan significantly reduced liver inflammation by 77%. FIGS. 12A-12B show that disease induction in Example 11 also resulted in notable increases in the fibrosis area in the liver of vehicle treated mice. The results in FIGS. 12A-12B demonstrate that VB-201 significantly decreased the extent of fibrosis (by about 34%) compared to the vehicle treated mice.

Example 12

VB-201 Effect on Focal and Segmental Glomerulosclerosis

Methods and Materials
Animals and Experimental Protocol

Male Sprague Dawley (SD) Rats (Harlan Laboratories, Israel) with an initial weight of 200 g were housed 2-3 per cage in IVC cages in dedicated HVAC (heat, ventilation, air conditioning) animal facility. The facility had no exposure to outside light and was maintained on automatic alternating cycles of 12 hours of light and 12 hours of dark. Animals were provided with a commercial rodent diet (Harlan Teklad TRM Rat/Mouse Diet) ad libitum and allowed free access to autoclaved water, supplied to each cage via polysulphone bottles with stainless steel sipper tubes. All animal work was approved by the Animal Care and Use Committee of Israel (IL-13-03-027).

Induction of Chronic Renal Disease by 5/6 Nephrectomy

Rats were divided into three groups: (1) Healthy rats (n=3) in group A, (2) Sham group—subjected to chirurgical process but without kidney mass reduction (n=3) in group B, and (3) the rest were induced with chronic renal failure (n=24). Chronic renal failure was induced by a two stage (5/6) nephrectomy (Nx), with subtraction firstly of about ⅔ of the left kidney by left flank incision and, one week later, complete removal of the right kidney. General anesthesia consisted of intraperitoneal injection of ketamine 100 mg/kg and xylazine 20 mg/kg (0.85 ml ketamine+0.15 ml xylazine for each ml preparation; 1 μl/g BW was injected I.P).

Experimental Groups

One week following the second surgery, rats were randomly assigned to the following experimental groups:

Healthy, orally administered with vehicle—PBS 0.5% Ethanol (n=3);

Sham-operated, orally administered with vehicle—PBS 0.5% Ethanol (n=3);

Nephrectomized, orally administered with vehicle—PBS 0.5% Ethanol (n=8);

Nephrectomized, orally administered with VB-201 4 mg/kg (n=8); and

Nephrectomized, orally administered with telmisartan 10 mg/kg as positive control (n=8).

Body weight (BW) was monitored throughout the study and rats were treated by oral gavage according to their body weight for 7 weeks. Rats were sacrificed by $CO_2$ inhalation 8 weeks from removal of the right kidney ($2^{nd}$ surgery).

Kidney Collection

Upon sacrifice, at 8 weeks, kidneys were collected, weighed and fixed in 4% formaldehyde.

Renal Morphology and Morphometric Analysis

For light microscopy, paraffin-embedded tissue slides of 4 μm were stained with Periodic Acid-Schiff (PAS) reagent.

Glomerular Sclerosis Index.

Glomerulosclerosis was assessed by PAS-stained sections using a semiquantitative scoring system. The extent of glomerulosclerosis was evaluated by examining mostly 100 randomly selected glomeruli at a magnification of ×400 and applying a score system according to the percentage of sclerosed glomerular area. The score was graded from 0 to 4: (0=0% area; 1=1-25%; 2=26-50%, 3=51-75%, 4=76% and above). The mean of all scored glomeruli was presented. Moreover, the extent of global and segmental glomerulosclerosis was evaluated in the same glomeruli, where <80% sclerosis was referred to as segmental and >80% was referred to as global.

Glomerular Area.

The glomerular area of mostly 100 randomly selected glomeruli at a magnification of ×100 was quantitated by counting squares covered by glomeruli area using a grid and the mean glomeruli area was calculated.

Immunohistochemistry.

Renal tissues were fixed in 4% formaldehyde and embedded in paraffin. The paraffin-embedded tissues were then cut to form tissue slides of 4 μm. Immunohistochemistry of the paraffin-embedded tissue slides was analyzed using antibodies in the following concentration: monoclonal mouse anti rat CD-68 (ED-1, Serotec MCA341) 1:25. For quantitation of interstitial CD68+ staining, the number of positive cells was counted in 20 randomly selected non-overlapping fields per animal, and the mean value was presented.

Real-Time PCR.

Kidney RNA was extracted with an RNeasy Fibrous Tissue Mini kit (Qiagen) and after DNAse I treatment, single-stranded cDNA was synthesized from 2 mg total RNA using the qScript cDNA Synthesis Kit (Quanta Biosciences) and diluted for real-time PCR. The expression of collagen 4a, fibronectin and TGFβ was quantified using the 7300 Real Time PCR System (Applied Biosystems). The assay was performed according to manufacturer instructions using the primers (Assay ID) represented at the table below supplied by Applied Biosystems. Data were normalized to the reference gene TATA-box Binding Protein (TBP) and presented as relative mRNA levels compared with Sham PBS 0.5% Eth treatment (Table 1).

TABLE 1

Gene Expression references

| Assay ID | Gene Symbol | Gene Name |
|---|---|---|
| Rn01482927_m1 | Col IVα1 | Collagen; type IV; alpha 1 |
| Rn00572010_m1 | TGFβ1 | Transforming growth factor; beta 1 |
| Rn01455646_m1 | TBP | TATA box binding protein |

Statistics

Data are expressed as means±SEM. Statistical significance was determined by one-way ANOVA or Student's t-test where appropriate. Statistical analyses were performed using Sigma Stat software.

Results

VB-201 Treatment Effect on Glomerular Damage

Glomeruli were evaluated for their fibrosis extent by scoring and by calculation of the percent of glomeruli having segmental sclerosis, global sclerosis and the sum of global and segmental sclerotic glomeruli. Moreover, the area of the glomeruli was calculated and the percent of hypertrophied glomeruli was calculated. Damaged glomeruli included hypertrophied (at least ×1.5 from normal area) and or sclerotic glomeruli.

VB-201 and telmisartan treatment significantly reduced the damaged glomeruli by 29% (p=0.01) and 31% (p≤0.005), respectively (FIG. 13). This effect was partially contributed by the reduction in glomeruli hypertrophy. The major contribution to the reduction in glomeruli damage was due to the reduction in sclerotic glomeruli. VB-201 and telmisartan treatment resulted in a 34% (p≤0.05) and 57% (p≤0.005) reduction of sclerotic glomeruli, respectively (FIG. 14, Table 2).

TABLE 2

Effect of VB-201 on Glomerular sclerosis (Mean ± S.E)*

| | Treatment | | | | |
|---|---|---|---|---|---|
| | Healthy PBS 0.5% Eth | Sham PBS 0.5% Eth | Nx PBS 0.5% Eth | Nx VB-201 4 mg/kg | Nx Telmisartan 10 mg/kg |
| Glomerular sclerosis | | | | | |
| Segmental % | 1.0 ± 0.58 (n = 3) p ≤ 0.001 | 1.3 ± 0.88 (n = 3) p ≤ 0.001 | 41.0 ± 4.81 (n = 7) | 26.5 ± 4.39 (n = 8) P < 0.05 | 19.1 ± 4.30 (n = 8) P = 0.005 |
| Global % | 0.0 ± 0.00 (n = 3) n.s | 0.0 ± 0.00 (n = 3) n.s | 7.1 ± 4.39 (n = 7) | 5.4 ± 3.22 (n = 8) n.s | 1.9 ± 1.60 (n = 8) n.s |
| Global & Segmental % | 1.0 ± 0.58 (n = 3) p ≤ 0.001 | 1.3 ± 0.88 (n = 3) p ≤ 0.001 | 48.3 ± 5.38 (n = 7) | 31.8 ± 4.92 (n = 8) P < 0.05 | 21.0 ± 5.45 (n = 8) P < 0.005 |

*Number of animals tested per group and p value versus Nx PBS 0.5% Eth group is presented.

FIG. 15 shows typical sclerotic changes in glomeruli (PAS staining) of vehicle treated nephrectomized animals in contrast with healthy or sham operated animals or with VB-201 treated animals or telmisartan treated animals.

Figure 16C:
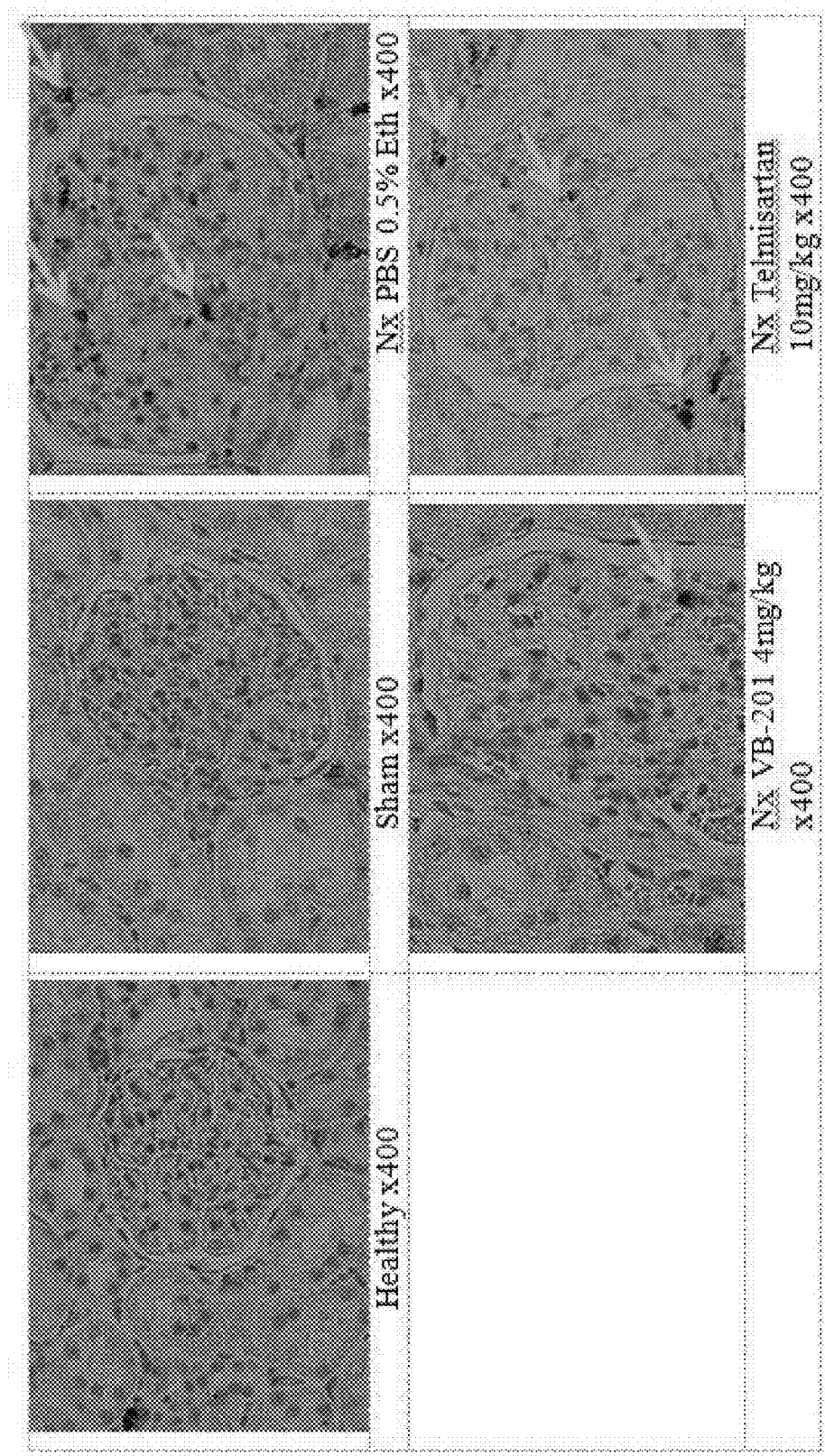

VB-201 Treatment Effect on Glomerular and Interstitial Monocyte/Macrophage Infiltration The number of monocytes/macrophages that infiltrated into the glomeruli was evaluated 8 weeks after surgery. (ED-1/CD68+) were significantly (p≤0.001) higher by 11 or 4 fold, respectively, in vehicle treated nephrectomized rats (3.669±0.324), in contrast with healthy (0.320±0.040) or sham operated animals (0.880±0.139). VB-201 treatment significantly (p=0.008) reduced the number of glomerular monocytes/macrophages by 42% (2.113±0.374) compared to those observed for Nx PBS 0.5% Eth treatment. Telmisartan treated animals had 13% non-significant reduction (3.185±0.427) compared to those observed for Nx PBS 0.5% Eth treatment. (FIG. 16A, 16C and Table 3).

TABLE 3

Effect of VB-201 on Glomerular and Interstitial Monocyte/Macrophage Infiltration (Mean ± S.E)*

| Treatment | Healthy PBS 0.5% Eth | Sham PBS 0.5% Eth | Nx PBS 0.5% Eth | Nx VB-201 4 mg/kg | Nx Telmisartan 10 mg/kg |
|---|---|---|---|---|---|
| ED-1/CD68+ | | | | | |
| Interstitial Cells/mm$^2$ | 79.0 ± 7.77 (n = 3) $P = 0.005$ | 86.7 ± 16.18 (n = 3) $P = 0.005$ | 527.9 ± 72.93 (n = 7) | 269.3 ± 25.41 (n = 8) $P < 0.005$ | 421.0 ± 61.77 (n = 8) n.s |
| Glomerular Cells/ Glomeruli | 0.320 ± 0.040 (n = 3) $p \leq 0.001$ | 0.880 ± 0.139 (n = 3) $p \leq 0.001$ | 3.669 ± 0.324 (n = 7) | 2.113 ± 0.374 (n = 8) $P = 0.008$ | 3.185 ± 0.427 (n = 8) n.s |

*Number of animals tested per group and p value versus Nx PBS 0.5% Eth group is presented.

The number of interstitial monocytes/macrophages examined 8 weeks after surgery (ED-1/CD68+) were significantly (p=0.005) higher by 7 or 6 fold, respectively, in vehicle treated nephrectomized rats (527.9±72.93), in contrast with healthy (79.0±7.77) or sham operated animals (86.67±16.18). VB-201 treatment significantly (p≤0.005) reduced the number of interstitial monocytes/macrophages by 49% (269.25±25.41) compared to those observed for Nx PBS 0.5% Eth treatment. Telmisartan treatment reduced the number of interstitial monocytes/macrophages by 20% (421.0±61.77) compared to those observed for Nx PBS 0.5% Eth treatment (FIG. 16B and Table 3).

VB-201 Treatment Effect on Pro-Fibrotic Markers

The mRNA expression of Collagen IV was increased significantly by 7 or 8 fold, respectively, in vehicle treated nephrectomized rats (7.5±1.51), in contrast with healthy (1.1±0.12) or sham operated animals (1.0±0.32). VB-201 treatment significantly (p≤0.05) reduced Collagen IV expression by 42% (4.3±0.33) compared to those observed for Nx PBS 0.5% Eth treatment. A 41% reduction in Collagen IV expression was observed in the telmisartan treated nephrectomized rats (4.4±0.23) compared to those observed for Nx PBS 0.5% Eth treatment, with marginal significance (p=0.064) (FIG. 17A).

The mRNA expression of TGF-β was increased significantly by 10 or 8 fold, respectively, in vehicle treated nephrectomized rats (8.4±0.49), in contrast with healthy (0.9±0.24) or sham operated animals (1.0±0.23) (p≤0.001). VB-201 and telmisartan treatment significantly (p≤0.001) reduced TGF-β expression by 37% (5.3±0.33) and 44% (4.7±0.52), respectively, compared to those observed for Nx PBS 0.5% Eth treatment (FIG. 17B).

Example 13

VB-201 Inhibits Expression of IL-12/23p40 in Livers of NASH-Induced Mice

NASH-induced mice were orally administered VB-201 at a dose of 4 mg/kg or telmisartan at a dose of 10 mg/kg once daily from Week 6 to Week 9. RNA was prepared from livers from normal mice and NASH-induced mice treated with vehicle, VB-201, or telmisartan, using RNeasy mini kit (Qiagen). For cDNA preparation, 2 μg of RNA was combined with the qScript reaction mix and qScript Reverse Transcriptase (Quanta BioSciences) for 5 min at 22° C. and then for 30 min at 42° C. The reaction was ended by incubation for an additional 5 min at 85° C. All real time PCR reactions were performed using the 7300 Real Time PCR System (Applied Biosystems). Q-PCR was performed with sets of probe with primer for mouse IL-12/23p40 (Applied Biosystems). GAPDH was used to normalize RNA levels.

FIG. 18 shows that VB-201 inhibits IL-12/23p40 expression in livers of NASH-induced mice. Analysis of IL-12/23p40 in the livers of NASH-induced mice shows that VB-201 significantly attenuated the expression of IL-12/23p40.

All publications, patents and patent applications mentioned in this application are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of treating fibrosis, comprising administering to a subject in need thereof a therapeutically effective amount of a compound having a structure according to Formula 4c:

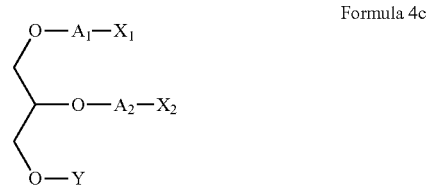

Formula 4c or a pharmaceutically acceptable salt thereof; wherein:
A$_1$ is CH$_2$;
A$_2$ is absent or CH$_2$;
X$_1$ is an alkyl having from 8 to 30 carbon atoms;
X$_2$ is

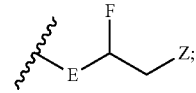

wherein:
E is absent or is an alkyl chain having from 1 to 4 carbon atoms;
F is hydrogen; and
Z is

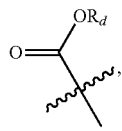

wherein $R_d$ is H;
Y is selected from the group consisting of phosphoryl choline, phosphoryl ethanolamine, and phosphoryl serine; and
wherein the fibrosis is liver fibrosis, kidney fibrosis, or skin fibrosis.

2. The method of claim 1, wherein $X_1$ of the structure is an alkyl having from 10 to 30 carbon atoms.

3. The method of claim 1, wherein Y of the structure is phosphoryl choline.

4. The method of claim 1, wherein the compound is 1-hexadecyl-2-(4'-carboxybutyl)-glycero-3-phosphocholine (VB-201).

5. The method of claim 4, wherein the compound is (R)-1-hexadecyl-2-(4'-carboxybutyl)-sn-glycero-3-phosphocholine.

6. The method of claim 1, wherein the compound inhibits activity of TLR2, TLR4, or CD14 in a cell of the subject.

7. The method of claim 1, wherein the compound inhibits activity of TLR2 and TLR4 in a cell of the subject.

8. The method of claim 1, wherein the compound inhibits activity of TLR4 and CD14 in a cell of the subject.

9. The method of claim 1, wherein the compound inhibits activity of TLR2 and CD14 in a cell of the subject.

10. The method of claim 1, wherein the compound inhibits activity of TLR2, TLR4, and CD14 in a cell of the subject.

11. The method of claim 1, wherein the compound inhibits monocyte migration in a cell of the subject.

12. The method of claim 1, wherein the compound inhibits secretion of IL-6 from monocytes in a cell of the subject.

13. The method of claim 1, wherein the compound inhibits secretion of IL-12p40 from monocytes in a cell of the subject.

14. The method of claim 1, wherein the fibrosis is liver fibrosis.

15. The method of claim 1, wherein the fibrosis is kidney fibrosis.

16. The method of claim 15, wherein the kidney fibrosis is focal and segmental glomerulosclerosis.

17. The method of claim 1, wherein the fibrosis is skin fibrosis.

18. The method of claim 17, wherein the skin fibrosis is keloid fibrosis.

19. The method of claim 1, wherein the subject is a human.

* * * * *